(12) United States Patent
Baasov et al.

(10) Patent No.: US 9,149,536 B2
(45) Date of Patent: Oct. 6, 2015

(54) CONJUGATED ANTIMICROBIAL AGENTS

(71) Applicant: Technion Research & Development Foundation Limited, Haifa (IL)

(72) Inventors: Timor Baasov, Haifa (IL); Varvara Pokrovskaya, Nesher (IL); Valery Belakhov, Haifa (IL); Mariana Hainrichson, Kiryat-Haim (IL)

(73) Assignee: Technion Research & Development Foundation Limited, Haifa (IL)

( * ) Notice: Subject to any disclaimer, the term of this patent is extended or adjusted under 35 U.S.C. 154(b) by 0 days.

(21) Appl. No.: 14/461,494

(22) Filed: Aug. 18, 2014

(65) Prior Publication Data

US 2014/0357591 A1 Dec. 4, 2014

Related U.S. Application Data

(62) Division of application No. 13/260,590, filed as application No. PCT/IL2010/000257 on Mar. 25, 2010, now Pat. No. 8,809,286.

(60) Provisional application No. 61/164,951, filed on Mar. 31, 2009.

(51) Int. Cl.
*A61K 47/48* (2006.01)
*A01N 43/60* (2006.01)

(52) U.S. Cl.
CPC .......... *A61K 47/48092* (2013.01); *A01N 43/60* (2013.01); *A61K 47/481* (2013.01)

(58) Field of Classification Search
CPC . A61K 47/481; A61K 47/48092; A01N 43/60
USPC ..................................... 514/39, 41
See application file for complete search history.

(56) References Cited

U.S. PATENT DOCUMENTS

| 7,973,022 B2 * | 7/2011 | Murthy ........................... 514/58 |
| 2006/0105941 A1 | 5/2006 | Schiffman et al. |
| 2012/0018334 A1 | 1/2012 | Baasov et al. |

FOREIGN PATENT DOCUMENTS

| WO | WO 03/040104 | 5/2003 | |
| WO | WO 03/040104 A1 * | 5/2003 | ........... C07D 215/56 |
| WO | WO 2009/037592 | 3/2009 | |
| WO | WO2009/037592 * | 3/2009 | ........... C07H 19/056 |
| WO | WO 2010/113151 | 10/2010 | |

OTHER PUBLICATIONS

Pokrovskaya et al, J. Med, Chem., 2009, 52, 2243-54.*
Wikipedia, 2007/2008, pp. 1-4.*
The Merck Manual, 1992, pp. 272-277.*
Advisory Action Before the Filing of An Appeal Brief Dated Jan. 24, 2014 From the US Patent and Trademark Office Re. U.S. Appl. No. 13/260,590.
Communication Pursuant to Article 94(3) EPC Dated Mar. 26, 2014 From the European Patent Office Re. Application No. 10716415.4.
International Preliminary Report on Patentability Dated Oct. 13, 2011 From the International Bureau of WIPO Re. Application No. PCT/IL2010/000257.
International Search Report and the Written Opinion Dated Sep. 17, 2010 From the International Searching Authority Re. Application No. PCT/IL2010/000257.
Notice of Allowance Dated Apr. 10, 2014 From the US Patent and Trademark Office Re. U.S. Appl. No. 13/260,590.
Official Action Dated Sep. 5, 2013 From the US Patent and Trademark Office Re. U.S. Appl. No. 13/260,590.
Official Action Dated Feb. 6, 2013 From the US Patent and Trademark Office Re. U.S. Appl. No. 13/260,590.
Restriction Official Action Dated Oct. 10, 2012 From the US Patent and Trademark Office Re. U.S. Appl. No. 13/260,590.
Bryskier "Dual ?-Lactam-Fluoroquinolone Compounds: A Novel Approach to Antibacterial Treatment", Expert Opinion on Investigational Drugs, XP002599062, 6(10): 1479-1499, 1997.
Gordeev et al. "Novel Oxazolidinone-Quinolone Hybrid Antimicrobials", Bioorganic & Medicinal Chemistry Letters, XP002599061, 13(23): 4213-4216, Dec. 1, 2003. Abstract, Fig.1, Table 1.
Long et al. "Novel Heterodimer Antibiotics: A Review of Recent Patent Literature", Future Medicinal Chemistry, 1(6): 1037-1050, Sep. 2009.

* cited by examiner

*Primary Examiner* — Ganapathy Krishnan

(57) ABSTRACT

Provided herein are antimicrobial conjugates of two antibiotic agents, exhibiting improved activity also against resistant bacteria, compared to each of the agents separately or their mixture, and having substantially no resistance emerged thereagainst, as well as processes for preparation the same, compositions containing the same, and uses thereof in medical treatments against pathogenic microorganisms. The disclosed antimicrobial conjugates are composed of aminoglycosides and non-ribosomal active antibiotics. Some of the antimicrobial conjugates are prepared via "click" chemistry.

32 Claims, 1 Drawing Sheet

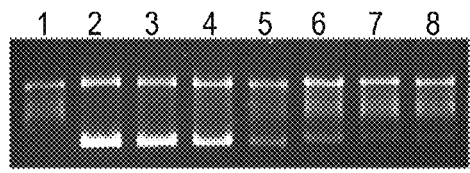
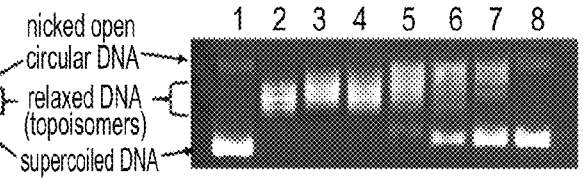
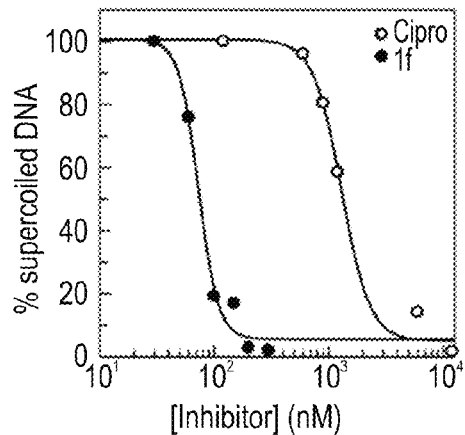
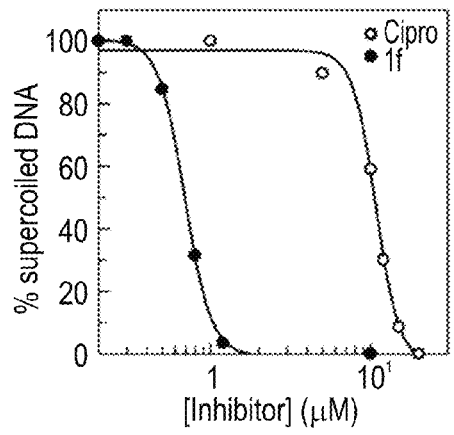
FIG. 1A  FIG. 1C
FIG. 1B  FIG. 1D
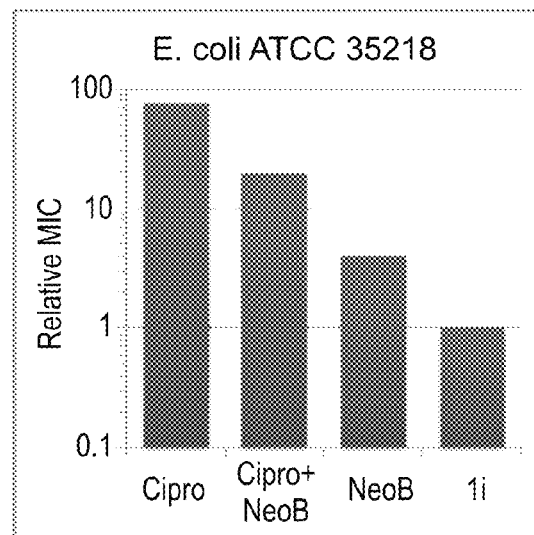
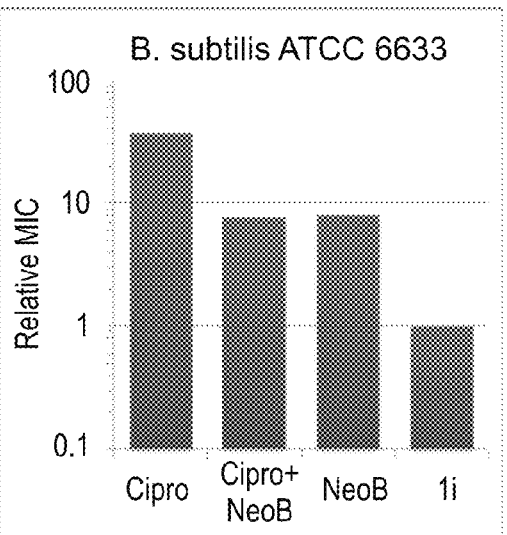
FIG. 2A  FIG. 2B

CONJUGATED ANTIMICROBIAL AGENTS

RELATED APPLICATIONS

This application is a division of U.S. patent application Ser. No. 13/260,590 filed on Sep. 27, 2011, which is a National Phase of PCT Patent Application No. PCT/IL2010/000257 having International filing date of Mar. 25, 2010, which claims the benefit of priority under 35 USC §119(e) of U.S. Provisional Patent Application No. 61/164,951 filed on Mar. 31, 2009. The contents of the above applications are all incorporated herein by reference.

FIELD AND BACKGROUND OF THE INVENTION

The present invention, in some embodiments thereof, relates to antimicrobial agents, and more particularly, but not exclusively, to non-resistance inducing antimicrobial conjugates which are effective also against resistant bacteria, and to uses thereof in treating infections.

Early advancements in the field of antibiotics had transformed medical care and dramatically reduced illness and death from infectious diseases. However, over the decades, almost all the prominent infection-causing bacterial strains have developed resistance to antibiotics. Among the different classes of clinically important antibiotics that largely suffered from the resistance problem during the last few decades, is the aminoglycoside class of drugs. These antibiotics have broad-spectrum of activity against both Gram-negative and Gram-positive bacteria by selectively targeting bacterial protein synthesis machinery, and have been used for over fifty years. Such a prolonged clinical and veterinary use of currently available aminoglycosides has resulted in effective selection of resistance, which severely limits their usefulness.

Due to the limitations associated with the use of classical antibiotics, extensive studies have been focused on finding novel, efficient and non-resistance inducing antimicrobial/antibacterial agents.

The most prevalent mechanism in clinical isolates of resistant bacteria is the bacterial acquisition of aminoglycoside-modifying enzymes, which modify the antibiotics by N-acetyltransferase (AAC), 0-phosphotransferase (APH), and O-nucleotidylyltransferase (ANT) activities. Among these enzymes families, aminoglycoside 3'-phosphotransferases (APH(3')s), of which seven isozymes are known, are widely represented. These enzymes catalyze phosphorylation at the 3'-OH to of both neomycin and kanamycin classes of aminoglycosides, rendering the resulting phosphorylated products inactive.

Although most of these enzymes are typically monofunctional enzymes, the recent emergence of genes encoding bifunctional aminoglycoside-modifying enzymes is another complication relevant to the clinical use of aminoglycosides. Among these enzymes, the bifunctional AAC(6')/APH(2") enzyme has been detected in *Enterococcus, Staphylococcus*, and *Streptococcus* isolates, including the methicillin-resistant *Staphylococcus aureus* (MRSA), and has been the most extensively investigated, due to the large number of clinically important aminoglycosides that are susceptible for modification with this enzyme.

To tackle the problem of bacterial resistance caused by enzymatic modification, many analogs of aminoglycosides have been synthesized by direct chemical modification of existing aminoglycoside drugs [1, 2]. Earlier investigations in this direction have yielded several semi-synthetic drugs such as amikacin, dibekacin, and arbekacin [1, 3]. However, new resistance to these drugs has emerged soon after their introduction to the clinic [4, 5].

One strategy that has been pursued in recent years to overcome bacterial resistance to aminoglycoside drugs employs a combination of two different drugs in one molecule [6]. With this strategy, each drug moiety is designed to bind independently to two different biological targets and synchronously accumulate at both target sites. Such dual action drugs, also referred to as hybrid drugs or conjugate drugs, offer the possibility to overcome current resistance. In addition, these conjugate drugs may reduce the appearance of new resistant strains [7].

Several applications of this approach have been reported [8-10]. The dual action compounds, combining fluoroquinolone (enrofloxacin or norfloxacin) and cephalosporin (cefamandole) moieties with an amide linkage, were found potent against *Enterobacter* species [9]. Fluoroquinolone-anilinouracil conjugates linked via their secondary amino groups have also been synthesized [10]. A series of oxazolidinone-quinolone conjugate structures, which simultaneously act on two different cellular functions, DNA replication and protein synthesis, have been reported [7, 11]. Lead compounds of this series exhibited a balanced dual mode of action and overcome the majority of known resistance mechanisms to quinolones and linezolid in clinically relevant Gram-positive pathogens.

Investigations towards glycopeptide/beta-lactam heterodimers were reported, employing vancomycin and cephalosporin synthons which were chemically linked to yield heterodimer antibiotics [12].

U.S. Pat. No. 7,635,685 (see also [13]) teaches modifications of aminoglycoside neomycin B (NeoB) by linking a variety of sugars at C5"-OH group via glycosidic linkage, which results with a class of pseudo-pentasaccharides that exhibited similar or better antibacterial activities to that of the parent NeoB against selected bacterial strains. However, while the specificity constant values (kcat/Km) of these derivatives with the aminoglycoside resistance enzyme APH (3')-IIIa were in general lower than that of NeoB, the compounds exhibited inhibition values about 10-fold lower than that of NeoB, suggesting that several different conformations of the designed structures can bind the APH(3')-IIIa productively and lead to the enzyme-catalyzed phosphoryl transfer process.

Several other derivatives of non-sugar modifications of NeoB at the C5"-position were reported to exhibit enhanced antibacterial activity compared to the parent NeoB [14], however these derivatives also exhibited substrate promiscuity with respect to APH(3')-IIIa.

Additional background art includes a review of recent patent literature concerning heterodimers antibiotics [15], WO 2003/044034 and U.S. Patent Application having publication No. 2008300199.

SUMMARY OF THE INVENTION

The present invention, in some embodiments thereof, relates to antimicrobial agents, and more particularly, but not exclusively, to non-resistance inducing antimicrobial conjugates effective against non-resistant and resistant bacteria.

The present inventors have surprisingly uncovered that conjugation of aminoglycosides with non-ribosomal active antimicrobial agents results in a series of efficacious novel antimicrobial conjugate agents which are further characterized by lack of emergence of resistance thereagainst. The present inventors have utilized the "click" chemistry for preparing a class of such novel antimicrobial conjugates.

Hence, according to embodiments of one aspect of the present, there is provided a conjugate having the general formula I:

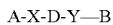   Formula I wherein:
A is a non-ribosomal-active antimicrobial agent moiety;
B is an aminoglycoside-based antimicrobial agent moiety;
X is a first spacer moiety, covalently bound to A, or absent;
Y is a second spacer moiety, covalently bound to B, or absent; and
D is a linking moiety having the general formula II:

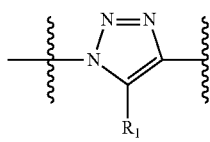   Formula II whereas each of the wiggled lines denote covalent bond to either A-X— or B—Y—, and $R_1$ is selected from the group consisting of hydrogen, alkyl and alkenyl.

According to some embodiments of the invention, the non-ribosomal-active antibiotic agent is selected from the group consisting of an anti-metabolite-based antimicrobial agent, a quinolone-based antimicrobial agent, a β-lactam-based antimicrobial agent, a glycopeptide-based antimicrobial agent, a benzyl-2,4-diaminopyrimidine-based antimicrobial agent, a sulfonamide-based antimicrobial agent, a sulfanilamide-based antimicrobial agent, a peptide-based antimicrobial agent, a pseudo-peptide-based antimicrobial agent and a peptidomimetic-based antimicrobial agent.

According to embodiments of another aspect of the present, there is provided a conjugate having the general formula III:

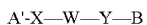   Formula III wherein:
A' is a quinolone-based antimicrobial agent moiety;
B is an aminoglycoside-based antimicrobial agent moiety;
X is a first spacer moiety, covalently bound to A, or absent;
Y is a second spacer moiety, covalently bound to B, or absent; and
W is a linking moiety.

According to some embodiments of the invention, the quinolone-based antimicrobial agent is selected from the group consisting of a fluoroquinolone, ciprofloxacin (Cipro, Ciprobay, Ciproxin), balofloxacin (Baloxin), cinoxacin (Cinobac), clinafloxacin, danofloxacin (Advocin, Advocid), delafloxacin, difloxacin (Dicural, Vetequinon), enoxacin (Enroxil, Penetrex), enrofloxacin (Baytril), fleroxacin (Megalone, Roquinol), flumequine (Flubactin), garenoxacin (Geninax), gatifloxacin (Tequin, Zymar), gemifloxacin (Factive), grepafloxacin (Raxar), ibafloxacin (Ibaflin), levofloxacin (Cravit, Levaquin), lomefloxacin (Maxaquin), marbofloxacin (Marbocyl, Zenequin), moxifloxacin (Avelox, Vigamox), nadifloxacin (Acuatim, Nadoxin, Nadixa), nalidixic acid (NegGam, Wintomylon), norfloxacin (Lexinor, Noroxin, Quinabic, Janacin), ofloxacin (Floxin, Oxaldin, Tarivid), orbifloxacin (Orbax, Victas), oxolinic acid (Uroxin), pazufloxacin (Pasil, Pazucross), pefloxacin (Peflacine), pipemidic acid (Dolcol), piromidic acid (Panacid), prulifloxacin (Quisnon), rosoxacin (Eradacil), rufloxacin (Uroflox), sarafloxacin (Floxasol, Saraflox, Sarafin), sitafloxacin (Gracevit), sparfloxacin (Zagam), temafloxacin (Omniflox), tosufloxacin (Ozex, Tosacin) and trovafloxacin (Trovan).

According to some embodiments of the invention, the quinolone-based antimicrobial agent is ciprofloxacin.

According to some embodiments of the invention, the ciprofloxacin is covalently bound to X via the terminal nitrogen of the piperazine moiety thereof.

According to some embodiments of the invention, the aminoglycoside-based antimicrobial agent is selected from the group consisting of neomycin B, neomycin C, streptomycin, framycetin, paromomycin, ribostamycin, kanamycin, amikacin, arbekacin, bekanamycin, dibekacin, tobramycin, spectinomycin, hygromycin, paromomycin, gentamicin, netilmicin, sisomicin, isepamicin, verdamicin and astromicin.

According to some embodiments of the invention, the aminoglycoside-based antimicrobial agent is covalently bound to Y via the C5"-position thereof.

According to some embodiments of the invention, the aminoglycoside-based antimicrobial agent is neomycin B.

According to some embodiments of the invention, the aminoglycoside-based antimicrobial agent is covalently bound to Y via the C1-N-position thereof.

According to some embodiments of the invention, the aminoglycoside-based antimicrobial agent is kanamycin A.

According to some embodiments of the invention, each of X and Y, when present, is independently selected from the group consisting of alkyl, alkenyl, alkynyl, cycloalkyl, heteroalicyclic, aryl, heteroaryl and a hydrocarbon chain having 1-20 carbon atoms and ending or interrupted by at least one heteroatom selected from the group consisting of O, S and N and/or containing from 0 to 19 unsaturated carbon-carbon or carbon-heteroatom bonds.

According to some embodiments of the invention, each of X and Y, when present, is independently selected from the group consisting of —$CH_2$—, —$CH_2$—O—, —$(CH_2)_2$—, —$(CH_2)_2$—O—, —$(CH_2)_3$—, —$(CH_2)_3$—O—, —$(CH_2)_4$—, —$(CH_2)_5$—, —$(CH_2)_6$—, —$(CH(CH_3))$—$CH_2$—, —CH═CH—CH═CH—, —C≡C—C≡C—, —$CH_2CH(OH)CH_2$—, —$CH_2$—O—$CH_2$—, —$CH_2$—O—$CH_2$—O—, —$(CH_2)_2$—O—$(CH_2)_2$—, —$(CH_2)_2$—O—$(CH_2)_2$—O—, —$CH_2$-m$C_6H_4$—$CH_2$—, —$CH_2$-p$C_6H_4$—$CH_2$—, —$CH_2$—NHCO—, —$C_6H_4$—NHCO—, —$CH_2$—O—$CH_2$— and —CH═CH—$CH_2$—NH—$(CH_2)_2$—.

According to some embodiments of the invention, W is selected from the group consisting of a covalent bond, amide, carboxylate, cycloalkene, cyclohexene, heteroalicyclic, heteroaryl, triazine, triazole, disulfide, lactone, lactam, imine, aldimine, ketimine, hydrazone and semicarbazone.

According to some embodiments of the invention, W is having the general formula II:

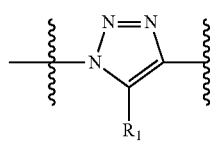   Formula II whereas each of the wiggled lines denote covalent bond to either A-X— or B—Y—, and $R_1$ is selected from the group consisting of hydrogen, alkyl and alkenyl.

According to some embodiments of the invention, $R_1$ is hydrogen.

According to some embodiments of the invention, A is selected from the group consisting of neomycin B and kanamycin A.

According to some embodiments of the invention, B is ciprofloxacin.

According to some embodiments of the invention, the conjugate presented herein is selected from the group consisting of N-(4-(1-(2-(ciprofloxacin)ethyl)-1H-1,2,3-triazol-4-yl)-5''-phenyl) neomycin, N-(4-(1-(2-(ciprofloxacin)propyl)-1H-1,2,3-triazol-4-yl)-5''-phenyl)neomycin carboxamide, N-(4-(1-(2-(ciprofloxacin)butyl)-1H-1,2,3-triazol-4-yl)-5''-phenyl)neomycin carboxamide, N-(4-(1-(2-(ciprofloxacin)pentyl)-1H-1,2,3-triazol-4-yl)-5''-phenyl)neomycin carboxamide, N-(4-(1-(2-(ciprofloxacin)hexyl)-1H-1,2,3-triazol-4-yl)-5''-phenyl)neomycin carboxamide, N-(4-(1-(2-hydroxy-3-(ciprofloxacin)propyl)-1H-1,2,3-triazol-4-yl)-5''-phenyl)neomycin carboxamide, N-(4-(1-(2-(2-(ciprofloxacin)ethoxy)ethyl)-1H-1,2,3-triazol-4-yl)-5''-phenyl)neomycin carboxamide, N-(4-(1-(4-((ciprofloxacin)methyl)benzyl)-1H-1,2,3-triazol-4-yl)-5''-phenyl)neomycin carboxamide, N-(4-(1-(3-((ciprofloxacin)methyl)benzyl)-1H-1,2,3-triazol-4-yl)-5''-phenyl)neomycin carboxamide, N-((1-(4-(ciprofloxacin)ethyl)-1H-1,2,3-triazol-4-yl)-5''-methyl)neomycin carboxamide, N-((1-(4-(ciprofloxacin)propyl)-1H-1,2,3-triazol-4-yl)-5''-methyl)neomycin carboxamide, N-((1-(4-(ciprofloxacin)pentyl)-1H-1,2,3-triazol-4-yl)-5''-methyl)neomycin carboxamide, N-((1-(2-hydroxy-3-(ciprofloxacin)propyl)-1H-1,2,3-triazol-4-yl)-5''-methyl) neomycin carboxamide, N-((1-(2-(2-(ciprofloxacin)ethoxy)ethyl)-1H-1,2,3-triazol-4-yl)-5''-methyl)neomycin carboxamide, N-((1-(3-((ciprofloxacin)methyl)benzyl)-1H-1,2,3-triazol-4-yl)-5''-methyl)neomycin carboxamide, N-((1-(4-((ciprofloxacin)methyl)benzyl)-1H-1,2,3-triazol-4-yl)-5''-methyl)neomycin carboxamide, 4-((5''-neomycin methoxy)methyl)-1-(2-(ciprofloxacin)ethyl)-1H-1,2,3-triazole, 4-(1-N-kanamycin methyl)-1-(2-(ciprofloxacin)ethyl)-1H-1,2,3-triazole, 1-(4-(1-N-kanamycin methyl)-1H-1,2,3-triazol-1-yl)-3-(ciprofloxacin)propan-2-ol and 4-(1-N-kanamycin methyl)-1-(4-((ciprofloxacin)methyl)benzyl)-1H-1,2,3-triazole.

According to some embodiments of the invention, the conjugate presented herein is identified for use in the treatment of a medical condition associated with a pathogenic microorganism in a subject.

According to embodiments of another aspect of the present, there is provided a process of preparing the conjugate of any of claims 1-20, the process is effected by:

reacting a compound having the general formula IV:

            Formula IV wherein:

A is a non-ribosomal-active antimicrobial agent moiety;

X is a first spacer moiety, covalently bound to A, or absent; and $RG_1$ is a first reactive group;

with a compound having the general formula V:

            Formula V wherein:

B is an aminoglycoside-based antimicrobial agent moiety;

Y is a second spacer moiety, covalently bound to B, or absent; and $RG_2$ is a second reactive group;

whereas one of $RG_1$ or $RG_2$ is alkynyl and the other is azide;

thereby forming the linking moiety D and obtaining the conjugate.

According to some embodiments of the invention, the conjugation reaction is performed in the presence of a copper(I) catalyst.

According to some embodiments of the invention, the conjugation reaction is performed at room temperature.

According to some embodiments of the invention, the conjugation reaction is performed under mild microwave irradiation.

According to some embodiments of the invention, the conjugation reaction is a "click" reaction.

According to embodiments of one aspect of the present, there is provided a process of preparing the conjugate of claim 3, the process is effected by:

reacting a compound having the general formula VI:

            Formula VI wherein:

A' is a quinolone-based antimicrobial agent moiety;

X is a first spacer moiety, covalently bound to A, or absent; and $RG_1'$ is a first reactive group;

with a compound having the general formula VII:

            Formula VII wherein:

B is an aminoglycoside-based antimicrobial agent moiety;

Y is a second spacer moiety, covalently bound to B, or absent; and $RG_2'$ is a second reactive group;

thereby forming W from $RG_1'$ and $RG_2'$.

According to some embodiments of the invention, one of $RG_1'$ or $RG_2'$ is selected from the group consisting of alkynyl, amine, alkoxy, aryloxy, diene, sulfhydryl, imino, carboxylate, hydrazide, hydrazide and hydroxylamine, and the other is selected from the group consisting of azide, aziridine, epoxy, carbonyl, thiocarbonyl, aldehyde, chloride, bromide, iodide, dienophile, mesylate, tresylate and tosylate.

According to embodiments of one aspect of the present, there is provided a pharmaceutical composition which includes, as an active ingredient, the conjugate presented herein and a pharmaceutically acceptable carrier.

According to some embodiments of the invention, the pharmaceutical composition presented herein is packaged in a packaging material and identified in print, in or on the packaging material, for use in the treatment of a medical condition associated with a pathogenic microorganism.

According to embodiments of another aspect of the present invention, there is provided a use of the conjugate presented herein in the preparation of a medicament.

According to some embodiments of the invention, the medicament is for treating a medical condition associated with a pathogenic microorganism.

According to embodiments of one aspect of the present, there is provided a method of treating a medical condition associated with a pathogenic microorganism in a subject, the method is effected by administering to the subject an effective amount of the conjugate presented herein.

According to some embodiments of the invention, the medical condition is selected from the group consisting of actinomycosis, anthrax, aspergillosis, bacteremia, bacterial skin diseases, *bartonella* infections, botulism, brucellosis, *burkholderia* infections, *campylobacter* infections, candidiasis, cat-scratch disease, *chlamydia* infections, cholera, *clostridium* infections, coccidioidomycosis, cryptococcosis, dermatomycoses, dermatomycoses, diphtheria, ehrlichiosis, epidemic louse borne typhus, *Escherichia coli* infections, *fusobacterium* infections, gangrene, general infections, general mycoses, gram-negative bacterial infections, Gram-positive bacterial infections, histoplasmosis, impetigo, *klebsiella* infections, legionellosis, leprosy, leptospirosis, *listeria* infections, lyme disease, maduromycosis, melioidosis, *mycobacterium* infections, *mycoplasma* infections, necrotizing fasciitis, *nocardia* infections, onychomycosis, ornithosis, pneumococcal infections, pneumonia, *pseudomonas* infections, Q fever, rat-bite fever, relapsing fever, rheumatic fever, *rickettsia* infections, Rocky-mountain spotted fever, *salmonella* infections, scarlet fever, scrub typhus, sepsis, sexually transmitted bacterial diseases, staphylococcal infections, streptococcal infections, surgical site infection, tetanus, tick-borne diseases, tuberculosis, tularemia, typhoid fever, urinary tract infection, *vibrio* infections, yaws, *yersinia* infections, *Yersinia pestis* plague, zoonoses and zygomycosis.

According to some embodiments of the invention, the microorganism includes at least one bacterial strain.

According to some embodiments of the invention, the bacterial strain is selected from the group consisting of a Gram negative organism, a Gram positive organism or a mycobacteria strain selected from the group consisting of *Strep. pyogenes* (Group A), *Strep. pneumoniae, Strep.* GpB, *Strep. viridans, Strep.* GpD (*Enterococcus*), *Strep.* GpC and GpG, *Staph. aureus, Staph. epidermidis, Bacillus subtilis, Bacillus anthracis, Listeria monocytogenes, Anaerobic cocci, Clostridium* spp., *Actinomyces* spp, *Escherichia coli, Enterobacter aerogenes, Kiebsiella pneumoniae, Proteus mirabilis, Proteus vulgaris, Morganella morganii, Providencia stuartii, Serratia marcescens, Citrobacter freundii, Salmonella typhi, Salmonella paratyphi, Salmonella typhi murium, Salmonella virchow, Shigella* spp., *Yersinia enterocolitica, Acinetobacter calcoaceticus, Flavobacterium* spp., *Haemophilus influenzae, Pseudomonas aeruginosa, Campylobacter jejuni, Vibrio parahaemolyticus, Brucella* spp., *Neisseria meningitidis, Neisseria gonorrhoea, Bacteroides fragilis, Fusobacterium* spp., *Mycobacterium tuberculosis* and *Mycobaterium smegmatis.*

According to some embodiments of the invention, the microorganism comprises at least one bacterial strain which is resistant to at least one antibiotic agent.

According to some embodiments of the invention, the bacterial strain is selected from the group consisting of:

(a) Gram-positive bacteria selected from the group consisting of *Strep. pyogenes* (Group A), *Strep. pneumoniae, Strep.* GpB, *Strep. viridans, Strep.* GpD-(*Enterococcus*), *Strep.* GpC and GpG, *Staph. aureus, Staph. epidermidis, Bacillus subtilis, Bacillus anthraxis, Listeria monocytogenes, Anaerobic cocci, Clostridium* spp., *Clostridium difficile* and *Actinomyces* spp; and (b) Gram-negative bacteria selected from the group consisting of *Escherichia coli, Enterobacter aerogenes, Kiebsiella pneumoniae, Proteus mirabilis, Proteus vulgaris, Morganella morganii, Providencia stuartii, Serratia marcescens, Citrobacter freundii, Salmonella typhi, Salmonella paratyphi, Salmonella typhi murium, Salmonella virchow, Shigella* spp., *Yersinia enterocolitica, Acinetobacter calcoaceticus, Flavobacterium* spp., *Haemophilus influenzae, Pseudomonas auroginosa, Campylobacter jejuni, Vibrio parahaemolyticus, Brucella* spp., *Neisseria meningitidis, Neisseria gonorrhoea, Bacteroides fragilis,* and *Fusobacterium* spp., *Acinetobacter baumanii, Pseudomonas aeruginosa*; and (c) *Mycobacterium tuberculosis.*

Abbreviations used herein include, "AAC" for aminoglycoside N-acetyltransferase; "APH" for aminoglycoside O-phosphotransferase; "ANT" for aminoglycoside O-nucleotidylyltransferase; "MRSA" for methicillin-resistant *Staphylococcus aureus*; "NeoB" for neomycin B; "Cipro" for ciprofloxacin; "TIPSCl" for triisopropylchlorosilane; "PMB" for para-methoxy benzyl; "TBAF" for tetra-n-butylammonium fluoride; "CAN" for cerium ammonium nitrate; "DCC" for N,N'-dicyclohexylcarbodiimide; "TEMPO" for 2,2,6,6-tetramethylpiperidine-1-oxyl; "BAIB" for [bis(acetoxy)iodo]benzene; "HOBT" for hydroxybenzotriazole; "MIC" for minimal inhibitory concentration; "TopoIV" for topoisomerase IV; and "IC50" for half maximal inhibitory concentration.

As used herein the term "about" refers to ±10%.

The terms "comprises", "comprising", "includes", "including", "having" and their conjugates mean "including but not limited to". The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings and images. With specific reference now to the drawings and images in detail, it is stressed that the particulars shown are by way of example and for purposes of illustrative discussion of embodiments of the invention. In this regard, the description taken with the drawings and images makes apparent to those skilled in the art how embodiments of the invention may be practiced.

In the drawings:

FIGS. 1A-D present comparative data for the inhibition of DNA gyrase (FIGS. 1A-B) and TopoIV (FIGS. 1C-D) with Cipro and exemplary Compound 1f, wherein FIG. 1A is a photograph of a 1% agarose gel showing the inhibitory activity of Compound 1f against DNA gyrase (lane 1, relaxed DNA; lane 2, supercoiling reaction by DNA gyrase without presence of inhibitor; lanes 3-8 are the same as lane 1 but in the presence of 30, 60, 100, 150, 200, and 300 nM of Compound 1f); FIG. 1B is a semilogarithmic plot of in vitro DNA gyrase supercoiling reaction inhibition, measured for Cipro and Compound 1f; FIG. 1C is a photograph of a 1% agarose gel showing the inhibitory activity of Compound 1f against TopoIV (lane 1, supercoiled DNA; lane 2, relaxation reaction by TopoIV without the presence of inhibitor; lanes 3-8 are the same as lane 1 but in the presence of 0.2, 0.3, 0.5, 0.8, 1.2, and 10 μM of Compound 1f; FIG. 1D is a semilogarithmic plot of TopoIV inhibition, measured for Cipro and Compound 1f; while the percentages of the supercoiled DNA were calculated from the electrophoresis images by using ImageJ Launcher program (Rasband, W. Bethesda, Md., USA), and plotted as functions of drug concentration (each data point represents the average of 2-3 independent experimental results); and FIGS. 2A-B present comparative data on the emergence of resistance in *E. coli* (FIG. 2A) and *B. subtilis* (FIG. 2B) after 15 serial passages in the presence of Cipro, NeoB, Cipro+NeoB mixture (1:1 molar ratio) and an exemplary conjugate, according to some embodiments of the present invention, Compound 1i, wherein relative MIC is the normalized ratio of MIC obtained for a give subculture to MIC obtained upon first exposure.

DESCRIPTION OF EMBODIMENTS OF THE INVENTION

The present invention, in some embodiments thereof, relates to antimicrobial agents, and more particularly, but not exclusively, to non-resistance inducing antimicrobial conjugates which are effective also against resistant bacteria, and to uses thereof in treating infections.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

In search for a solution to the prevalent problem of bacterial resistance caused by enzymatic modification, as discussed hereinabove, the present inventors have devised and successfully prepared and practiced novel antimicrobial conjugates that act by applying bactericidal pressure on two different essential systems of the microorganisms while being present in the microorganism cell as one conjugated molecule. To this end, the present inventors have utilized the "click" chemistry to conjugate aminoglycosides, which are known to act on ribosomal-related mechanisms, to antimicrobial agents which exert their antibiotic effect on non-ribosomal mechanisms.

The present invention, according to some embodiments thereof, describes the synthesis and biological evaluation of antimicrobial conjugates, comprising antimicrobial agents such as, for example, members of the fluoroquinolone family (e.g., ciprofloxacin or Cipro) and the aminoglycoside family (e.g., neomycin B or NeoB). These conjugates comprise two pharmacophores which are active by different antimicrobial mechanism; one side is anti-ribosomal, while the other is non-ribosomal.

The present inventors have shown that by utilizing the "click chemistry" described herein, combinatorial synthesis from relatively simple building blocks can afford a wide family of novel antimicrobial conjugates. Particularly, the present inventors have devised and successfully practiced novel methods for preparing azides and alkynes bearing antimicrobial agent moieties, such as fluoroquinolone and aminoglycosides, which can be efficiently utilized for forming this novel family of conjugates.

These conjugates, according to some embodiments of the present invention, exhibit high potency against both Gram-negative and Gram-positive bacteria including MRSA and strains harboring either the monofunctional APH(3') enzyme or the bifunctional AAC(6')/APH(2") enzyme. The conjugates, according to some embodiments of the present invention, overcome currently resistant bacteria, and in addition, reduce the appearance of new resistant strains thereagainst. The conjugates, according to some embodiments of the present invention, also exhibit a dual mode of antimicrobial activity by inhibiting both bacterial protein synthesis and topoisomerase/gyrase enzyme activity.

An exemplary conjugate which comprises neomycin B and ciprofloxacin, according to some embodiments of the present invention, was significantly more potent than the parent compound neomycin B, and showed antimicrobial activity against most prevalent types of resistance associated with aminoglycosides. The exemplary conjugate Cipro-NeoB, according to some embodiments of the present invention, inhibited bacterial protein synthesis with the potencies similar to or better than that of neomycin B, and were up to 32-fold more potent inhibitors than ciprofloxacin for the fluoroquinolone targets, DNA gyrase and toposimerase IV, indicating a balanced dual mode of action. Significant delay of resistance formation was observed in both *E. coli* and *B. subtilis* to the treatment with the exemplary Cipro-NeoB conjugate, according to some embodiments of the present invention, compared to that of each Cipro and NeoB used separately or as a 1:1 mixture.

While the mechanism of action of aminoglycosides is not fully understood, it is accepted that among several potential antibiotic mechanisms, their main mechanism of action involves direct interaction with one or more ribosomal subunits by binding to the ribosomal RNA (rRNA), thereby affecting microbial protein synthesis at the -translation level by inhibiting translocation step and total translation process. Aminoglycosides also interfere with the fidelity of protein synthesis through affecting the proofreading process, causing misreading and increased rate of error in synthesis with premature termination[16]. The present inventors have hypothesized that due the presence of positive charge which typically characterizes aminoglycosides, conjugates of aminoglycosides could afford favorable binding to DNA and/or DNA-protein interface, and therefore exhibit better inhibition and improved antibacterial activity when conjugated with antimicrobial agents, such as quinolones, which also interact with nucleic acids. The well-established binding of aminoglycosides to DNA [17], along with the inhibition of various nucleic acid metabolizing enzymes by aminoglycosides [18], supported this hypothesis.

The present inventors hypothesized that conjugates of aminoglycosides and non-ribosomal antimicrobial agents would provide superior antimicrobial effects, particularly when fighting resistant strains of pathogenic microorganisms. The concept was reduced to practice with quinolones conjugated to aminoglycosides, wherein the conjugation was exemplified by use of "click" chemistry.

The present inventors have thus prepared and tested a family of conjugates of neomycin B (NeoB, an aminoglycoside) and the fluoroquinolone ciprofloxacin (Cipro, a quinolone), prepared via "click" chemistry and linked via 1,2,3-triazole moiety (Cipro-NeoB or Compound 1).

The rational behind the selection of these two exemplary antimicrobial agents to form the parts of a new antimicrobial conjugate stems from their different mechanism of antimicrobial activity. Quinolones exert their antimicrobial activity by targeting bacterial DNA gyrase and topoisomerase IV (TopoIV) and inhibiting DNA replication process [19]. Particularly, quinolones bind to complexes that form between DNA and DNA gyrase or TopoIV. The quinolone-gyrase-DNA or quinolone-TopoIV-DNA complex formation inhibits DNA replication and cell growth, and is responsible for the bactericidal action of quinolones [20].

As demonstrated in the Examples section that follows and in the accompanying Tables and Figures, a variety of 20 exemplary conjugates of the aminoglycosides NeoB and KanA attached to Cipro where prepared by "click" chemistry, and tested for antimicrobial activity, rate of resistance emergence, inhibition of prokaryotic protein translation and inhibition of DNA girase and topoisomerase IV enzymes. The conjugates presented herein have been shown to possess highly effective antimicrobial trait while not evoking resistance thereto.

According to optional embodiments of the invention, the two antimicrobial agents are linked together through various linking and spacer moieties.

Hence, according to an aspect of some embodiments of the invention, there is provided a conjugate having the general formula III:

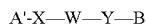    Formula III wherein:
A' is a quinolone-based antimicrobial agent moiety;
B is an aminoglycoside-based antimicrobial agent moiety;
X is a first spacer moiety, covalently bound to A, or absent;
Y is a second spacer moiety, covalently bound to B, or absent; and
W is a linking moiety.

As further demonstrated in the Examples section the follows, and is further discussed in detail hereinbelow, the present inventors have successfully utilized the "click" chemistry for preparing novel conjugates of aminoglycosides, and to this effect, have prepared versatile derivatives of aminoglycosides that could participate in a "click" reaction with complementary derivatives of non-ribosomal antimicrobial agents.

Hence, according to an aspect of some embodiments of the invention, there is provided a conjugate having the general formula I:

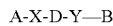    Formula I wherein:
A is a non-ribosomal-active antimicrobial agent moiety;
B is an aminoglycoside-based antimicrobial agent moiety;
X is a first spacer moiety, covalently bound to A, or absent;
Y is a second spacer moiety, covalently bound to B, or absent; and D is a linking moiety having the general formula II, as presented hereinbelow.

In the context of the present embodiments, the terms "antimicrobial agent", "antibacterial agent", "antibiotic agent" and "bactericidal agent" are used interchangeably.

As used herein, the term "moiety" describes portion of a molecule, and typically a major portion thereof.

The phrase "non-ribosomal-active antimicrobial agent", as used herein, refers to an agent which has a mechanism of antimicrobial action which does not involve direct interaction with a ribosomal subunit. Alternatively, this phrase refers to any antimicrobial agent having an antimicrobial mechanism which is different from that of aminoglycosides, as it is known in the art. Typically, the mechanism of antimicrobial action attributed to aminoglycosides is generally referred to as anti-protein-biosynthesis activity.

Exemplary non-ribosomal-active antimicrobial agents include, without limitation, anti-metabolite-based antimicrobial agents, quinoline- and fluoroquinolone-based antimicrobial agents (jointly referred to herein as quinolones), β-lactam-based antimicrobial agents, glycopeptide-based antimicrobial agents, benzyl-2,4-diaminopyrimidine-based antimicrobial agents, sulfonamide-based antimicrobial agents, sulfanilamide-based antimicrobial agents, peptide-based antimicrobial agents, pseudo-peptide-based antimicrobial agents and peptidomimetic-based antimicrobial agents.

Quinolones, which generally interfere with bacterial DNA replication, include, without limitation, ciprofloxacin (Cipro, Ciprobay, Ciproxin), balofloxacin (Baloxin), cinoxacin (Cinobac), clinafloxacin, danofloxacin (Advocin, Advocid), delafloxacin, difloxacin (Dicural, Vetequinon), enoxacin (Enroxil, Penetrex), enrofloxacin (Baytril), fleroxacin (Megalone, Roquinol), flumequine (Flubactin), garenoxacin (Geninax), gatifloxacin (Tequin, Zymar), gemifloxacin (Factive), grepafloxacin (Raxar), ibafloxacin (Ibaflin), levofloxacin (Cravit, Levaquin), lomefloxacin (Maxaquin), marbofloxacin (Marbocyl, Zenequin), moxifloxacin (Avelox, Vigamox), nadifloxacin (Acuatim, Nadoxin, Nadixa), nalidixic acid (NegGam, Wintomylon), norfloxacin (Lexinor, Noroxin, Quinabic, Janacin), ofloxacin (Floxin, Oxaldin, Tarivid), orbifloxacin (Orbax, Victas), oxolinic acid (Uroxin), pazufloxacin (Pasil, Pazucross), pefloxacin (Peflacine), pipemidic acid (Dolcol), piromidic acid (Panacid), prulifloxacin (Quisnon), rosoxacin (Eradacil), rufloxacin (Uroflox), sarafloxacin (Floxasol, Saraflox, Sarafin), sitafloxacin (Gracevit), sparfloxacin (Zagam), temafloxacin (Omniflox), tosufloxacin (Ozex, Tosacin) and trovafloxacin (Trovan).

As presented in the Examples section that follows below, ciprofloxacin (Cipro) was used as exemplary non-ribosomal-active antimicrobial agent in the preparation of two series of conjugates, according to some embodiments of the present invention.

β-Lactams, which generally inactivate bacterial transpeptidase enzymes, include, without limitation, penicillins, aminopenicillins, amoxicillin, ampicillin (pivampicillin, hetacillin, bacampicillin, metampicillin, talampicillin), epicillin, carboxypenicillins, carbenicillin (carindacillin), ticarcillin, temocillin, ureidopenicillins, azlocillin, piperacillin, mezlocillin, mecillinam (pivmecillinam), sulbenicillin, benzylpenicillins, clometocillin, benzathine benzylpenicillin, procaine benzylpenicillin, azidocillin, penamecillin, phenoxymethylpenicillins, propicillin, benzathine phenoxymethylpenicillin, pheneticillin, cloxacillin (dicloxacillin, flucloxacillin), oxacillin, meticillin, nafcillin, faropenem, biapenem, doripenem, ertapenem, imipenem, meropenem, panipenem, cefazolin, cefacetrile, cefadroxil, cefalexin, cefaloglycin, cefalonium, cefaloridine, cefalotin, cefapirin, cefatrizine, cefazedone, cefazaflur, cefradine, cefroxadine, ceftezole, cefaclor, cefamandole, cefminox, cefonicid, ceforanide, cefotiam, cefprozil, cefbuperazone, cefuroxime, cefuzonam, cephamycin (cefoxitin, cefotetan, cefmetazole), carbacephem (loracarbef), cefixime, ceftazidime, ceftriaxone, cefcapene, cefdaloxime, cefdinir, cefditoren, cefetamet, cefmenoxime, cefodizime, cefoperazone, cefotaxime, cefpimizole, cefpiramide, cefpodoxime, cefsulodin, cefteram, ceftibuten, ceftiolene, ceftizoxime, oxacephem (flomoxef, latamoxef), cefepime, cefozopran, cefpirome, cefquinome, ceftobiprole, ceftiofur, cefquinome, cefovecin, aztreonam, tigemonam, penam (sulbactam, tazobactam) and clavam (clavulanic acid).

Glycopeptides, which generally inhibit bacterial peptidoglycan synthesis, include, without limitation, vancomycin (oritavancin, telavancin), teicoplanin (dalbavancin) and ramoplanin.

Benzyl-2,4-diaminopyrimidines, which generally inhibit bacterial dihydrofolate reductase, include, without limitation, trimethoprim, brodimoprim, tetroxoprim and iclaprim.

Topoisomerase inhibitors, which generally inhibit bacterial DNA replication, include cinoxacin, flumequine, nalidixic acid, oxolinic acid, pipemidic acid, piromidic acid and rosoxacin.

RNA polymerase inhibitors, which generally inhibit bacterial RNA synthesis, include rifampicin, rifabutin, rifapentine and rifaximin.

Sulfonamides, which generally inhibit bacterial DNA and RNA synthesis, include sulfaisodimidine, sulfamethizole, sulfadimidine, sulfapyridine, sulfafurazole, sulfanilamide (prontosil), sulfathiazole, sulfathiourea, sulfamethoxazole, sulfadiazine, sulfamoxole, sulfadimethoxine, sulfalene, sulfametomidine, sulfametoxydiazine, sulfamethoxypyridazine, sulfaperin, sulfamerazine, sulfaphenazole and sulfamazone.

Sulfanilamides, which are generally regarded as bacterial PABA-antimetabolite, include sulfanilamide (sulfacetamide, sulfametrole), furosemide, sulfadiazine and sulfamethoxazole.

Other non-ribosomal (antimetabolite and/or not against protein biosynthesis) active antibiotics include, without limitation, D-cycloserine (inhibiting bacterial alanine racemase and D-ala-D-ala ligase), fosfomycin (inhibiting bacterial UDP-N-acetylglucosamine enolpyruvyl transferase), as well as metronidazole, tinidazole, ornidazole, nitrofurantoin and nifurtoinol (anaerobic bacteria's DNA inhibitors).

The other antimicrobial agent member of the conjugates, according to embodiments of the present invention, is an aminoglycoside-based antimicrobial agent, which is selected from the group consisting of neomycin B and neomycin C, streptomycin, framycetin, paromomycin, ribostamycin, kanamycin A, kanamycin B and kanamycin C, amikacin, arbekacin, bekanamycin, dibekacin, tobramycin, spectinomycin, hygromycin, paromomycin, gentamicin, netilmicin, sisomicin, isepamicin, verdamicin, astromicin and any derivative thereof.

As presented in the Examples section that follows below, neomycin B and kanamycin A were used as exemplary aminoglycosides in the preparation of two series of conjugates, according to some embodiments of the present invention.

According to some embodiments of the present invention, the conjugate comprises a linking moiety covalently attached to each of the antimicrobial agents in the conjugate, either directly or indirectly, via a spacer moiety, as this term is defined and exemplified hereinafter.

According some embodiments of the present invention, the antimicrobial agent moieties are attached to the linking moiety via spacer moieties.

As used herein, the phrase "spacer moiety" describes a chemical moiety that typically extends between two chemical moieties and is attached to each of the chemical moieties via covalent bonds. The spacer moiety may be linear or cyclic, be branched or unbranched, rigid or flexible.

The nature of the spacer moieties can be regarded as having an effect on two aspects, the synthetic aspect, namely the influence of the spacer moieties on the process of preparing the conjugates presented herein, and the influence of the spacer moieties on the biology activity of the conjugates in terms of antimicrobial activity, bioavailability and other ADME-Tox considerations.

According to some embodiments of the present invention, the spacer moieties are selected such that they allow and/or promote the conjugation reaction between the two halves of the conjugates and reduce the probability for the formation of side-products due to undesired reactions. Such traits can be selected for in terms of spacer's length, flexibility, structure and specific chemical reactivity or lack thereof. Spacer moieties with fewer reactive groups will present a simpler synthetic challenge, requiring less protection/deprotection steps and affording higher chemical yields. For example, saturated and linear alkyls of 1-10, or 1-5 carbon atoms, having one reactive group at the end atom for conjugation with a corresponding reactive group, would afford substantially higher yield and fewer side products. Similarly, a spacer moiety based on one or two chained benzyl rings would also lead to an efficient conjugation reaction.

On the other hand, the spacer moiety is selected such that its attachment to the antimicrobial agent, be it A, A' or B in formulae I and III, even at suitable positions as discussed hereinbelow, does not obliterate or otherwise preclude the antimicrobial activity of the antimicrobial agents substantially by virtue of its own chemical structure, namely due to its steric effect, physical effect (solubility, charge etc.), or chemical reactivity. For example, highly hydrophobic spacer moieties would lower the bioavailability of the conjugate by lowering its aqueous solubility. Highly flexible and long spacer moieties may lower the binding constant of the conjugates to their biological targets and may also present steric hindrance issues, adversely affecting binding.

As can be seen in the comparative experimental results presented hereinbelow, a simple spacer moiety, based on a saturated alkyl with or without a heteroatom along its chain, or a spacer moiety based on an aromatic ring, both having a length that corresponds to 2-7 carbon-carbon bonds and a relatively small number of degrees of rotational freedom, would afford an effective antimicrobial conjugate, according to some embodiments of the present invention, which is also reasonably simple to produce.

In the context of the present embodiments, the spacer moiety which is attached to A in formula I (or to A' in formula III) is denoted X and referred to as the first spacer moiety, and the spacer moiety which is attached to B in formula I (and in formula III) is denoted Y and referred to as the second spacer moiety.

According to some embodiments of the present invention, each of X and Y can be independently alkyl, alkenyl, alkynyl, cycloalkyl, heteroalicyclic, aryl, heteroaryl and/or a hydrocarbon chain having 1-20 carbon atoms and ending or interrupted by at least one heteroatom selected from the group consisting of O, S and N and/or containing from 0 to 19 unsaturated carbon-carbon or carbon-heteroatom bonds.

As used herein, the term "alkyl" describes an aliphatic hydrocarbon including straight chain and branched chain groups. Preferably, the alkyl group has 1 to 20 carbon atoms, and more preferably 1-10 carbon atoms. Whenever a numerical range; e.g., "1-10", is stated herein, it implies that the group, in this case the alkyl group, may contain 1 carbon atom, 2 carbon atoms, 3 carbon atoms, etc., up to and including 10 carbon atoms. The alkyl can be substituted or unsubstituted. When substituted, the substituent can be, for example, an alkyl, an alkenyl, an alkynyl, a cycloalkyl, an aryl, a heteroaryl, a halide, a hydroxy, an alkoxy and a hydroxyalkyl as these terms are defined hereinbelow.

The term "alkenyl" describes an unsaturated alkyl, as defined herein, having at least two carbon atoms and at least one carbon-carbon double bond. The alkenyl may be substituted or unsubstituted by one or more substituents, as described for alkyl hereinabove.

The terms "alkynyl" or "alkyne", as defined herein, is an unsaturated alkyl having at least two carbon atoms and at least one carbon-carbon triple bond. The alkynyl may be substituted or unsubstituted by one or more substituents, as described hereinabove.

The term "cycloalkyl" describes an all-carbon monocyclic or fused ring (i.e., rings which share an adjacent pair of carbon atoms) group where one or more of the rings does not have a completely conjugated pi-electron system. The cycloalkyl group may be substituted or unsubstituted as described for alkyl hereinabove.

The term "heteroalicyclic" describes a monocyclic or fused ring group having in the ring(s) one or more atoms such as nitrogen, oxygen and sulfur. The rings may also have one or more double bonds. However, the rings do not have a completely conjugated pi-electron system. The heteroalicyclic may be substituted or unsubstituted as described for alkyl hereinabove. Representative examples are piperidine, piperazine, tetrahydrofurane, tetrahydropyrane, morpholino and the like.

The term "aryl" describes an all-carbon monocyclic or fused-ring polycyclic (i.e., rings which share adjacent pairs of carbon atoms) groups having a completely conjugated pi-electron system. The aryl group may be substituted or unsubstituted. Substituted aryl may have one or more substituents as described for alkyl hereinabove.

The term "heteroaryl" describes a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine. The heteroaryl group may be substituted or unsubstituted as described for alkyl hereinabove. Representative examples of heteroaryls include triazole, furane, imidazole, indole, isoquinoline, oxazole, pyrazole, pyridine, pyrimidine, pyrrole, quinoline, thiazole, thiophene, triazine, purine and the like.

According to some embodiments of the present invention, the spacer moieties include, without limitation, —CH$_2$—, —CH$_2$—O—, —(CH$_2$)$_2$—, —(CH$_2$)$_3$—, —(CH$_2$)$_3$—, —(CH$_2$)$_3$—O—, —(CH$_2$)$_4$—, —(CH$_2$)$_5$—, —(CH$_2$)$_6$—, —(CH(CH$_3$))—CH$_2$—, —CH═CH—CH═CH—, —C≡C—C≡C—, —CH$_2$CH(OH)CH$_2$—, —CH$_2$—O—CH$_2$—, —CH$_2$—O—CH$_2$—O—, —(CH$_2$)$_2$—O—(CH$_2$)$_2$—, —(CH$_2$)$_2$—O—(CH$_2$)$_2$—O—, —CH$_2$-mC$_6$H$_4$—CH$_2$—, —CH$_2$-mC$_6$H$_4$—CH$_2$—O—, —CH$_2$-pC$_6$H$_4$—CH$_2$—, —CH$_2$-pC$_6$H$_4$—CH$_2$—O—, —CH$_2$—NHCO—, —C$_6$H$_4$—NHCO—, —CH$_2$—O—CH$_2$— and —CH═CH—CH$_2$—NH—(CH$_2$)$_2$—.

It is noted herein that in some embodiments, for the sake of clarity and simplicity of presentation, the spacer moiety Y may be defined as including the C5" carbon atom of the aminoglycoside-based antimicrobial agent moiety in cases such as when Y is an amide —NHCO—, and the carbon atom of the amide group is the C5" atom. Similarly, the spacer moiety Y may be defined as not including the oxygen atom of the C5"-O— group of the aminoglycoside-based antimicrobial agent moiety.

The positions at which the first and second spacer moieties are attached to the antimicrobial agents are generally selected such that the attachment or presence of a spacer moiety on the antimicrobial agent does not preclude the antimicrobial activity of the antimicrobial agents substantially. The ability to be modified structurally without substantially losing antimicrobial activity is referred to herein and in the art as "tolerance for structural modifications" of any given antimicrobial agent. Suitable positions depend on the type of antimicrobial agent, hence discussion and exemplary positions are provided herein below.

SAR studies on fluoroquinolones have demonstrated the highest tolerance for structural modifications at the terminal nitrogen of the piperazine ring [7, 9-11, 21, 22].

Scheme 1 presents an optional position at which the first spacer moiety can be attached to a fluoroquinolone type antimicrobial agent, which includes, without limitation, ciprofloxacin, enoxacin, gatifloxacin, grepafloxacin, lomefloxacin, norfloxacin, orbifloxacin, sarafloxacin and temafloxacin. An exemplary suitable attachment site is the terminal nitrogen position at the piperazine moiety, marked by an arrow in Scheme 1.

Scheme 1

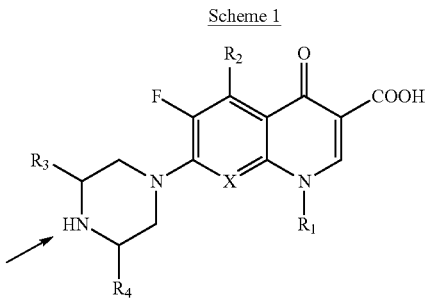

|  | X | R$_1$ | R$_2$ | R$_3$ | R$_4$ |
|---|---|---|---|---|---|
| Ciprofloxacin | CH | cyclopropane | H | H | H |
| Enoxacin | N | Et | H | H | H |
| Gatifloxacin | COCH$_3$ | cyclopropane | H | H | CH$_3$ |
| Grepafloxacin | CH | cyclopropane | CH$_3$ | H | CH$_3$ |
| Lomefloxacin | CF | Et | H | H | CH$_3$ |
| Norfloxacin | CH | Et | H | H | H |
| Orbifloxacin | CF | cyclopropane | F | CH$_3$ | CH$_3$ |
| Sarafloxacin | CH | p-fluorobenzene | H | H | H |
| Temafloxacin | CH | 2,4-difluorobenzene | H | H | CH$_3$ |

Hence, according to some embodiments of the present invention, when the non-ribosomal antimicrobial agent of formula I, or the quinolone-based antimicrobial agent of formula III is ciprofloxacin, it is attached to X via the terminal nitrogen of the piperazine moiety thereof. However, other positions on the skeleton or substituents of ciprofloxacin to which a spacer moiety, if present, is attached are also contemplated.

Several SAR studies on aminoglycosides have demonstrated a high tolerance for structural modifications at different positions. For 4,5-disubstituted 2-deoxystrepamine family of aminoglycosides the positions that were identified for such modifications were C5"-position [13, 14], C2"-position [23-26] and N1 position [25]. For 4,6-disubstituted 2-deoxystrepamine family of aminoglycosides, however, substantial tolerance for structural variations was observed at position C1-NH—[27, 28].

As mentioned in the background section, the present inventors have previously disclosed that some structural positions on the skeleton of known aminoglycosides are more suitable for chemical modifications, meaning that appending chemical moieties at these positions does not abolish or preclude the antimicrobial activity thereof.

Scheme 2 presents the optional positions at which the second spacer moiety can be attached to a 4,5-disubstituted-2-deoxistreptamine type aminoglycoside, which include neomycin B, ribostamycin and paromomycin. Exemplary suitable attachment sites, marked by arrows in Scheme 2, include the C5"-position, the C2"-position and the C1-NH— position.

Scheme 2

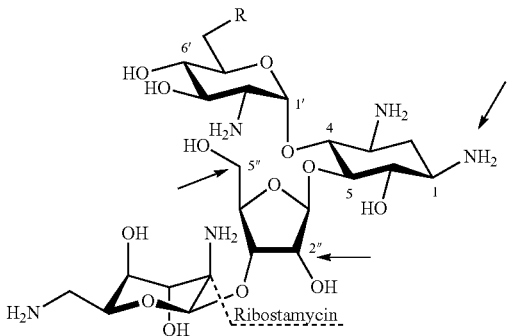

|  | R |
|---|---|
| Ribostamycin | $NH_2$ |
| Neomycin B | $NH_2$ |
| Paromomycin | OH |

Scheme 3 presents the optional position at which the second spacer moiety can be attached to a 4,6-disubstituted-2-deoxistreptamine type aminoglycoside, which include kanamycin A and B, tobramycin and dibekacin. An exemplary suitable attachment site is the C1-NH— position, marked by an arrow in Scheme 3.

Scheme 3

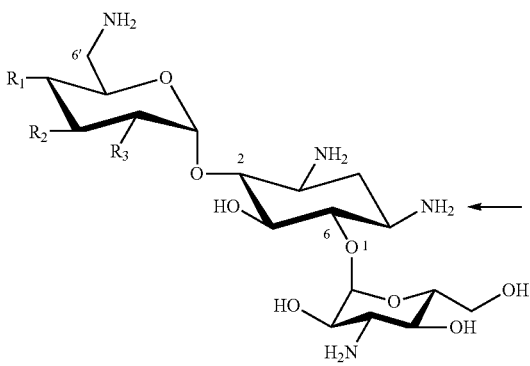

|  | $R_1$ | $R_2$ | $R_3$ |
|---|---|---|---|
| Kanamycin A | OH | OH | OH |
| Kanamycin B | OH | OH | $NH_2$ |
| Tobramycin | OH | H | $NH_2$ |
| Dibekacin | H | H | $NH_2$ |

Following similar guidelines and rational, other positions on similar or other aminoglycosides and non-ribosomal active antimicrobial agents can be identified and used to construct the conjugates, according to embodiments of the present invention.

According to some embodiments of the present invention, when the aminoglycoside-based antimicrobial agent is neomycin B, it is covalently bound to Y via the C5"-position thereof, and when the aminoglycoside-based antimicrobial agent is kanamycin A, it is covalently bound to Y via the C1-N-position thereof.

In the context of the present embodiments, the spacer moieties, when present, connect between the antimicrobial agent moieties and the linking moiety. As used herein, the phrase "linking moiety" describes a chemical moiety that links two other chemical moieties via one or more covalent bonds. In general, the linking moiety can be formed during a chemical reaction, such that by reacting two or more reactive groups, the linking moiety is formed as a new chemical entity which can comprise a bond (between two atoms), or one or more bonded atoms. Alternatively, the linking moiety can be an independent chemical moiety comprising two or more reactive groups to which the reactive groups of other compounds can be attached, either directly or indirectly, as is detailed hereinunder.

Herein throughout, the phrase "end group" describes a group (a substituent) that is attached to another moiety in the compound via one atom thereof; and the phrase "linking moiety" describes a group that is attached to two other moieties via two or more atoms therein.

Exemplary linking moieties, according to some embodiments of the present invention, include without limitation, amide, lactone, lactam, carboxylate, cycloalkene, cyclohexene, heteroalicyclic, heteroaryl, triazine, triazole, disulfide, imine, aldimine, ketimine, hydrazone, semicarbazone and the likes. Other linking moieties are defined hereinbelow.

The phrase "covalent bond", as used herein, refers to one or more pairs of electrons which are shared between atoms in a form of chemical bonding.

The term "amide" describes a —NR'—C(=O)—R" or a —C(=O)—NR'R" end groups or a —NR'—C(=O)— linking moiety, where each of R' and R" is independently hydrogen, alkyl, cycloalkyl, heteroalicyclic, aryl or heteroaryl, as these terms are defined herein.

The term "carboxylate" or "ester", as used herein, refers to a —C(=O)—O—R' end group, where R' is as defined herein, or a —C(=O)—O— linking moiety.

The term "triazine" refers to a heterocyclic ring, analogous to the six-membered benzene ring but with three carbons replaced by nitrogen atoms. The three isomers of triazine are distinguished from each other by the positions of their nitrogen atoms, and are referred to as 1,2,3-triazine, 1,2,4-triazine, and 1,3,5-triazine. Other aromatic nitrogen heterocycles include pyridines with 1 ring nitrogen atom, diazines with 2 nitrogen atoms in the ring and tetrazines with 4 ring nitrogen atoms.

The term "triazole" refers to either one of a pair of isomeric chemical compounds with molecular formula $C_2H_3N_3$, having a five-membered ring of two carbon atoms and three nitrogen atoms, namely 1,2,3-triazoles and 1,2,4-triazoles.

The term "disulfide" refers to a —S—S— linking moiety.

The term "imine", which is also referred to in the art interchangeably as "Schiff-base", describes a —N=CR'— linking moiety, with R' as defined herein or hydrogen. As is well known in the art, Schiff bases are typically formed by reacting an aldehyde or a ketone and an amine-containing moiety such as amine, hydrazine, hydrazide and the like, as these terms are defined herein. The term "aldimine" refers to a —CH=N— imine which is derived from an aldehyde. The term "ketimine" refers to a —CR'=N— imine which is derived from a ketone.

The term "hydrazone" refers to a —R'C=N—NR"— linking moiety, wherein R' and R" are as defined herein.

The term "semicarbazone" refers to a linking moiety which forms in a condensation reaction between an aldehyde or ketone and semicarbazide. A semicarbazone linking moiety stemming from a ketone is a —R'C=NNR"C(=O)NR'"—, and a linking moiety stemming from an aldehyde is a —CR'=NNR"C(=O)NR'"—, wherein R' and R" are as defined herein and R'" or as defined for R'.

As used herein, the term "lactone" refers to a cyclic ester, namely the intra-condensation product of an alcohol group —OH and a carboxylic acid group —COOH in the same molecule.

As used herein, the term "lactam" refers to a cyclic amide, as this term is defined herein. A lactam with two carbon atoms beside the carbonyl and four ring atoms in total is referred to as a β-lactam, a lactam with three carbon atoms beside the carbonyl and five ring atoms in total is referred to as a γ-lactam, a lactam with four carbon atoms beside the carbonyl and six ring atoms in total is referred to as a δ-lactam, and so on.

According to some embodiments of the present invention, the linking moiety, denoted D in formula I and W in formula III, is a triazole having the general formula II:

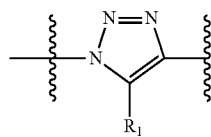

Formula II wherein each of the wiggled lines denote covalent bond to either A-X, A'-X or B—Y, and $R_1$ is selected from the group consisting of hydrogen, alkyl, cycloalkyl, and alkenyl, each of which can be branched, unbranched, substituted or unsubstituted. According to some embodiments of the present invention, $R_1$ is hydrogen, alkyl, aryl or cycloalkyl, as these are defined herein. According to some embodiments, $R_1$ is hydrogen.

A linking group having Formula II hereinabove can be a result of a reaction between two reactive groups, alkynyl and azide, which reaction is referred to herein and in the art as "click chemistry" or "click reaction", as discussed hereinbelow and demonstrated in the Examples section that follows.

Other linking groups can also be a result of a reaction between two reactive groups, as further detailed hereinbelow.

Alternatively, a desired linking group is first generated and the antimicrobial agents and/or spacer moieties are attached thereto.

According to some embodiments of the present invention, the linking moiety (e.g., D in Formula I or W in Formula III) is stable at physiological conditions, namely the linking moiety of the conjugate does not disintegrate for the duration of exposure to the physiological environment in the subject's body. Such linking moiety is referred to herein a "biostable". Biostable linking moieties offer the advantage of an extended time period at which the conjugate can exert its antimicrobial activity when the agents comprising the conjugate are conjugated, up to the time it is secreted or otherwise removed from the infected system or body. An exemplary biostable linking moiety is a triazole-based linking moiety.

According to some embodiments of the present invention, the linking moiety is a biocleavable linking moiety. Representative examples of biocleavable moieties include, without limitation, amides, carboxylates, carbamates, phosphates, hydrazides, thiohydrazides, disulfides, epoxides, peroxo and methyleneamines. Such moieties are typically subjected to enzymatic cleavages in a biological system, by enzymes such as, for example, hydrolases, amidases, kinases, peptidases, phospholipases, lipases, proteases, esterases, epoxide hydrolases, nitrilases, glycosidases and the like.

As used herein, the phrase "biocleavable moiety" describes a chemical moiety, which undergoes cleavage in a biological system such as, for example, the digestive system of an organism or a metabolic system in a living cell.

The rational behind having a biocleavable linking moiety in a conjugate according to some embodiments of the present invention, stems from the assumption that under a particular dosing regime, the conjugate administered in each dose would exert its antimicrobial activity within a certain timeframe, and thereafter be degraded to sub-components by the subject's metabolic systems, thereby rendering it easier for the subject's secretion system to be rid thereof.

The conjugates presented herein, according to some embodiments of the present invention, can be formed from neomycin B or kanamycin A, and ciprofloxacin. Exemplary conjugates, according to some embodiments of the present invention, have been prepared, as presented and demonstrated in the Examples section below for neomycin B (Table 1 below), and for kanamycin A (Table 2 below).

TABLE 1

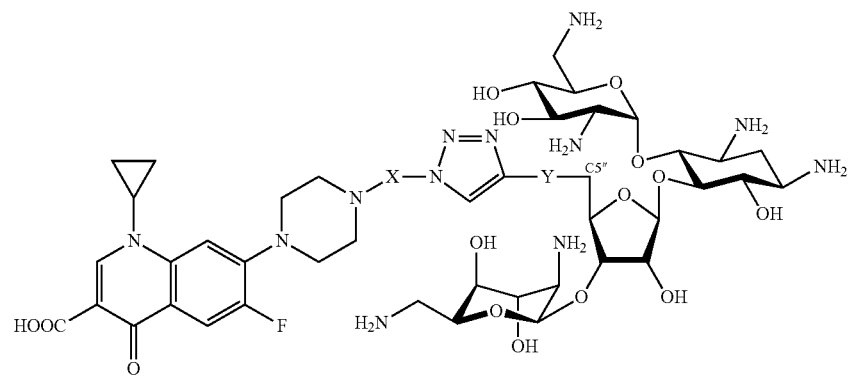

| Conjugate | Full chemical name | X | Y |
|---|---|---|---|
| Compound 1a | N-(4-(1-(2-(ciprofloxacin)ethyl)-1H-1,2,3-triazol-4-yl)-5"-phenyl)neomycin | —(CH$_2$)$_2$— | —C$_6$H$_4$—NHCO— |
| Compound 1b | N-(4-(1-(2-(ciprofloxacin)propyl)-1H-1,2,3-triazol-4-yl)-5"-phenyl)neomycin carboxamide | —(CH$_2$)$_3$— | —C$_6$H$_4$—NHCO— |

TABLE 1-continued

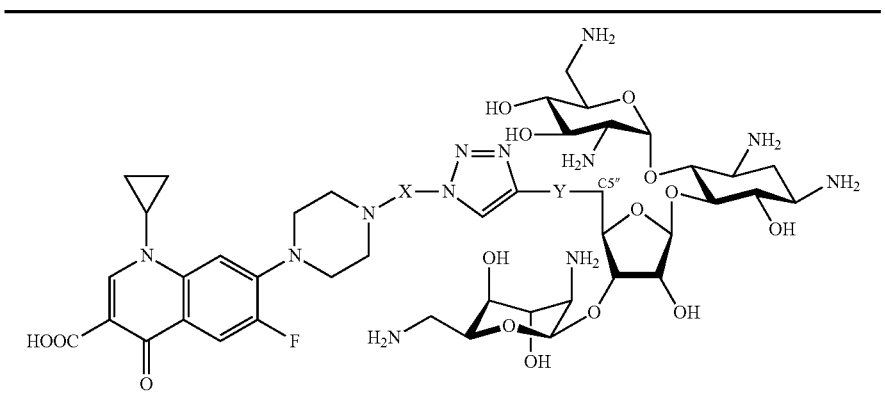

| Conjugate | Full chemical name | X | Y |
|---|---|---|---|
| Compound 1c | N-(4-(1-(2-(ciprofloxacin)butyl)-1H-1,2,3-triazol-4-yl)-5"-phenyl)neomycin carboxamide | —(CH$_2$)$_4$— | —C$_6$H$_4$—NHCO— |
| Compound 1d | N-(4-(1-(2-(ciprofloxacin)pentyl)-1H-1,2,3-triazol-4-yl)-5"-phenyl)neomycin carboxamide | —(CH$_2$)$_5$— | —C$_6$H$_4$—NHCO— |
| Compound 1e | N-(4-(1-(2-(ciprofloxacin)hexyl)-1H-1,2,3-triazol-4-yl)-5"-phenyl)neomycin carboxamide | —(CH$_2$)$_6$— | —C$_6$H$_4$—NHCO— |
| Compound 1f | N-(4-(1-(2-hydroxy-3-(ciprofloxacin)propyl)-1H-1,2,3-triazol-4-yl)-5"-phenyl)neomycin carboxamide | —CH$_2$CH(OH)CH$_2$— | —C$_6$H$_4$—NHCO— |
| Compound 1g | N-(4-(1-(2-(2-(ciprofloxacin)ethoxy)ethyl)-1H-1,2,3-triazol-4-yl)-5"-phenyl)neomycin carboxamide | —(CH$_2$)$_2$—O—(CH$_2$)$_2$— | —C$_6$H$_4$—NHCO— |
| Compound 1h | N-(4-(1-(4-((ciprofloxacin)methyl)benzyl)-1H-1,2,3-triazol-4-yl)-5"-phenyl)neomycin carboxamide | —CH$_2$—$m$C$_6$H$_4$—CH$_2$— | —C$_6$H$_4$—NHCO— |
| Compound 1i | N-(4-(1-(3-((ciprofloxacin)methyl)benzyl)-1H-1,2,3-triazol-4-yl)-5"-phenyl)neomycin carboxamide | —CH$_2$—$p$C$_6$H$_4$—CH$_2$— | —C$_6$H$_4$—NHCO— |
| Compound 1j | N-((1-(4-(ciprofloxacin)ethyl)-1H-1,2,3-triazol-4-yl)-5"-methyl)neomycin carboxamide | —(CH$_2$)$_2$— | —CH$_2$—NHCO— |
| Compound 1k | N-((1-(4-(ciprofloxacin)propyl)-1H-1,2,3-triazol-4-yl)-5"-methyl)neomycin carboxamide | —(CH$_2$)$_3$— | —CH$_2$—NHCO— |
| Compound 1l | N-((1-(4-(ciprofloxacin)pentyl)-1H-1,2,3-triazol-4-yl)-5"-methyl)neomycin carboxamide | —(CH$_2$)$_5$— | —CH$_2$—NHCO— |
| Compound 1m | N-((1-(2-hydroxy-3-(ciprofloxacin)propyl)-1H-1,2,3-triazol-4-yl)-5"-methyl)neomycin carboxamide | —CH$_2$CH(OH)CH$_2$— | —CH$_2$—NHCO— |
| Compound 1n | N-((1-(2-(2-(ciprofloxacin)ethoxy)ethyl)-1H-1,2,3-triazol-4-yl)-5"-methyl)neomycin carboxamide | —(CH$_2$)$_2$—O—(CH$_2$)$_2$— | —CH$_2$—NHCO— |
| Compound 1o | N-((1-(3-((ciprofloxacin)methyl)benzyl)-1H-1,2,3-triazol-4-yl)-5"-methyl)neomycin carboxamide | —CH$_2$—$m$C$_6$H$_4$—CH$_2$— | —CH$_2$—NHCO— |
| Compound 1p | N-((1-(4-((ciprofloxacin)methyl)benzyl)-1H-1,2,3-triazol-4-yl)-5"-methyl)neomycin carboxamide | —CH$_2$—$p$C$_6$H$_4$—CH$_2$— | —CH$_2$—NHCO— |
| Compound 1q | 4-((5"-neomycin methoxy)methyl)-1-(2-(ciprofloxacin)ethyl)-1H-1,2,3-triazole | —(CH$_2$)$_2$— | —CH$_2$—O— |

As noted hereinabove, in the case of exemplary conjugates Compounds 1a-p, the carbon atom of the amide group denoted as spacer moiety Y is the C5" carbon of the aminoglycoside moiety, and the oxygen atom in the exemplary conjugate Compound 1q can also be regarded, at least from the synthesis aspect, as the C5"-O— oxygen.

TABLE 2

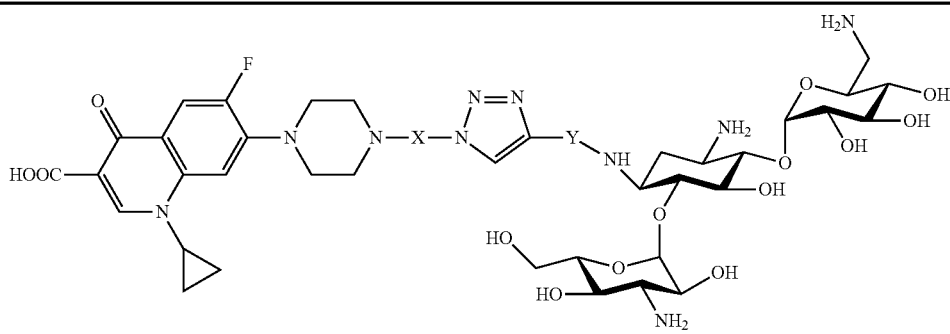

| Conjugate | Full chemical name | X | Y |
|---|---|---|---|
| Compound 11a | 4-(1-N-kanamycin methyl)-1-(2-(ciprofloxacin)ethyl)-1H-1,2,3-triazole | —(CH$_2$)$_2$— | —CH$_2$— |
| Compound 11f | 1-(4-(1-N-kanamycin methyl)-1H-1,2,3-triazol-1-yl)-3-(ciprofloxacin)propan-2-ol | —CH$_2$CH(OH)CH$_2$— | —CH$_2$— |
| Compound 11i | 4-(1-N-kanamycin methyl)-1-(4-((ciprofloxacin)methyl)benzyl)-1H-1,2,3-triazole | —CH$_2$—$p$C$_6$H$_4$—CH$_2$— | —CH$_2$— |

According to some embodiments of the present invention, other conjugates can be prepared following the general procedures presented in the Examples section below and following the general processes for preparing the conjugates, as follows.

Hence, according to another aspect of the present invention, there is provided a process of preparing the conjugates presented herein under formula I. The process is effected by reacting a compound having the general formula IV:

A-X—RG$_1$  Formula IV wherein:
A is a non-ribosomal-active antimicrobial agent moiety;
X is a first spacer moiety, covalently bound to A, or absent; and
RG$_1$ is a first reactive group;
with a compound having the general formula V:

RG$_2$-Y—B  Formula V

B is an aminoglycoside-based antimicrobial agent moiety;
Y is a second spacer moiety, covalently bound to B, or absent; and
RG$_2$ is a second reactive group.

According to yet another aspect of the present invention, there is provided a process of preparing the conjugates presented herein under formula III, which is effected by reacting a compound having the general formula VI:

A'-X—RG$_1$'  Formula VI wherein:
A' is a quinolone-based antimicrobial agent moiety;
X is a first spacer moiety, covalently bound to A, or absent; and
RG$_1$' is a first reactive group;
with a compound having the general formula VII:

RG$_2$'-Y—B  Formula VII

B is an aminoglycoside-based antimicrobial agent moiety;
Y is a second spacer moiety, covalently bound to B, or absent; and
RG$_2$' is a second reactive group.

A reactive group (RG) in each of the antimicrobial agent derivatives that forms the conjugate presented herein, namely A-X— and B—Y—, serves for covalently binding the antimicrobial agents to one another, so as to form the conjugate. The reactive groups, referred to herein as RG$_1$ (attached to antimicrobial agent derivative A-X—) and RG$_2$ (attached to antimicrobial agent derivative B—Y—) may form a part of the antimicrobial agent in cases where X and/or Y are absent, or be present substantially at the end of each of the spacer moieties X and/or Y which are attached to the antimicrobial agents.

The phrase "reactive group", as used herein, refers to a chemical group that is capable of undergoing a chemical reaction that typically leads to the formation a covalent bond. Chemical reactions that lead to a bond formation include, for example, cycloaddition reactions (such as the Diels-Alder's reaction, the 1,3-dipolar cycloaddition Huisgen reaction, and the similar "click reaction"), condensations, nucleophilic and electrophilic addition reactions, nucleophilic and electrophilic substitutions, addition and elimination reactions, alkylation reactions, rearrangement reactions and any other known organic reactions that involve a reactive group.

Representative examples of reactive groups include, without limitation, acyl halide, aldehyde, alkoxy, alkyne, amide, amine, aryloxy, azide, aziridine, azo, carbamate, carbonyl, carboxyl, carboxylate, cyano, diene, dienophile, epoxy, guanidine, guanyl, halide, hydrazide, hydrazine, hydroxy, hydroxylamine, imino, isocyanate, nitro, phosphate, phosphonate, sulfinyl, sulfonamide, sulfonate, thioalkoxy, thioaryloxy, thiocarbamate, thiocarbonyl, thiohydroxy, thiourea and urea, as these terms are defined hereinafter.

As used herein, the term "aldehyde" refers to an —C(=O)—H group.

The term "hydroxy" as used herein describes an —OH group.

The terms "thio", "sulfhydryl" or "thiohydroxy" as used herein describe an —SH group.

The term "disulfide" as used herein describes an —S—S— linking moiety.

The term "alkoxy" as used herein describes an —O-alkyl, an —O-cycloalkyl, as defined hereinabove. The ether group —O— is also a possible linking moiety.

The term "aryloxy" as used herein describes an —O-aryl group.

The term "thioalkoxy" as used herein describes an —S-alkyl group. The thioether group —S— is also a possible linking moiety.

The term "thioaryloxy" as used herein describes an —S-aryl group. The thioarylether group —S-aryl- is also a possible linking moiety.

As used herein, the term "amine" refers to an —NR'R" group where R' and R" are each hydrogen, alkyl, alkenyl, cycloalkyl, aryl, heteroaryl (bonded through a ring carbon) or heteroalicyclic (bonded through a ring carbon) as defined hereinbelow.

The terms "halide" or "halo" refer to fluorine, chlorine, bromine or iodine.

As used herein, the term "azide" refers to a —$N_3$ (—N=$N^+$=$N^-$) group

The term "aziridine", as used herein, refers to a reactive group which is a three membered heterocycle with one amine group and two methylene groups, having a molecular formula of —$C_2H_3NH$.

The term "diene", as used herein, refers to a —CR'=CR"—CR'"=CR""— group, wherein R' as defined hereinabove, and R", R'" and R"" are as defined for R'.

The term "dienophile", as used herein, refers to a reactive group that reacts with a diene, typically in a Diels-Alder reaction mechanism, hence a dienophile is typically a double bond or an alkenyl.

The term "epoxy", as used herein, refers to a reactive group which is a three membered heterocycle with one oxygen and two methylene groups, having a molecular formula of —$C_2H_3O$.

The term "azo" or "diazo" describes an —N=NR' reactive group or an —N=N— linking moiety, as these phrases are defined hereinabove, with R' as defined hereinabove.

The term "carbamate" refers to a —NR'(C=O)OH (carbamic acid) end or reactive group, or a —NR'(C=O)O— linking moiety, with R' as defined hereinabove.

The term "thiocarbamate" refers to a —NR'(C=S)OH end or reactive group, or a —NR'(C=S)O— linking moiety, with R' as defined hereinabove.

The term "carbonyl" refers to a —(C=O)— group.

The term "thiocarbonyl" refers to a —(C=S)— group.

As used herein, the term "carboxyl" refers to an —C(=O)OH group.

The term "cyano" describes a —C≡N group.

The term "isocyanate" describes an —N=C=O group.

The term "hydrazide", as used herein, refers to a —C(=O)—NR'—NR"R'" group wherein R', R" and R'" are each independently hydrogen, alkyl, cycloalkyl or aryl, as these terms are defined herein.

As used herein, the term "hydrazine" describes a —NR'—NR"R'" group, wherein R', R" and R'" are each independently hydrogen, alkyl, cycloalkyl or aryl, as these terms are defined herein.

The term "hydroxylamine", as used hereon, refers to either a —NHOH group or a —$ONH_2$.

The term "nitro" describes an —$NO_2$ group.

The term "acyl halide" describes a —(C=O)R"" group wherein R"" is halide, as defined hereinabove.

The term "phosphate" describes an —O—P(=O)$_2$(OR') end or reactive group or a —O—P(=O)$_2$(O)— linking moiety, as these phrases are defined hereinabove, with R' as defined herein.

The term "phosphonate" describes a —P(=O)(OR')(OR") end or reactive group or a —P(=O)(OR')(O)— linking moiety, as these phrases are defined hereinabove, with R' and R" as defined herein.

The term "sulfoxide" or "sulfinyl" describes a —S(=O)R' end or reactive group or an —S(=O)— linking moiety, as these phrases are defined hereinabove, where R' is as defined hereinabove.

The term "sulfonamide" encompasses the term "S-sulfonamide" which describes a —S(=O)$_2$—NR'R" end or reactive group or a —S(=O)$_2$—NR'— linking moiety, as these phrases are defined hereinabove, with R' and R" as defined herein; and the term "N-sulfonamide" which describes an R'S(=O)$_2$—NR"— end or reactive group or a —S(=O)$_2$—NR'— linking moiety, as these phrases are defined hereinabove, where R' and R" are as defined herein.

The term "sulfonate" describes a —S(=O)$_2$—R' end or reactive group or an —S(=O)$_2$— linking moiety, as these phrases are defined hereinabove, where R' is as defined herein.

According to some embodiments of the present invention, the linking moiety is formed as a result of a bond-forming reaction between two reactive groups, namely $RG_1$ and RG2, which can be present in either sides of the conjugate's moieties before these are reacted together to form the conjugate. For example, a reaction between a diene reactive group and a dienophile reactive group, e.g. a Diels-Alder reaction, would form a cycloalkene linking moiety, and in most cases a cyclohexene linking moiety. In another example, an amine reactive group would form an amide linking moiety when reacted with a carboxyl reactive group. In another example, a hydroxyl reactive group would form an ester linking moiety when reacted with a carboxyl reactive group. In another example, a sulfhydryl reactive group would form a disulfide (—S—S—) linking moiety when reacted with another sulfhydryl reactive group under oxidation conditions, or a thioether (thioalkoxy) linking moiety when reacted with a halo reactive group or another leaving-reactive group. In another example, an alkynyl reactive group would form a triazole linking moiety by "click reaction" when reacted with an azide reactive group.

The "click reaction", also known as "click chemistry" is a name used to describe a Cu(I)-catalyzed stepwise variant of the Huisgen 1,3-dipolar cycloaddition of azides and alkynes to yield 1,2,3-triazole. This reaction is carried out under ambient conditions, or under mild microwave irradiation, and with exclusive regioselectivity for the 1,4-disubstituted triazole product when mediated by catalytic amounts of Cu(I) salts [V. Rostovtsev, L. G. Green, V. V. Fokin, K. B. Sharpless, *Angew. Chem. Int. Ed.* 2002, 41, 2596; H. C. Kolb, M. Finn, K. B. Sharpless, *Angew Chem., Int. Ed.* 2001, 40, 2004].

As demonstrated in the Examples section that follows, the "click reaction" is particularly suitable to form the conjugates presented herein since it is carried out under conditions which are non-distructive to the antimicrobial agent moieties, according to some embodiments of the present invention, and it affords the conjugates at high chemical yields using mild conditions in aqueous media. The selectivity of this reaction allows to perform the conjugation with minimized or nullified use of protecting groups, which use often results in multistep cumbersome synthetic processes.

Hence, when D and W of formulae I and III respectively are having the structure represented in formula II, namely a 4-yl-1-yl-1,2,3-triazole, one of $RG_1$ or $RG_2$ of formulae IV and V respectively, or $RG_1$' or $RG_2$' of formulae VI and VII respectively, is alkynyl and the other is azide. When the process used for preparing the conjugates is based on the "click chemistry", the reaction is effected in the presence of a copper catalyst.

Alternatively, $RG_1$' or $RG_2$' of formulae VI and VII respectively are selected such that other linking moieties can be formed from their inter-reaction. According to some embodiments of the present invention, a strong nucleophile (including but not limited to, hydrazine, hydrazide, hydroxylamine (aminooxy, —O—$NH_2$), semicarbazide), present as a terminal group in one of the antimicrobial agent derivatives, can be reacted with an aldehyde or ketone group present in the other antimicrobial agent derivative to form an imine, a hydrazone, an oxime or a semicarbazone, as applicable, which in some cases can be further reduced by treatment with an appropriate reducing agent. In such embodiments, one of $RG_1'$ or $RG_2'$ can be a nucleophile group (Nu), and the other can be a leaving group (L), and their inter-reaction would form a conjugate according to Scheme 4 below.

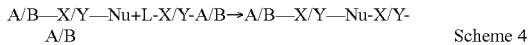

Scheme 4

As shown in Scheme 4, one of the antimicrobial agent derivatives has the formula A/B—X/Y—Nu and the other antimicrobial agent derivative has the formula L-X/Y-A/B, and the resulting linking moiety is formed essentially from the nucleophile group.

Examples of nucleophile groups include, but are not limited to, amine, alkoxy, aryloxy, sulfhydryl, imino, carboxylate, hydrazide, aminooxy groups that would react primarily via a SN2-type mechanism. Additional examples of nucleophile groups include those functional groups that would react primarily via a nucleophilic addition reaction. Examples of leaving groups include chloride, bromide, iodide, mesylate, tresylate, and tosylate and other groups expected to undergo nucleophilic displacement as well as ketones, aldehydes, thioesters, olefins, alpha-beta unsaturated carbonyl groups, carbonates and other electrophilic groups expected to undergo addition by nucleophiles.

Hence, in some embodiments of the present invention, one of the antimicrobial agent derivatives A-X or B—Y includes a terminal carbonyl-containing reactive group (aldehyde or ketone), and the other antimicrobial agent derivative contains a terminal hydrazine, hydroxylamine, hydrazide or semicarbazide reactive group.

In some embodiments, the hydroxylamine-terminal antimicrobial agent derivative will have the structure A/B—X/Y—O—$NH_2$.

In some embodiments, the hydrazine- or hydrazide-containing antimicrobial agent derivative will have the structure A/B—X/Y—(C═O)—NH—$NH_2$ where (C═O) is optionally a carbonyl group that can be present or absent.

In some embodiments, the semicarbazide-containing antimicrobial agent derivative will have the structure A/B—X/Y—NH—(C═O)—NH—$NH_2$.

The particular chemistry which defines the linking moiety is selected considering the same aspects used for selecting the spacer moieties, namely the effect it has on the synthesis and the effect it has on the biological activity of the resulting conjugate, with emphasis on the former. The nature of the reactive groups with form the linking moiety should be selected in such a way so as to minimize the required protection and deprotection steps, aimed at preventing side-reactions at various undesired positions on both sides of the conjugate. For example, an amide linking moiety is simple to form between an amine and a carboxyl groups, however the synthetic process would require specific protection of such groups on the antimicrobial agent moieties, particularly amines on the aminoglycoside moiety.

As demonstrated in the Examples section that follows, the conjugates according to some embodiments of the present invention are highly effective in treating medical conditions associated with a pathogenic microorganism in a subject.

The conjugates presented herein are also highly effective in treating medical conditions associated with pathogenic microorganisms which have already developed resistance to any antibiotic agent. The conjugates presented herein are particularly effective in fighting pathogenic microorganisms since they suppress the emergence of resistance thereto.

The phrases "effective in treating medical conditions associated with pathogenic microorganisms", "effective in treating a subject diagnosed with a medical conditions associated with pathogenic microorganisms" and/or "identified for use in the treatment of a medical condition associated with a pathogenic microorganism in a subject", as used herein, refer to characteristics of a substance, such as the conjugates according to some embodiments of the present invention, that can effect death, killing, eradication, elimination, reduction in number, reduction of growth rate, reduction of a load, and a change in population distribution of one or more species of pathogenic microorganisms, as well as effecting a reduction or prevention of the emergence of resistance of such microorganisms to the substance.

Herein throughout, the phrase "pathogenic microorganism" is used to describe any microorganism which can cause a disease or disorder in a higher organism, such as mammals in general and a human in particular. The pathogenic microorganism may belong to any family of organisms such as, but not limited to prokaryotic organisms, *eubacterium*, archaebacterium, eukaryotic organisms, yeast, fungi, algae, protozoan, and other parasites.

Non-limiting examples of pathogenic microorganism include *Plasmodium falciparum* and related malaria-causing protozoan parasites, *Acanthamoeba* and other free-living amoebae, *Aeromonas hydrophila*, *Anisakis* and related worms, and further include, but not limited to *Acinetobacter baumanii, Ascaris lumbricoides, Bacillus cereus, Brevundimonas diminuta, Campylobacter jejuni, Clostridium botulinum, Clostridium perfringens, Cryptosporidium parvum, Cyclospora cayetanensis, Diphyllobothrium, Entamoeba histolytica*, certain strains of *Escherichia coli, Eustrongylides, Giardia lamblia, Klebsiella pneumoniae, Listeria monocytogenes, Nanophyetus, Plesiomonas shigelloides, Proteus mirabilis, Pseudomonas aeruginosa, Salmonella, Serratia odorifera, Shigella, Staphylococcus aureus, Stenotrophomonas maltophilia, Streptococcus, Trichuris trichiura, Vibrio cholerae, Vibrio parahaemolyticus, Vibrio vulnificus* and other vibrios, *Yersinia enterocolitica, Yersinia pseudotuberculosis* and *Yersinia kristensenii*.

Other pathogens include *Strep. pyogenes* (Group A), *Strep. pneumoniae, Strep.* GpB, *Strep. viridans, Strep.* GpD (*Enterococcus*), *Strep.* GpC and GpG, *Staph. aureus, Staph. epidermidis, Bacillus subtilis, Bacillus anthracis, Listeria monocytogenes, Anaerobic cocci, Clostridium* spp., *Actinomyces* spp, *Escherichia coli, Enterobacter aerogenes, Kiebsiella pneumoniae, Proteus mirabilis, Proteus vulgaris, Morganella morganii, Providencia stuartii, Serratia marcescens, Citrobacter freundii, Salmonella typhi, Salmonella paratyphi, Salmonella typhi murium, Salmonella virchow, Shigella* spp., *Yersinia enterocolitica, Acinetobacter calcoaceticus, Flavobacterium* spp., *Haemophilus influenzae, Pseudomonas aeruginosa, Campylobacter jejuni, Vibrio parahaemolyticus, Brucella* spp., *Neisseria meningitidis, Neisseria gonorrhoea, Bacteroides fragilis, Fusobacterium* spp., *Mycobacterium tuberculosis* (including MDR and XDR strains from hospital origins isolated from patients) and *Mycobaterium smegmatis*.

Accordingly, a condition associated with a pathogenic microorganism describes an infectious condition that results from the presence of the microorganism in a subject. The infectious condition can be, for example, a bacterial infection, a fungal infection, a protozoal infection, and the like.

Some higher forms of microorganisms are pathogenic per se, and other harbor lower forms of pathogenic bacteria, thus present a medical threat expressed in many medical conditions, such as, without limitation, actinomycosis, anthrax, aspergillosis, bacteremia, bacterial skin diseases, *bartonella* infections, botulism, brucellosis, *burkholderia* infections, campylobacter infections, candidiasis, cat-scratch disease, chlamydia infections, cholera, clostridium infections, coccidioidomycosis, cryptococcosis, dermatomycoses, dermatomycoses, diphtheria, ehrlichiosis, epidemic louse borne typhus, Escherichia coli infections, fusobacterium infections, gangrene, general infections, general mycoses, gram-negative bacterial infections, Gram-positive bacterial infections, histoplasmosis, impetigo, klebsiella infections, legionellosis, leprosy, leptospirosis, listeria infections, lyme disease, maduromycosis, melioidosis, mycobacterium infections, mycoplasma infections, necrotizing fasciitis, nocardia infections, onychomycosis, ornithosis, pneumococcal infections, pneumonia, pseudomonas infections, Q fever, rat-bite fever, relapsing fever, rheumatic fever, rickettsia infections, Rocky-mountain spotted fever, salmonella infections, scarlet fever, scrub typhus, sepsis, sexually transmitted bacterial diseases, staphylococcal infections, streptococcal infections, surgical site infection, tetanus, tick-borne diseases, tuberculosis, tularemia, typhoid fever, urinary tract infection, vibrio infections, yaws, yersinia infections, Yersinia pestis plague, zoonoses and zygomycosis.

The conjugates presented herein can be effectively used against bacterial strains which have developed or are prone to or capable of developing resistance to at least one antimicrobial agent. Non-limiting examples of such bacterial strains include:

(a) Gram-positive bacteria such as Strep. pyogenes (Group A), Strep. pneumoniae, Strep. GpB, Strep. viridans, Strep. GpD-(Enterococcus), Strep. GpC and GpG, Staph. aureus, Staph. epidermidis, Bacillus subtilis, Bacillus anthraxis, Listeria monocytogenes, Anaerobic cocci, Clostridium spp., and Actinomyces spp; and (b) Gram-negative bacteria such as Escherichia coli, Enterobacter aerogenes, Kiebsiella pneumoniae, Proteus mirabilis, Proteus vulgaris, Morganella morganii, Providencia stuartii, Serratia marcescens, Citrobacter freundii, Salmonella typhi, Salmonella paratyphi, Salmonella typhi murium, Salmonella virchow, Shigella spp., Yersinia enterocolitica, Acinetobacter calcoaceticus, Flavobacterium spp., Haemophilus influenzae, Pseudomonas aueroginosa, Campylobacter jejuni, Vibrio parahaemolyticus, Brucella spp., Neisseria meningitidis, Neisseria gonorrhoea, Bacteroides fragilis, and Fusobacterium spp.

According to some embodiments of the present invention, the conjugates presented herein can be effectively used against bacterial strains which have developed or are prone to or capable of developing resistance to at least one antimicrobial agent, such as, but not limited to, E. coli R477-100, E. coli ATCC 25922, E. coli AG100B, AG100A, B. subtilis ATCC 6633, MRSA ATCC 43300 and E. coli ATCC 35218.

Thus, according to one aspect of the present invention there is provided a method of treating a medical condition associated with a pathogenic microorganism in a subject. The method is effected by administering to that subject, a therapeutically effective amount of a conjugate as presented herein.

As used herein, the phrase "therapeutically effective amount" describes an amount of an active agent being administered, which will relieve to some extent one or more of the symptoms of the condition being treated. In the context of the present embodiments, the phrase "therapeutically effective amount" describes an amount of a conjugate being administered and/or re-administered, which will relieve to some extent one or more of the symptoms of the condition being treated by being at a level that is harmful to the target microorganism(s), and cause a disruption to the life-cycle of the target microorganism(s), namely a bactericidal level or otherwise a level that inhibits the microorganism growth or eradicates the microorganism.

The efficacy of any antimicrobial agent, including the conjugates presented herein, is oftentimes referred to in minimal inhibitory concentration units, or MIC units. A MIC is the lowest concentration of an antimicrobial agent, typically measured in micro-molar ($\mu$M) or micrograms per milliliter ($\mu$g/ml) units, which can inhibit the growth of a microorganism after a period of incubation, typically 24 hours. MIC values are used as diagnostic criteria to evaluate resistance of microorganisms to an antimicrobial agent, and for monitoring the activity of an antimicrobial agent in question. MICs are determined by standard laboratory methods, as these are described and demonstrated in the Examples section that follows. Standard laboratory methods typically follow a standard guideline of a reference body such as the Clinical and Laboratory Standards Institute (CLSI), British Society for Antimicrobial Chemotherapy (BSAC) or The European Committee on Antimicrobial Susceptibility Testing (EUCAST). In clinical practice, the minimum inhibitory concentrations are used to determine the amount of antibiotic agent that the subject receives as well as the type of antibiotic agent to be used.

As presented in the Examples section that follows, the conjugates described herein exhibit MIC values in the range of 0.2-20 $\mu$g/ml.

According to another aspect of embodiments of the present invention, each of the conjugates described herein is identified for use in treating a subject diagnosed with a medical condition associated with a pathogenic microorganism.

According to another aspect of embodiments of the present invention, there is provided a use of any of the conjugates described herein as a medicament. In some embodiments, the medicament is for treating a subject diagnosed with a medical condition associated with a pathogenic microorganism.

In any of the methods and uses described herein, the conjugate can be administered as a part of a pharmaceutical composition, which further comprises a pharmaceutical acceptable carrier, as detailed hereinbelow. The carrier is selected suitable to the selected route of administration.

The conjugates presented herein can be administered via any administration route, including, but not limited to, orally, by inhalation, or parenterally, for example, by intravenous drip or intraperitoneal, subcutaneous, intramuscular or intravenous injection, or topically (including ophtalmically, vaginally, rectally, intranasally).

Hence, according to another aspect of embodiments of the invention, there is provided a pharmaceutical composition which comprises, as active ingredients, one or more of the conjugates presented herein and a pharmaceutically acceptable carrier. According to some embodiments, the composition is packaged in a packaging material and identified in print, in or on the packaging material, for use in the treatment of a medical condition associated with a pathogenic microorganism in a subject.

As used herein the phrase "pharmaceutical composition" or the term "medicament" refer to a preparation of the conjugates presented herein, with other chemical components such as pharmaceutically acceptable and suitable carriers and excipients, and optionally with additional active agents, such as an antimicrobial agent. The purpose of a pharmaceutical composition is to facilitate administration of the conjugate to a subject.

Hereinafter, the term "pharmaceutically acceptable carrier" refers to a carrier or a diluent that does not cause significant irritation to an organism and does not abrogate the biological activity and properties of the administered conjugate. Examples, without limitations, of carriers are: propylene glycol, saline, emulsions and mixtures of organic solvents with water, as well as solid (e.g., powdered) and gaseous carriers.

Herein the term "excipient" refers to an inert substance added to a pharmaceutical composition to further facilitate administration of a conjugate. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences" Mack Publishing Co., Easton, Pa., latest edition, which is incorporated herein by reference.

The pharmaceutical composition may be formulated for administration in either one or more of routes depending on whether local or systemic treatment or administration is of choice, and on the area to be treated. Administration may be done orally, by inhalation, or parenterally, for example by intravenous drip or intraperitoneal, subcutaneous, intramuscular or intravenous injection, or topically (including ophtalmically, vaginally, rectally, intranasally).

Formulations for topical administration may include but are not limited to lotions, ointments, gels, creams, suppositories, drops, liquids, sprays and powders. Conventional pharmaceutical carriers, aqueous, powder or oily bases, thickeners and the like may be necessary or desirable.

Compositions for oral administration include powders or granules, suspensions or solutions in water or non-aqueous media, sachets, pills, caplets, capsules or tablets. Thickeners, diluents, flavorings, dispersing aids, emulsifiers or binders may be desirable.

Formulations for parenteral administration may include, but are not limited to, sterile solutions which may also contain buffers, diluents and other suitable additives. Slow release compositions are envisaged for treatment.

The amount of a composition to be administered will, of course, be dependent on the subject being treated, the severity of the affliction, the manner of administration, the judgment of the prescribing physician, etc.

Pharmaceutical compositions for use in accordance with embodiments of the invention thus may be formulated in conventional manner using one or more pharmaceutically acceptable carriers comprising excipients and auxiliaries, which facilitate processing of the conjugates presented herein into preparations which can be used pharmaceutically. Proper formulation is dependent upon the route of administration chosen. Toxicity and therapeutic efficacy of the conjugates presented herein can be determined by standard pharmaceutical procedures in experimental animals, e.g., by determining the $EC_{50}$, the $IC_{50}$ and the $LD_{50}$ (lethal dose causing death in 50% of the tested animals) for a subject combination of antimicrobial agent(s) and polymer(s). The data obtained from these activity assays and animal studies can be used in formulating a range of dosage for use in human.

The dosage may vary depending upon the dosage form employed and the route of administration utilized. The exact formulation, route of administration and dosage can be chosen by the individual physician in view of the patient's condition. (See e.g., Fingl et al., 1975, in "The Pharmacological Basis of Therapeutics", Ch. 1 p. 1). In general, the dosage is related to the efficacy of the active ingredient which, in the context of embodiments of the invention, is related to its minimal inhibitory concentration (MIC) and the particular pharmacokinetics and pharmacology thereof for absorption, distribution, metabolism, excretion and toxicity (ADME-Tox) parameters. The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA (the U.S. Food and Drug Administration) approved kit, which may contain one or more unit dosage forms containing the active ingredient. The pack may, for example, comprise metal or plastic foil, such as, but not limited to a blister pack or a pressurized container (for inhalation). The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions for human or veterinary administration. Such notice, for example, may be of labeling approved by the U.S. Food and Drug Administration for prescription drugs or of an approved product insert. Compositions comprising the conjugates presented herein formulated in a compatible pharmaceutical carrier may also be prepared, placed in an appropriate container, and labeled for treatment of an indicated condition, as is detailed herein.

The present embodiments further encompass any enantiomers, prodrugs, solvates, hydrates and/or pharmaceutically acceptable salts of the conjugates described herein and methods, compositions and uses utilizing enantiomers, prodrugs, solvates, hydrates and/or pharmaceutically acceptable salts of the conjugates described herein.

As used herein, the term "enantiomer" refers to a stereoisomer of a conjugate that is superposable with respect to its counterpart only by a complete inversion/reflection (mirror image) of each other. Enantiomers are said to have "handedness" since they refer to each other like the right and left hand. Enantiomers have identical chemical and physical properties except when present in an environment which by itself has handedness, such as all living systems.

The term "prodrug" refers to an agent, which is converted into the active conjugate (the active parent drug) in vivo. Prodrugs are typically useful for facilitating the administration of the parent drug. They may, for instance, be bioavailable by oral administration whereas the parent drug is not. A prodrug may also have improved solubility as compared with the parent drug in pharmaceutical compositions. Prodrugs are also often used to achieve a sustained release of the active conjugate in vivo. An example, without limitation, of a prodrug would be a conjugate according to some embodiments of the present invention, having one or more carboxylic acid moieties, which is administered as an ester (the "prodrug"). Such a prodrug is hydrolyzed in vivo, to thereby provide the free conjugate (the parent drug). The selected ester may affect both the solubility characteristics and the hydrolysis rate of the prodrug.

The term "solvate" refers to a complex of variable stoichiometry (e.g., di-, tri-, tetra-, penta-, hexa-, and so on), which is formed by a solute (the conjugates described herein) and a solvent, whereby the solvent does not interfere with the biological activity of the solute. Suitable solvents include, for example, ethanol, acetic acid and the like.

The term "hydrate" refers to a solvate, as defined hereinabove, where the solvent is water.

The phrase "pharmaceutically acceptable salt" refers to a charged species of the parent conjugate and its counter ion, which is typically used to modify the solubility characteristics of the parent conjugate and/or to reduce any significant irritation to an organism by the parent conjugate, while not abrogating the biological activity and properties of the administered conjugate.

Examples of pharmaceutically acceptable salts include, but are not limited to, mineral or organic acid salts of basic residues such as amines, and alkali or organic salts of acidic residues such as carboxylic acids. The pharmaceutically acceptable salts include the conventional non-toxic salts or the quaternary ammonium salts of the parent compound formed, for example, from non-toxic inorganic or organic acids. Conventional nontoxic salts include those derived from inorganic acids such as hydrochloric, hydrobromic, sulfuric, sulfamic, phosphoric and nitric acid; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic and isethionic acids. The pharmaceutically acceptable salts can be synthesized from the parent compound, which contains a basic or acidic moiety, by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences,* 17th ed. (Mack Publishing Company, Easton, Pa., 19143, p. 1418).

Representative examples of conjugate pharmaceutically acceptable salts that can be efficiently used in the context of the present invention include, without limitation, conjugate hydrochloride and conjugate mesylate.

According to some embodiments of the present invention, the compositions, uses and method of treatment, according to some embodiment of the present invention, may include the co-administration of at least one additional therapeutically active agent, as this is defined and discussed herein.

The conjugates described herein can be beneficially utilized per-se in the treatment of pathogenic microorganism infections, as these are defined hereinbelow. As demonstrated in the Example section that follows, such conjugates are by themselves capable of exerting antimicrobial activity. The option to include an additional therapeutically active agent may thus act synergistically or cooperatively as toxic agents against various bacteria, fungi and other microorganisms.

Exemplary additional therapeutically active agents include, but are not limited to, an antibiotic agent, an anti-inflammatory agent, an anti-pruritic agent, an anti-proliferative agent and the likes.

While most known antibiotics act by interfering selectively with the biosynthesis of one or more of the molecular constituents of the cell-membrane, proteins or nucleic acids, the conjugates presented herein also act by reducing or preventing the adverse effects of microbial drug resistance, and therefore may also act to increase the sensitivity of pathogenic microorganism to the antibiotic treatment, including resistant strains.

In general, the additional therapeutically active agent is selected such that it exerts a beneficial effect in the treatment against an infection, hence the additional therapeutically active agent may be an antimicrobial agent, as this is defined hereinabove.

It is expected that during the life of a patent maturing from this application many relevant antimicrobial conjugates will be developed and the scope of the phrase "antimicrobial conjugates" is intended to include all such new technologies a priori.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions, illustrate some embodiments of the invention in a non limiting fashion.

Materials and Methods

Methods:
$^1$H NMR spectra (including DEPT, 2D-COSY, 2D TOCSY, 1D TOCSY, HMQC, HMBC) were recorded on a Bruker Avance™ 500 spectrometer, and chemical shifts reported (in ppm) are relative to internal Me$_4$Si ($\delta$=0.0) with CDCl$_3$ as the solvent, and to HOD ($\delta$=4.63) with D$_2$O as the solvent.

$^{13}$C NMR spectra were recorded on a Bruker Avance™ 500 spectrometer at 125.8 MHz, and the chemical shifts reported (in ppm) relative to the residual solvent signal for CDCl$_3$ ($\delta$=77.00), or to external sodium 2,2-dimethyl-2-silapentane sulfonate ($\delta$=0.0) for D$_2$O as the solvent.

Mass spectra (MS) analysis were obtained either on a Bruker Daltonix Apex 3 mass spectrometer under electron spray ionization (ESI), or by a TSQ-70B mass spectrometer (Finnigan Mat).

Reactions were monitored by TLC on silica gel 60 F$_{254}$ (0.25 mm, Merck), and spots were visualized by charring with a yellow solution containing (NH$_4$)Mo$_7$O$_{24}$4.H$_2$O (120 grams) and (NH$_4$)$_2$Ce(NO$_3$)$_6$ (5 grams) in 10% H$_2$SO$_4$ (800 mL).

Flash column chromatography was performed on silica gel 60 (70-230 mesh).

IR spectra (CHCl$_3$) were recorded on a Bruker vector 22 spectrophotometer, and only significant peaks were identified. Microwave assisted reactions were carried out in domestic microwave oven Sauter SG251. Analytical HPLC was performed on Hitachi LC system equipped with auto-sampler, by using Superspher® 100 RP-18 column and a detection wavelength was 271 nm.

All syntheses reactions were carried out under an argon atmosphere with anhydrous solvents, unless otherwise noted.

Materials:
1-Bromo-2-chloroethane, 1-bromo-3-chloropropane, 1-bromo-4-chlorobutane, 1-bromo-5-chloropentane, 1,6-dibromohexane, 1,3-dibromo-2-propanol, 2-bromoethyl ether, α,α'-dibromo-meta-xylene, and α,α'-dibromo-para-xylene as well as 4-ethynylaniline and propargylamine were obtained from Sigma-Aldrich Israel.

Compound 7 was prepared as previously reported [29].

Purity of the Compounds 1a-q was determined by using HPLC analysis which indicated more than 95% purity of each products.

All other chemicals, reagents and solvents were obtained from commercial sources such as Sigma-Aldrich, Fluka and Acros unless stated otherwise.

Plasmid pETSACG1 carrying the APH(3')-IIIa gene (Gene bank Accession No. V01547) was generously provided by Prof. A. Berghuis, McGill University. Plasmid pSF815 carrying the AAC(6')-APH(2") gene was generously provided by Prof. S. Mobashery, University of Notre Dame. Plasmid pET9d carrying the APH(3')-Ia gene was obtained from New England Biolabs.

Example 1

Syntheses

The general synthesis of the Cipro-NeoB conjugates (Compound 1), according to some embodiments of the present invention, from Compound 2 (the "Cipro" moiety) and Compound 3 (the "NeoB" moiety), is illustrated in Scheme 5 below.

X and Y represent various first and second spacer moieties respectively, which form the connecting moiety together with the resultant 4-yl-1-yl-1H-1,2,3-triazole linking moiety.

Nine exemplary azido-derivatives of Cipro (referred to herein and presented below as Compounds 2a-i), and three exemplary alkyne-derivatives of NeoB (referred to herein and presented below as Compounds 3a-c), were prepared and coupled via "click reaction" [30] to afford a library of 17 exemplary Cipro-NeoB conjugates, according to some embodiments of the present invention, which are also referred to herein and presented below as Compounds 1a-q. The first and second spacer moieties, namely X and Y, were selected to vary both the length and chemical nature of the linkage between the two pharmacophores, the Cipro moiety and the NeoB moiety.

Preparation of Compound 1—General Procedure A:

Exemplary conjugates, according to some embodiments of the present invention, referred to herein in general as Compound 1, were prepared as illustrated in Scheme 5 above.

A solution of Compound 2 (0.06 mmol), and Compound 3 (0.05 mmol), [(CH$_3$CN)$_4$Cu]PF$_6$ (0.025 mmol) in a solution of Et$_3$N in water (7%, 5 ml) is placed in a glass vial (25 ml). The vial is closed with a stopper and heated in a domestic microwave oven for 40 seconds at maximum power. Propa-

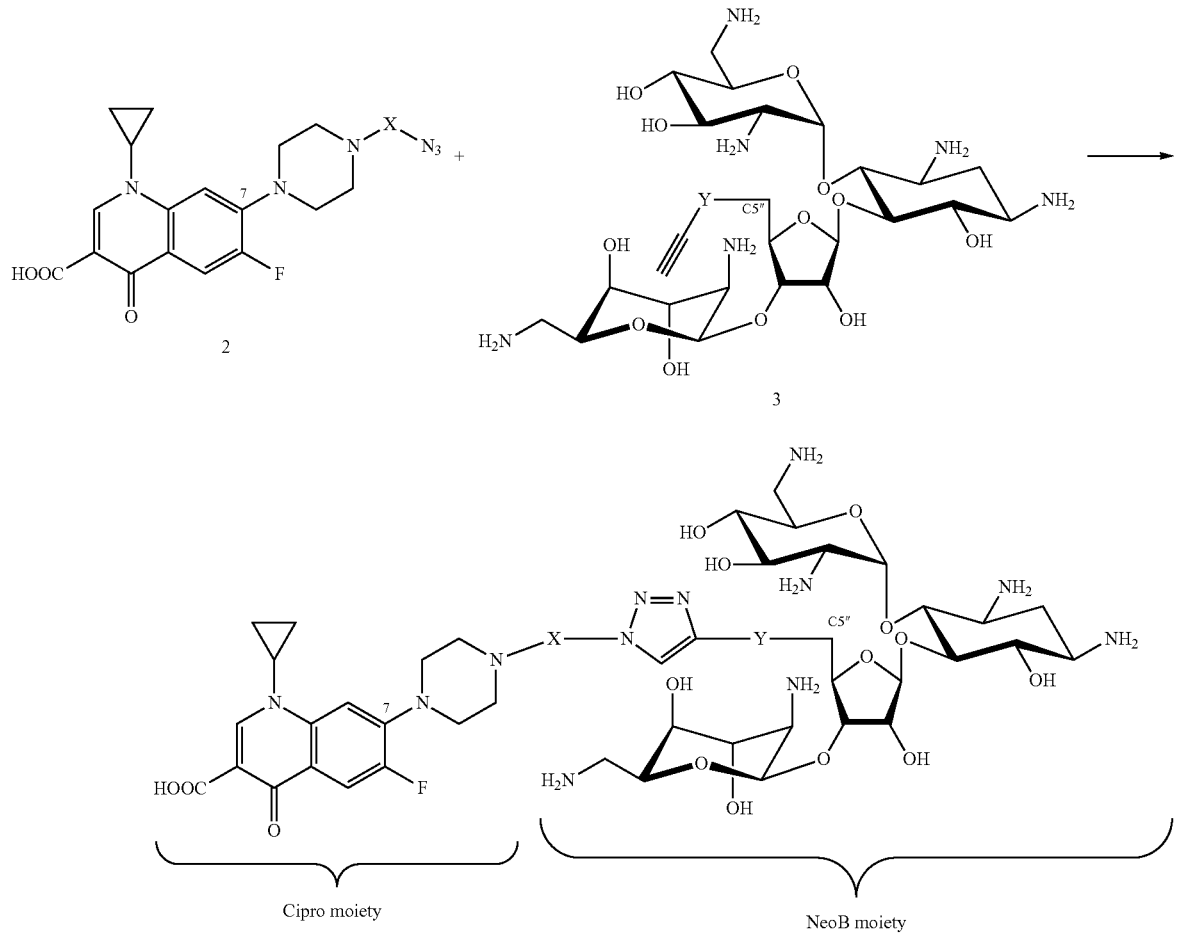

Scheme 5 gation of the reaction is monitored by TLC using a mixture of 10:15:6:15 $CH_2Cl_2/MeOH/H_2O/MeNH_2$ as eluent (for a sample containing 33% reaction solution in EtOH). After completion, the reaction mixture is purified on a short column of Amberlite CG-50 ($H^+$-form). The column is sequentially washed by MeOH, MeOH/MeNH$_2$ (33% solution in EtOH) 95:5, MeOH/MeNH$_2$ (33% solution in EtOH) 9:1 and MeOH/MeNH$_2$ (33% solution in EtOH) 4:1. Fractions containing the product were combined, evaporated, re-dissolved in water and evaporated again to afford the free amine form of the product.

The product is dissolved in water; the pH is adjusted to 3.2 with TFA (0.01 M), and lyophilized to afford the TFA salt of the final product, typically as a white foamy solid.

Chemical yields of the obtained Compounds 1a-q are given in Table 4 hereinbelow and their complete analytical data are provided hereinbelow.

Preparation of Compound 2—General Procedure B:

Several SAR studies on fluoroquinolones have demonstrated a high tolerance for structural variations at the 7-position of the phenyl ring (marked with "7" in Scheme 5 and Scheme 6), including alkylations at the terminal nitrogen of the piperazine moiety [7, 9-11, 21, 22].

Hence, Compound 2 (the "Cipro" moiety), is prepared as illustrated in Scheme 6 below, wherein X represents first spacer moiety and D represents a halo group.

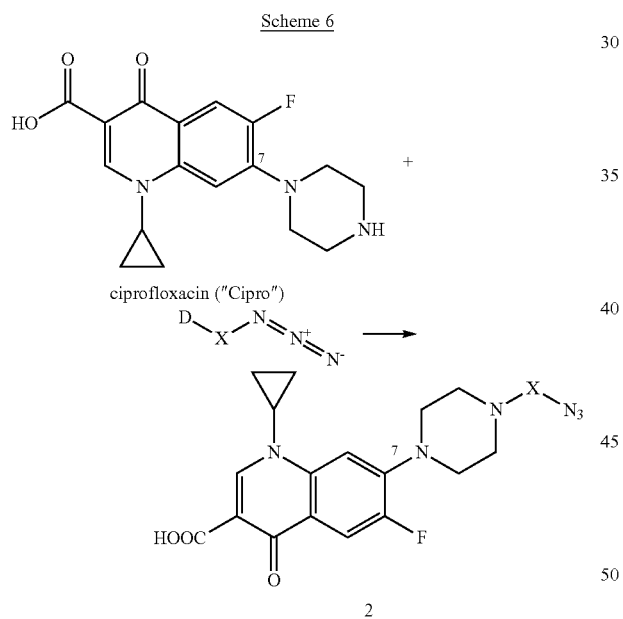

The azido-containing first spacer moiety precursor compounds are synthesized from the corresponding dibromo or bromochloro compounds according to published procedure [31]. A mixture of ciprofloxacin (Cipro, 1 mmol) and an azido-containing first spacer moiety precursor compound (5 mmol) in acetonitrile (15 mL) is refluxed in the presence of powdered NaHCO$_3$ (1 mmol) for 12-24 hours. When a TLC (MeOH/CH$_2$Cl$_2$, 1:9) indicates completion of the reaction (within 2-14 hours), the mixture is filtered, washed with excess MeOH/CH$_2$Cl$_2$ (1:1) and the combined filtrates are evaporated to dryness under reduced pressure.

The residue is purified by column chromatography (silica gel, MeOH/CH$_2$Cl$_2$, 1:10) to yield the product, typically as a slightly yellow solid.

Cipro was subjected to modifications at the terminal nitrogen of the piperazine moiety with various azido-containing first spacer moiety precursor compounds to afford the exemplary Compounds 2a-I, which were prepared as described in General Procedure B by direct coupling of the commercial Cipro with the corresponding bromo/chloro-azides under reflux and base conditions (NaHCO$_3$, CH$_3$CN). Chemical yields of these products are summarized in Table 3 hereinbelow.

Preparation of Compound 3—General Procedure C:

The synthesis of two types of alkyne derivatives of NeoB (Compounds 3) is illustrated in Scheme 7 below.

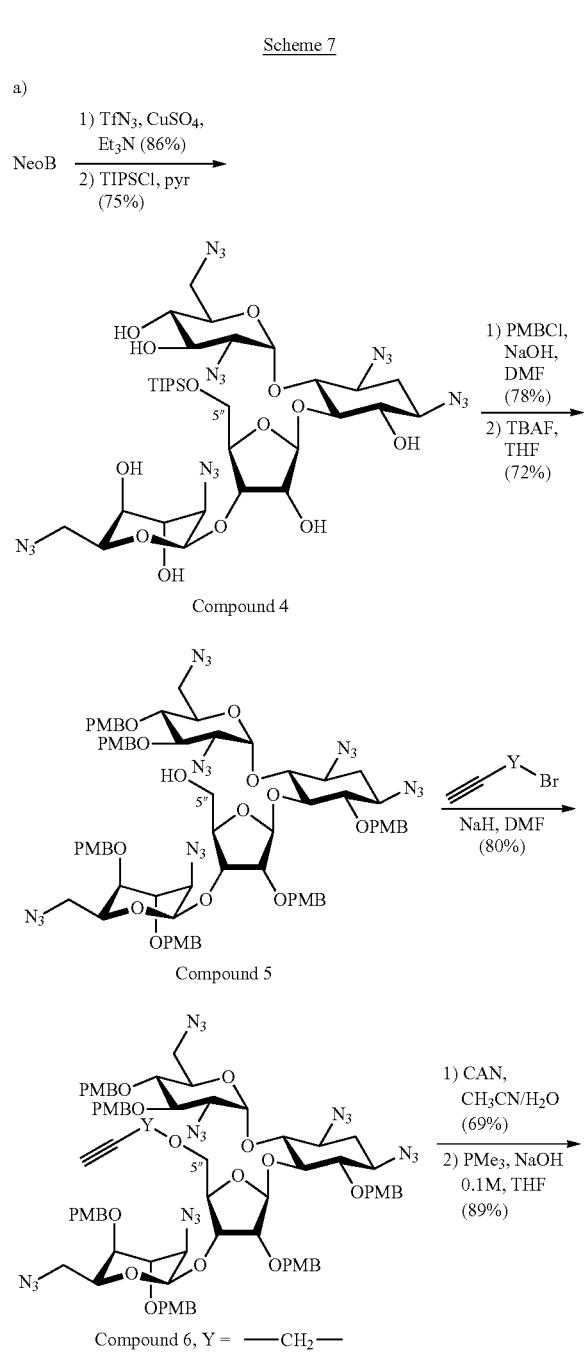

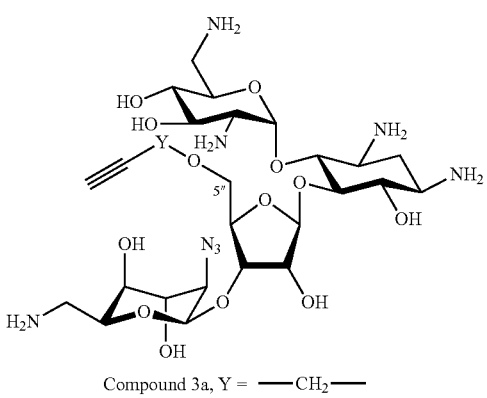

Compound 3a, Y = —CH₂— b)

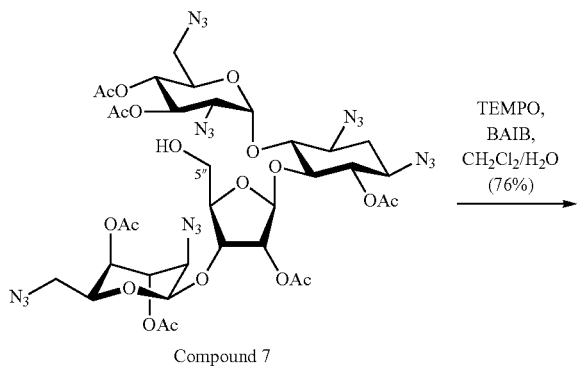

Compound 7

TEMPO, BAIB, CH₂Cl₂/H₂O (76%)

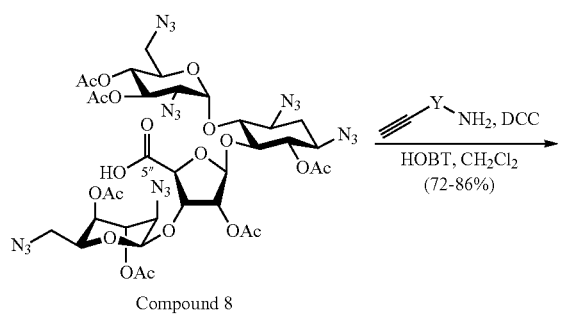

Compound 8

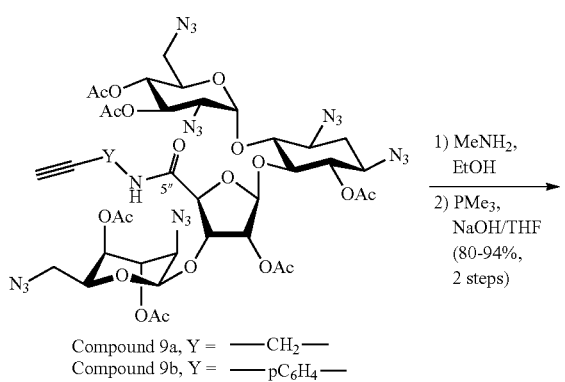

Compound 9a, Y = —CH₂—
Compound 9b, Y = —pC₆H₄—

1) MeNH₂, EtOH
2) PMe₃, NaOH/THF
(80-94%, 2 steps)

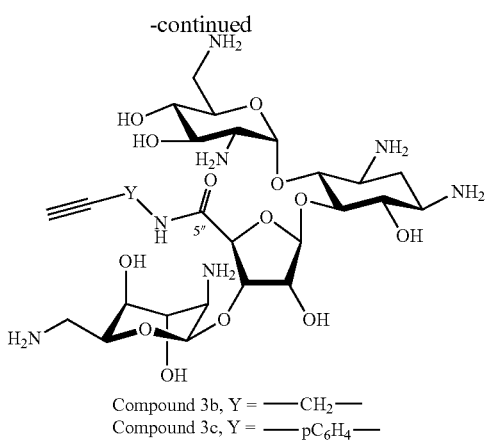

Compound 3b, Y = —CH₂—
Compound 3c, Y = —pC₆H₄—

For the preparation of the alkyne-NeoB derivative Compound 3a, commercial NeoB is converted to the corresponding per-azido derivative according to published procedure [32], followed by selective protection of the primary hydroxyl to afford the intermediate Compound 4. Protection of all the secondary hydroxyls with p-methoxybenzyl (PMB) ether and selective removal of silyl ether with TBAF affords Compound 5. Treatment of Compound 5 with propargyl bromide under alkaline conditions (e.g., NaH) affords the 5"-alkyne derivative Compound 6. Deprotection steps for removal of PMB ether protections with CAN, followed by Staudinger reaction to convert all the azides to the corresponding amines, afford the alkyne-NeoB derivative Compound 3a.

Two other alkyne derivatives of NeoB, Compounds 3b-c, contain a terminal alkyne group connected to the NeoB moiety at 5"-position via an amide linkage. For the assembly of these derivatives, the readily available 5"-alcohol 7 [29] is converted to the corresponding 5"-acid Compound 8 according to a published procedure [33]. The resulting acid is thereafter coupled with the commercially available alkyne-amines in the presence of DCC to afford the corresponding amide Compounds 9a-b. Finally, removal of all the ester protections (MeNH₂, MeOH) followed by Staudinger reaction yield the alkyne-NeoB derivative Compound 3b-c in high yields.

Preparation of Exemplary Compounds:

Reagents used and chemical yield obtained in the preparation of exemplary Compounds 2a-i are presented in Table 3 below. All of Compounds 2a-i were prepared following General Procedure B presented hereinabove.

TABLE 3

Compounds 2a-i

| Compound | azido-containing precursor compound | X | (%) |
|---|---|---|---|
| 2a | (Cl)Br—(CH₂)₂—N₃ | —(CH₂)₂— | 75 |
| 2b | (Cl)Br—(CH₂)₃—N₃ | —(CH₂)₃— | 70 |
| 2c | (Cl)Br—(CH₂)₄—N₃ | —(CH₂)₄— | 80 |
| 2d | (Cl)Br—(CH₂)₅—N₃ | —(CH₂)₅— | 65 |
| 2e | Br—(CH₂)₆—N₃ | —(CH₂)₆— | 57 |
| 2f | Br—CH₂CH(OH)CH₂—N₃ | —CH₂CH(OH)CH₂— | 31 |
| 2g | Br—(CH₂)₂—O—(CH₂)₂—N₃ | —(CH₂)₂—O—(CH₂)₂— | 75 |

TABLE 3-continued

Compounds 2a-i

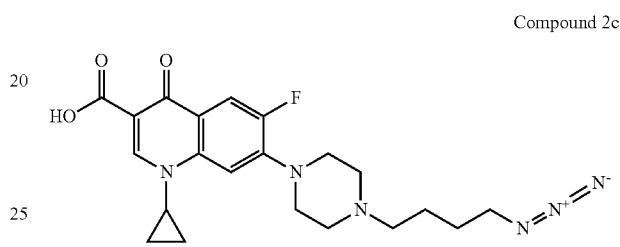

| Compound | azido-containing precursor compound | X | (%) |
|---|---|---|---|
| 2h | Br—CH$_2$—$m$C$_6$H$_4$—CH$_2$—N$_3$ | —CH$_2$—$m$C$_6$H$_4$—CH$_2$— | 44 |
| 2i | Br—CH$_2$—$p$C$_6$H$_4$—CH$_2$—N$_3$ | —CH$_2$—$p$C$_6$H$_4$—CH$_2$— | 30 |

7-(4-(2-azidoethyl)piperazin-1-yl)-1-cyclopropyl-6-fluoro-1,4-dihydro-4-oxoquinoline-3-carboxylic acid (Compound 2a)

Compound 2a

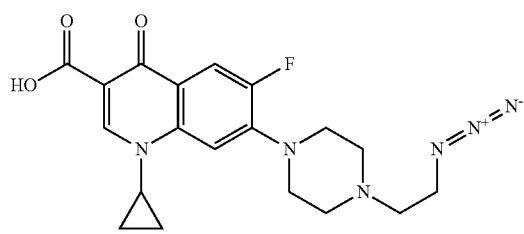

$^1$H NMR (500 MHz, CDCl$_3$): δ=1.14-1.15 (d, J=3.0 Hz, 2H, cyclopropane), 1.34-1.35 (d, J=7.0 Hz, 2H, cyclopropane), 2.65-2.67 (t, J=6.0 Hz, 2H, NCH$_2$), 2.69-2.71 (t, J=5.0 Hz, 4H, piperazine), 3.31-3.33 (t, J=5.0 Hz, 4H, piperazine), 3.34-3.36 (t, J=6.0 Hz, 2H, CH$_2$N$_3$), 3.51-3.53 (m, 1H, cyclopropane), 7.29-7.30 (d, J=7.0 Hz, 1H, C$_8$—H), 7.78-7.80 (d, J=14.0 Hz, 1H, C$_5$—H), 8.61 (s, 1H, C$_2$—H) ppm.
$^{13}$C NMR (125 MHz, CDCl$_3$): δ=9.9 (CH$_2$ of cyclopropane), 10.0 (CH$_2$ of cyclopropane), 31.5 (CH of cyclopropane), 49.8 (CH$_2$N$_3$), 51.4, 54.5, 58.9 (NCH$_2$), 106.7, 109.6, 113.7, 121.2, 140.8, 147.6, 149.1, 154.4, 156.4, 168.8, 178.7. IR (CHCl$_3$, cm$^{-1}$): 2120 (N$_3$), 1730 (CO) ppm.
MALDI TOFMS calculated for C$_{19}$H$_{21}$FN$_6$O$_3$Na ([M+Na]$^+$): m/e=423.4; measured m/e=423.2.

7-(4-(3-Azidopropyl)piperazin-1-yl)-1-cyclopropyl-6-fluoro-4-oxo-1,4-dihydroquinoline-3-carboxylic acid (Compound 2b)

Compound 2b

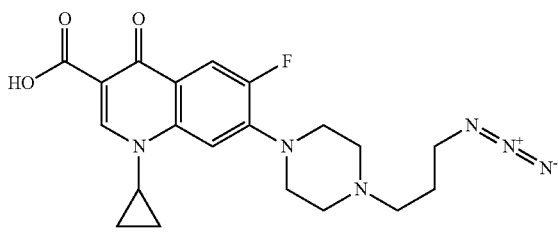

$^1$H NMR (500 MHz, CDCl$_3$): δ=1.19 (m, 2H, cyclopropane), 1.38-1.39 (d, J=6.0 Hz, 2H, cyclopropane), 1.79-1.84 (m, 2H, CH$_2$ of linker), 2.52-2.54 (t, J=7.0 Hz, 2H, NCH$_2$), 2.68 (m, 4H, piperazine), 3.36 (m, 4H, piperazine), 3.38-3.40 (t, J=7.0 Hz, 2H, CH$_2$N$_3$), 3.54-3.55 (m, 1H, cyclopropane), 7.34-7.35 (d, J=7.0 Hz, 1H, C$_8$—H), 7.91-7.93 (d, J=7.0 Hz, 1H, C$_5$—H), 8.70 (s, 1H, C$_2$—H) ppm.
$^{13}$C NMR (125 MHz, CDCl$_3$): δ=10.0 (CH$_2$ of cyclopropane), 28.0 (CH$_2$ of linker), 37.1 (CH of cyclopropane), 51.2, 51.5 (CH$_2$N$_3$), 54.5, 56.8 (NCH$_2$), 106.6, 109.7, 113.9, 114.1, 121.4, 140.9, 147.6, 149.1, 154.4, 156.4, 168.8, 178.8. IR (CHCl$_3$, cm$^{-1}$): 2100 (N$_3$), 1722 (CO) ppm.
MALDI TOFMS calculated for C$_{20}$H$_{23}$FN$_6$O$_3$Na ([M+Na]$^+$): m/e=437.4; measured m/e=437.4.

7-(4-(4-Azidobutyl)piperazin-1-yl)-1-cyclopropyl-6-fluoro-4-oxo-1,4-dihydroquinoline-3-carboxylic acid (Compound 2c)

Compound 2c

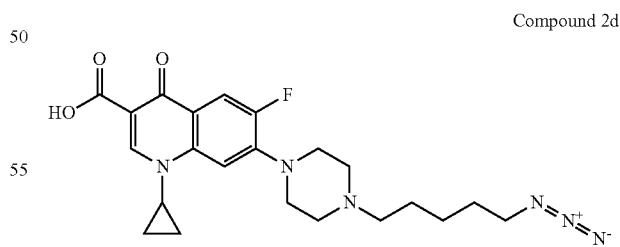

$^1$H NMR (500 MHz, CDCl$_3$): δ=1.17 (m, 2H, cyclopropane), 1.36-1.37 (d, J=6.0 Hz, 2H, cyclopropane), 1.62-1.65 (m, 4H, CH$_2$ of linker), 2.44-2.46 (t, J=7.0 Hz, 2H, NCH$_2$), 2.65 (m, 4H, piperazine), 3.31-3.34 (m, 4H, piperazine; 2H, CH$_2$N$_3$), 3.54-3.55 (m, 1H, cyclopropane), 7.31-7.33 (d, J=7.0 Hz, 1H, C$_8$—H), 7.82-7.85 (d, J=7.0 Hz, 1H, C$_5$—H), 8.64 (s, 1H, C$_2$—H) ppm.
$^{13}$C NMR (125 MHz, CDCl$_3$): δ=10.0 (CH$_2$ of cyclopropane), 25.7 (CH$_2$ of linker), 28.6 (CH$_2$ of linker), 37.1 (CH of cyclopropane), 51.2, 51.5, 53.1 (CH$_2$N$_3$), 54.5, 59.5 (NCH$_2$), 106.6, 109.6, 113.7, 113.9, 121.2, 140.8, 147.6, 149.1, 154.4, 156.4, 168.7, 178.7. IR (CHCl$_3$, cm$^{-1}$): 2100 (N$_3$), 1718 (CO) ppm.
MALDI TOFMS calculated for C$_{21}$H$_{25}$FN$_6$O$_3$ ([M+H]$^+$): m/e=429.5; measured m/e=429.4.

7-(4-(5-Azidopentyl)piperazin-1-yl)-1-cyclopropyl-6-fluoro-4-oxo-1,4-dihydroquinoline-3-carboxylic acid (Compound 2d)

Compound 2d $^1$H NMR (500 MHz, CDCl$_3$): δ=1.20 (m, 2H, cyclopropane), 1.38-1.40 (d, J=7.0 Hz, 2H, cyclopropane), 1.42-1.47 (m, 2H, CH$_2$ of linker), 1.55-1.61 (m, 2H, CH$_2$ of linker), 1.62-1.68 (m, 2H, CH$_2$ of linker), 2.44-2.47 (t, J=7.0 Hz, 2H, NCH$_2$), 2.68 (m, 4H, piperazine), 3.28-3.31 (t, J=6.0 Hz, 2H, CH$_2$N$_3$), 3.36 (m, 4H, piperazine), 3.54-3.56 (m, 1H, cyclopropane), 7.35-7.36 (d, J=7.0 Hz, 1H, C$_8$—H), 7.96-7.99 (d, J=13.0 Hz, 1H, C$_5$—H), 8.75 (s, 1H, C$_2$—H) ppm.

$^{13}$C NMR (125 MHz, CDCl$_3$): δ=10.0 (CH$_2$ of cyclopropane), 26.4 (CH$_2$ of linker), 28.1 (CH$_2$ of linker), 30.5 (CH$_2$ of linker), 37.1 (CH of cyclopropane), 51.6, 53.2 (CH$_2$N$_3$), 54.6, 60.0 (NCH$_2$), 106.5, 109.9, 114.1, 114.2, 121.5, 140.9, 147.7, 154.5, 156.5, 168.9, 178.9. IR (CHCl$_3$, cm$^{-1}$): 2110 (N$_3$), 1723 (CO) ppm.

MALDI TOFMS calculated for C$_{22}$H$_{27}$FN$_6$O$_3$ ([M+H]$^+$): m/e=443.5; measured m/e=443.3.

7-(4-(6-Azidohexyl)piperazin-1-yl)-1-cyclopropyl-6-fluoro-4-oxo-1,4-dihydroquinoline-3-carboxylic acid (Compound 2e)

Compound 2e

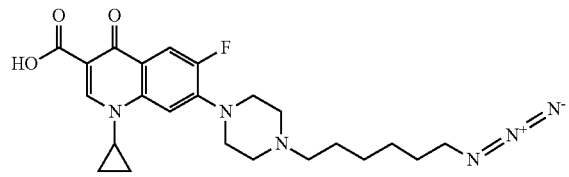

$^1$H NMR (500 MHz, CDCl$_3$): δ=1.18-1.19 (m, 2H, cyclopropane), 1.36-1.43 (m, 2H, cyclopropane; 4H, CH$_2$ of linker), 1.54-1.63 (m, 4H, CH$_2$ of linker), 2.42-2.45 (t, J=7.5 Hz, 2H, NCH$_2$), 2.68 (m, 4H, piperazine), 3.26-3.28 (t, J=6.5 Hz, 2H, CH$_2$N$_3$), 3.35-3.37 (m, 4H, piperazine), 3.53-3.57 (m, 1H, cyclopropane), 7.33-7.35 (d, J=7.0 Hz, 1H, C$_8$—H), 7.90-7.93 (d, J=13.5 Hz, 1H, C$_5$—H), 8.70 (s, 1H, C$_2$—H) ppm.

$^{13}$C NMR (125 MHz, CDCl$_3$): δ=10.0 (CH$_2$ cyclopropane), 28.4 (CH$_2$ of linker), 28.8 (CH$_2$ of linker), 30.6 (CH$_2$ of linker), 37.1 (CH of cyclopropane), 51.5, 53.2 (CH$_2$N$_3$), 54.6, 60.1 (NCH$_2$), 106.5, 109.8, 113.9, 114.1, 121.4, 140.9, 147.7, 149.1, 154.4, 156.4, 168.8, 178.8. IR (CHCl$_3$, cm$^{-1}$): 2110 (N$_3$), 1726 (CO) ppm.

MALDI TOFMS calculated for C$_{23}$H$_{29}$FN$_6$O$_3$ ([M+H]$^+$): m/e=457.3; measured m/e=457.5.

7-(4-(3-Azido-2-hydroxypropyl)piperazin-1-yl)-1-cyclopropyl-6-fluoro-4-oxo-1,4-dihydroquinoline-3-carboxylic acid (Compound 2f)

Compound 2f

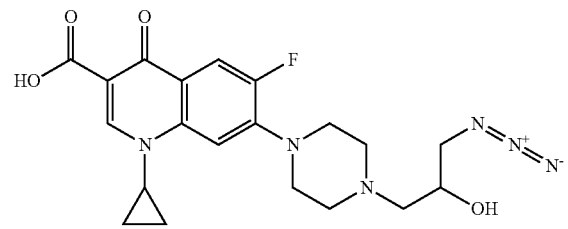

$^1$H NMR (500 MHz, CDCl$_3$): δ=1.20-1.21 (d, J=4.0 Hz, 2H, cyclopropane), 1.39-1.41 (d, J=7.0 Hz, 2H, cyclopropane), 2.46-2.49 (dd, J=3.0, 12.0 Hz, 1H, NCH$_2$), 2.57-2.62 (dd, J=10.0, 12.0 Hz, 1H, NCH$_2$), 2.67-2.71 (m, 2H, piperazine), 2.87-2.92 (m, 2H, piperazine), 3.24-3.28 (dd, J$_1$=6.0 Hz, J$_2$=13.0 Hz, 1H, CH$_2$N$_3$), 3.36-3.39 (dd, J$_1$=6.0 Hz, J$_2$=13.0 Hz, 4H, piperazine), 3.44-3.47 (dd, J$_1$=4.0 Hz, J$_2$=9.0 Hz, 1H, CH$_2$N$_3$), 3.54-3.58 (m, 1H, cyclopropane), 3.94-3.98 (m, 1H, CH—OH), 7.34-7.36 (d, J=7.0 Hz, 1H, C$_8$—H), 7.91-7.94 (d, J=13.0 Hz, 1H, C$_5$—H), 8.70 (s, 1H, C$_2$—H) ppm.

$^{13}$C NMR (125 MHz, CDCl$_3$): δ=10.0 (CH$_2$ of cyclopropane), 37.2 (CH of cyclopropane), 51.6, 54.7, 56.1, 62.4, 68.0, 106.7, 109.8, 114.0, 114.2, 121.5, 140.8, 147.5, 149.2, 154.4, 156.4, 168.8, 178.8. IR (CHCl$_3$): 2110 (N$_3$), 1723 (CO) ppm.

MALDI TOFMS calculated for C$_{20}$H$_{23}$FN$_6$O$_4$ ([M+H]$^+$): m/e=431.4; measured m/e=431.0.

7-(4-(2-(2-Azidoethoxy)ethyl)piperazin-1-yl)-1-cyclopropyl-6-fluoro-4-oxo-1,4-dihydroquinoline-3-carboxylic acid (Compound 2g)

Compound 2g

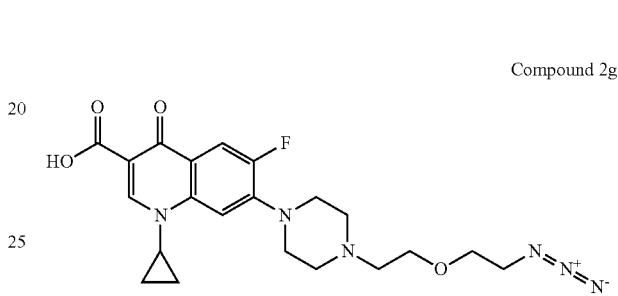

$^1$H NMR (500 MHz, CDCl$_3$): δ=1.17-1.20 (m, 2H, cyclopropane), 1.36-1.40 (m, 2H, cyclopropane), 2.72-2.74 (t, J=5.0 Hz, 2H, NCH$_2$), 2.78-2.79 (m, 4H, piperazine), 3.37-3.41 (m, 4H, piperazine; 2H, CH$_2$N$_3$), 3.53-3.57 (m, 1H, cyclopropane), 3.66-3.68 (t, J=4.0 Hz, 2H, CH$_2$ of linker), 3.69-3.71 (t, J=4.0 Hz, 2H, CH$_2$ of linker), 7.34-7.35 (d, J=8.0 Hz, 1H, C$_8$—H), 7.92-7.95 (d, J=13.0 Hz, 1H, C$_5$—H), 8.71 (s, 1H, C$_2$—H) ppm.

$^{13}$C NMR (125 MHz, CDCl$_3$): δ=10.0 (CH$_2$ of cyclopropane), 37.1 (CH of cyclopropane), 51.4, 52.5 (CH$_2$N$_3$), 55.0, 59.5 (NCH$_2$), 70.9 (CH$_2$ of linker), 71.7 (CH$_2$ of linker), 106.6, 109.8, 114.0, 114.1, 121.4, 140.9, 147.7, 149.1, 154.4, 156.4, 168.8, 178.8. IR (CHCl$_3$, cm$^{-1}$): 2110 (N$_3$), 1722 (CO) ppm.

MALDI TOFMS calculated for C$_{21}$H$_{25}$FN$_6$O$_4$ ([M+H]$^+$): m/e=445.3; measured m/e=445.5.

7-(4-(3-(Azidomethyl)benzyl)piperazin-1-yl)-1-cyclopropyl-6-fluoro-4-oxo-1,4- to dihydroquinoline-3-carboxylic acid (Compound 2h)

Compound 2h

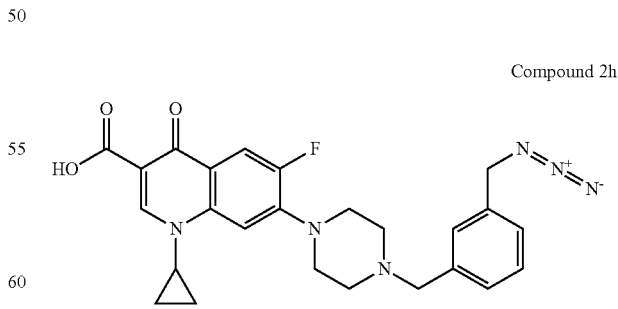

$^1$H NMR (500 MHz, CDCl$_3$): δ=1.16-1.19 (m, 2H, cyclopropane), 1.34-1.38 (m, 2H, cyclopropane), 2.67-2.69 (t, J=4.5 Hz, 4H, piperazine), 3.35-3.37 (t, J=4.5 Hz, 4H, piperazine), 3.51-3.55 (m, 1H, cyclopropane), 3.62 (s, 2H, NCH$_2$), 4.35 (s, 2H, CH$_2$N$_3$), 7.22-7.24 (m, 1H, aromatic), 7.30-7.37 (m, 4H, aromatic, C$_8$—H), 7.86-7.89 (d, J=13.0 Hz, 1H, C$_5$—H), 8.67 (s, 1H, C$_2$—H) ppm.

$^{13}$C NMR (125 MHz, CDCl$_3$): δ=10.0 (CH$_2$ of cyclopropane), 31.4 (CH of cyclopropane), 51.5, 54.5, 56.5 (CH$_2$N$_3$), 64.4 (NCH$_2$), 106.6, 109.7, 113.8, 114.0, 121.2, 129.0, 130.7, 130.9, 137.3, 140.3, 140.9, 154.4, 156.4, 168.8, 178.7 ppm.

MALDI TOFMS calculated for C$_{25}$H$_{25}$FN$_6$O$_3$ ([M+H]$^+$): m/e=477.2; measured m/e=477.5.

7-(4-(4-(Azidomethyl)benzyl)piperazin-1-yl)-1-cyclopropyl-6-fluoro-4-oxo-1,4-dihydroquinoline-3-carboxylic acid (Compound 2i)

Compound 2i

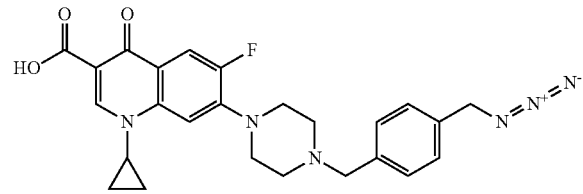

$^1$H NMR (500 MHz, CDCl$_3$): δ=1.17-1.20 (m, 2H, cyclopropane), 1.35-1.39 (m, 2H, cyclopropane), 2.68-2.69 (t, J=5.0 Hz, 4H, piperazine), 3.35-3.37 (t, J=5 Hz, 4H, piperazine), 3.52-3.54 (m, 1H, cyclopropane), 3.61 (s, 2H, NCH$_2$), 4.34 (s, 2H, CH$_2$N$_3$), 7.29-7.31 (d, J=7.5 Hz, 2H, aromatic), 7.33-7.34 (d, J=7.0 Hz, 1H, C$_8$—H), 7.38-7.39 (d, J=7.5 Hz, 2H, aromatic), 7.91-7.94 (d, J=13.0 Hz, 1H, C$_5$—H), 8.70 (s, 1H, C$_2$—H) ppm.

$^{13}$C NMR (125 MHz, CDCl$_3$): δ=8.1 (CH$_2$ of cyclopropane), 35.2 (CH of cyclopropane), 49.7, 52.6 (CH$_2$N$_3$), 54.5, 62.4 (NCH$_2$), 104.7, 107.9, 112.1, 112.3, 119.5, 128.2, 129.5, 134.4, 137.9, 139.0, 145.9, 147.3, 152.6, 154.6, 167.0, 177.0 ppm.

MALDI TOFMS calculated for C$_{25}$H$_{25}$FN$_6$O$_3$ ([M+H]$^+$): m/e=477.1; measured m/e=477.5.

Exemplary Compounds 3a-c were prepared following General Procedure C presented hereinabove, using two synthetic routes as presented in Scheme 7 hereinabove.

Preparation of 1,3,2',6',2''',6'''-Hexaazido-5''-triisopropylsilyloxy-neomycin (Compound 4)

Compound 4

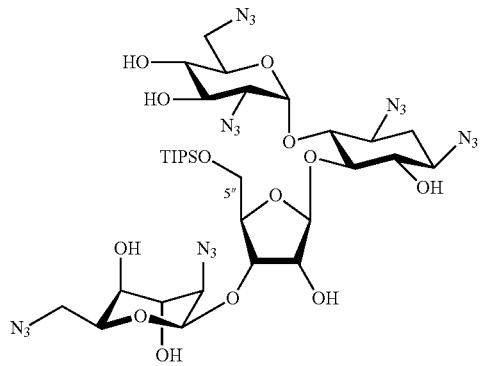

Commercially available NeoB was converted to the corresponding perazido derivative according to the published procedure [32]. Hexaazido-NeoB (5.10 grams, 6.62 mmol) was dissolved in pyridine (30 ml), added with 4-DMAP (catalytic amount) and stirred at room temperature. After 15 minutes, triisopropylsilylchloride (TIPSC1) (1.91 grams, 9.93 mmol) was added, and TLC (EtOAc, 100%) indicated completion after 3 hours. The mixture was diluted with EtOAc and washed with brine, H$_2$SO$_4$ (2%), saturated NaHCO$_3$, and brine. The organic layers were combined, dried over MgSO$_4$, evaporated and the residue was purified by flash chromatography (silica gel, EtOAc/Hexane) to yield the silyl ether Compound 4 as a white powder (4.60 grams, 75% yield).

$^1$H NMR (500 MHz, CDCl$_3$): δ=0.85-0.98 (m, 15H, TIPS); ring I: δ=3.14-3.28 (m, 3H, H-2, H-4, H-6), 3.33-3.51 (m, 1H, H-6'), 3.63-3.74 (m, 1H, H-3), 3.91-3.95 (m, 1H, H-5), 5.65-5.66 (d, J=3.5 Hz, 1H, H-1); ring II: δ=1.19-1.24 (ddd, J$_1$=J$_2$=J$_3$=12.5 Hz, 1H, H-2ax), 2.01-2.06 (dt, J=4.0, 12.5 Hz, 1H, H-2eq), 3.14-3.28 (m, 2H, H-1, H-3), 3.33-3.51 (m, 3H, H-4, H-5, H-6); ring III: δ=3.33-3.51 (m, 1H, H-5'), 3.63-3.74 (m, 1H, H-5), 4.03-4.05 (m, 2H, H-2, H-4), 4.22-4.23 (dd, J=4.0, 4.5 Hz, 1H, H-3), 5.10-5.11 (d, J=4.5 Hz, 1H, H-1); ring IV: δ=2.91-2.94 (dd, J=4.0, 10.5 Hz, 1H, H-6), 3.14-3.28 (m, 2H, H-4, H-6), 3.63-3.74 (m, 1H, H-2), 3.78-3.80 (t, J=3.5 Hz, 1H, H-3), 3.81-3.83 (m, 1H, H-5), 4.96 (d, J=1.0 Hz, 1H, H-1) ppm.

$^{13}$C NMR (125 MHz, CDCl$_3$): δ=11.5, 17.4, 31.6 (C-2), 50.8 (C-6'), 51.1 (C-6'''), 59.2, 59.4, 60.4, 63.2, 63.3, 68.4, 68.7, 70.5, 70.9, 71.1, 73.6, 74.3, 75.0, 75.3, 76.3, 83.1, 85.1, 96.3 (C-1'''), 98.6 (C-1'), 107.2 (C-1'') ppm.

MALDI TOFMS calcd for C$_{32}$H$_{54}$N$_{18}$O$_{13}$SiNa ([M+Na]$^+$): m/e=949.6; measured m/e=949.4.

Preparation of 1,3,2',6',2''',6'''-Hexaazido-6,3',4',2'',3''',4'''-hexa(4-methoxybenzyloxy)-5''-triisopropylsilyloxy-neomycin (Compound 5)

Compound 5

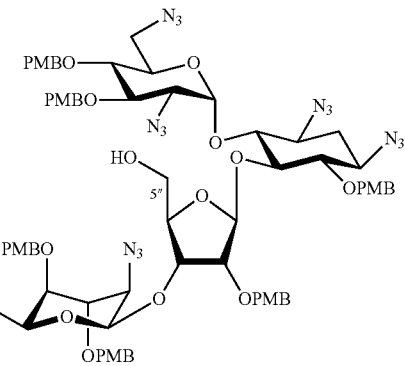

Compound 4 (3.0 grams, 3.24 mmol) was dissolved in anhydrous DMF (20 ml) and after stirring at 0° C. for 10 minutes 4-methoxybenzyl chloride (4.6 grams, 29.2 mmol) and NaH (0.17 grams, 7.29 mmol) were added. The reaction was allowed to warm to room temperature and after 4 hours TLC (EtOAc, 100%) indicated completion of the reaction. The mixture was diluted with EtOAc and washed with brine extensively. The combined organic layer was dried over MgSO$_4$, evaporated to dryness and used for the next step without further purification.

The crude from the previous step was dissolved in dry THF (10 ml), cooled at 0° C. and added with 1M solution of tetrabutyl ammonium fluoride in THF (3.74 ml, 3.74 mmol). The reaction progress was monitored by TLC (EtOAc/Hexane, 2:3), which indicated completion after 3 hours. The mixture was diluted with EtOAc (300 mL), and washed with brine. The combined organic layer was dried over MgSO$_4$, evaporated and purified by flash chromatography (silica gel, EtOAc/Hexane) to yield Compound 5 (3.5 grams, 72% for both steps).

$^1$H NMR (500 MHz, CDCl$_3$): δ=3.74 (s, 3H, CH$_3$O), 3.78 (s, 3H, CH$_3$O), 3.80 (s, 6H, CH$_3$O), 3.82 (s, 6H, CH$_3$O), 4.30-4.41 (m, 2H, CH$_2$ of PMB), 4.50-4.58 (m, 4H, CH$_2$ of PMB), 4.64-4.67 (m, 4H, CH$_2$ of PMB), 4.78-4.87 (m, 2H, CH$_2$ of PMB), 6.75-6.76 (m, 2H, aromatic), 6.86-6.90 (m, 10H, aromatic), 7.13-7.35 (m, 12H, aromatic); ring I: δ=3.12-3.15 (dd, J=4.0, 10.0 Hz, 1H, H-2), 3.29-3.36 (m, 1H, H-6), 3.40-3.51 (m, 2H, H-4, H-6'), 4.03-4.07 (dd, J=9.0, 11.0 Hz, 1H, H-3), 4.21-4.23 (m, 1H, H-5), 5.88-5.89 (d, J=4.0 Hz, 1H, H-1); ring II δ$_H$ 1.41-1.49 (ddd, J$_1$=J$_2$=J$_3$=12.5 Hz, 1H, H-2ax), 2.26-2.35 (dt, J=4.0, 12.5 Hz, 1H, H-2eq), 3.29-3.36 (m, 1H, H-1), 3.40-3.51 (m, 2H, H-3, H-5), 3.62-3.66 (t, J=10.0 Hz, 1H, H-4), 3.90-3.94 (t, J=9.0 Hz, 1H, H-6); ring III: δ=3.02-3.04 (dd, J=6.0, 9.0 Hz, 1H, H-5), 3.67-3.77 (m, 2H, H-2, H-5'), 4.11-4.12 (m, 1H, H-4), 4.33-4.35 (dd, J=4.0, 6.0 Hz, 1H, H-3), 5.68-5.69 (d, J=5.0 Hz, 1H, H-1); ring IV: δ=2.97-3.01 (dd, J=4.0, 12.0 Hz, 1H, H-6), 3.12 (m, 1H, H-4), 3.40-3.51 (m, 1H, H-2), 3.67-3.77 (m, 3H, H-3, H-5, H-6'), 4.97 (d, J=2.0 Hz, 1H, H-1) ppm.

$^{13}$C NMR (125 MHz, CDCl$_3$): δ=32.3 (C-2), 51.1 (C-6'), 55.2 (C-6''), 57.4, 59.6, 60.4, 61.9, 62.6, 71.0, 71.3, 72.0, 72.5, 72.9, 74.2, 74.6, 74.9, 75.7, 78.2, 78.6, 80.8, 81.9, 83.0, 83.9, 97.1 (C-1'''), 98.9 (C-1'), 105.4 (C-1'') ppm.

MALDI TOFMS calcd for C$_{71}$H$_{82}$N$_{18}$O$_{19}$Na ([M+Na]$^+$): m/e=1513.7; measured m/e=1513.5.

Preparation of 1,3,2',6',2''',6'''-Hexaazido-6,3',4',2'', 3''',4'''-hexa(4-methoxybenzyloxy)-5''-(prop-2-ynyloxy)-neomycin (Compound 6)

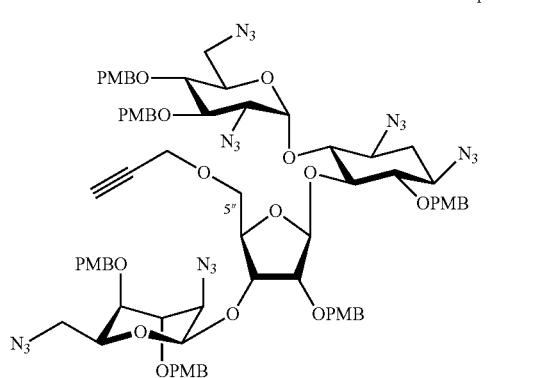

Compound 6

Compound 5 (0.73 grams, 0.49 mmol) was dissolved in dry DMF (15 ml) and was stirred at 0° C. for 10 minutes, followed by the addition of tetrabutyl ammonium iodide (0.54 grams, 1.47 mmol), propargyl bromide (0.35 grams, 2.97 mmol), and NaH (0.070 grams, 2.94 mmol). The reaction progress was monitored by TLC (EtOAc/Hexane, 4:5), which indicated completion after 4 hours. The mixture was diluted with EtOAc (200 ml) and washed with brine. The combined organic layer was dried over MgSO$_4$, evaporated and purified by flash chromatography (silica gel, EtOAc/Hexane) to yield Compound 6 (0.60 grams, 80% yield).

$^1$H NMR (500 MHz, CDCl$_3$): δ=2.44-2.45 (t, J=2.5 Hz, 1H, CH of triple bond), 3.73 (s, 3H, CH$_3$O), 3.78 (s, 3H, CH$_3$O), 3.80 (s, 3H, CH$_3$O), 3.81 (s, 3H, CH$_3$O), 3.82 (s, 6H, CH$_3$O), 4.13-4.14 (t, J=2.5 Hz, 2H, CH$_2$ of linker), 4.39-4.43 (m, 4H, CH$_2$ of PMB), 4.49-4.66 (m, 4H, CH$_2$ of PMB), 4.77-4.89 (m, 4H, CH$_2$ of PMB), 6.72-6.74 (m, 2H, aromatic), 6.84-6.89 (m, 10H, aromatic), 7.12-7.31 (m, 12H, aromatic); ring I: δ=3.28-3.32 (m, 1H, H-6), 3.35-3.37 (dd, J=3.5, 10.5 Hz, 1H, H-2), 3.41-3.51 (m, 1H, H-4), 3.56-3.58 (dd, J=3.0, 10.0 Hz, 1H, H-6'), 4.02-4.06 (dd, J=9.5, 10.0 Hz, 1H, H-3), 4.24-4.27 (m, 1H, H-5), 6.08-6.09 (d, J=3.5 Hz, 1H, H-1); ring II: δ=1.39-1.46 (ddd, J$_1$=J$_2$=J$_3$=12.5 Hz, 1H, H-2ax), 2.22-2.27 (dt, J=4.0, 12.5 Hz, 1H, H-2eq), 3.28-3.32 (m, 1H, H-1), 3.41-3.51 (m, 2H, H-3, H-5), 3.63-3.67 (t, J=9.0 Hz, 1H, H-4), 3.89-3.92 (t, J=9.0 Hz, 1H, H-6); ring III: δ=3.41-3.51 (m, 1H, H-5), 3.67-3.72 (m, 2H, H-2, H-5'), 4.16-4.18 (m, 1H, H-4), 4.24-4.27 (m, 1H, H-3), 5.61-5.62 (d, J=5.5 Hz, 1H, H-1); ring IV: δ=2.86-2.91 (dd, J=4.0, 13.0 Hz, 1H, H-6), 3.09 (m, 1H, H-2), 3.41-3.51 (m, 1H, H-4), 3.67-3.73 (m, 3H, H-3, H-5, H-6'), 4.95 (d, J=1.5 Hz, 1H, H-1) ppm.

$^{13}$C NMR (125 MHz, CDCl$_3$): δ=30.3, 32.4 (C-2), 51.2 (C-6'), 55.2 (C-6''), 57.4, 58.5, 59.8, 60.4, 63.2, 69.5, 70.9, 71.0, 71.2, 71.9, 72.4, 73.0, 74.2, 74.3, 74.5, 75.0, 75.2, 78.1, 79.5, 79.7, 81.6, 82.1, 83.8, 96.2 (C-1'''), 98.2 (C-1'), 107.1 (C-1''), 113.7, 113.8, 114.0, 129.4, 129.51, 129.8, 130.0, 159.1, 159.2, 159.5 ppm.

MALDI TOFMS calcd for C$_{74}$H$_{84}$N$_{18}$O$_{19}$Na ([M+Na]$^+$): m/e=1551.8; measured m/e=1551.4.

Preparation of 5''-(Prop-2-ynyloxy)-neomycin (Compound 3a)

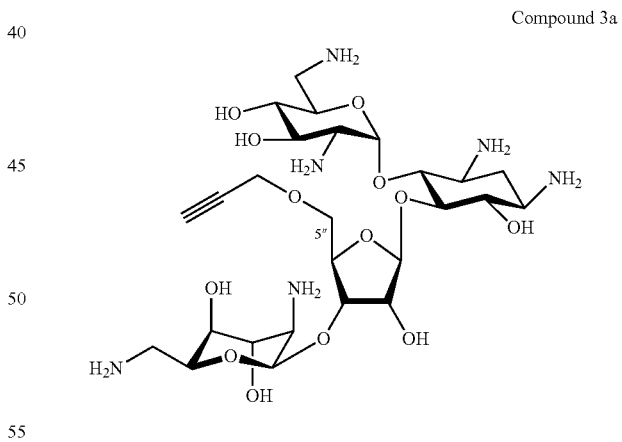

Compound 3a

Compound 6 (0.43 grams, 0.28 mmol) was dissolved in acetonitrile (5 ml) and after stirring at −4° C. for 10 minutes, cerium (IV) ammonium nitrate (CAN) (1.0 grams, 1.82 mmol) in 0.5 ml of water was added. The reaction progress was monitored by TLC (EtOAc/Hexane, 4:5, and EtOAc, 100%). After 3 hours, the reaction mixture was diluted with EtOAc (100 ml) and washed with brine. The combined organic layer was dried over MgSO$_4$, evaporated to dryness and used for the next step without further purification.

The crude product from the previous step was dissolved in THF (7 ml), NaOH 0.1M (1.5 ml) and stirred at 60° C. for 10 minutes after which PMe$_3$ (1 M solution in THF, 4.0 ml, 4.0 mmol) was added. The reaction progress was monitored by TLC (CH$_2$Cl$_2$/MeOH/H$_2$O/MeNH$_2$ (33% solution in EtOH), 10:15:6:15), which indicated completion after 3.5 hours. The reaction mixture was purified by flash chromatography on a short column of silica gel and the column was washed as follows: THF, EtOH, MeOH, and finally with MeNH$_2$ (33% solution in EtOH). The fractions containing the product were combined and evaporated to dryness, re-dissolved in water and evaporated again to afford Compound 3a as a free amine (162.5 mg, 89% for both steps). This product was then dissolved in water, the pH was adjusted to 7.5 with 0.01 M H$_2$SO$_4$ and lyophilized to give the sulfate salt of Compound 3a (220 mg) as a white foamy solid.

$^1$H NMR (500 MHz, D$_2$O, pH=3.0): δ=2.96 (m, 1H, CH of triple bond), 4.23-4.28 (m, 2H, CH$_2$ of linker); ring I: δ=3.27-3.51 (m, 4H, H-2, H-4, H-6, H-6'), 3.82-3.93 (m, 2H, H-3, H-5), 6.07-6.08 (d, J=4.0 Hz, 1H, H-1); ring II: δ=1.96-2.03 (ddd, J$_1$=J$_2$=J$_3$=12.5 Hz, 1H, H-2ax), 2.37-2.41 (dt, J=4.0, 12.5 Hz, 1H, H-2eq), 3.27-3.51 (m, 2H, H-1, H-3), 3.64-3.69 (m, 1H, H-5), 4.00-4.04 (t, J=9.5 Hz, 1H, H-6), 4.14-4.17 (t, J=9.5 Hz, 1H, H-4); ring III: δ=3.64-3.69 (m, 1H, H-5), 3.82-3.93 (m, 1H, H-5'), 4.23-4.28 (m, 1H, H-4), 4.40 (dd, J=2.0, 4.0 Hz, 1H, H-2), 4.47-4.49 (dd, J=4.0, 7.0 Hz, 1H, H-3), 5.36 (s, 1H, H-1); ring IV δ$_H$ δ 3.08-3.13 (dd, J=8.5, 13.5 Hz, 1H, H-6), 3.27-3.51 (m, 2H, H-2, H-6'), 3.75 (m, 1H, H-4), 4.14-4.17 (m, 1H, H-3), 4.23-4.28 (m, 1H, H-5), 5.22 (s, 1H, H-1) ppm.

$^{13}$C NMR (125 MHz, D$_2$O): δ=29.6 (C-2), 42.2 (C-6'), 42.5 (C-6'''), 50.2, 51.6, 52.6, 55.3, 60.3, 68.9, 69.4, 69.6, 71.3, 72.1, 73.2, 74.1, 74.9, 76.2, 77.2, 78.9, 81.1 (CH of triple bond), 81.6, 87.1, 96.4 (C-1'''), 96.9 (C-1'), 112.5 (C-1'') ppm.

MALDI TOFMS calcd for C$_{26}$H$_{49}$N$_6$O$_{13}$ ([M+H]$^+$): m/e=653.3; measured m/e=653.3.

Preparation of 1,3,2',6',2''',6''-Hexaazido-6,3',4',2'',3''',4'-hexaacetoxy-neomycin-4''-carboxylic acid (Compound 8)

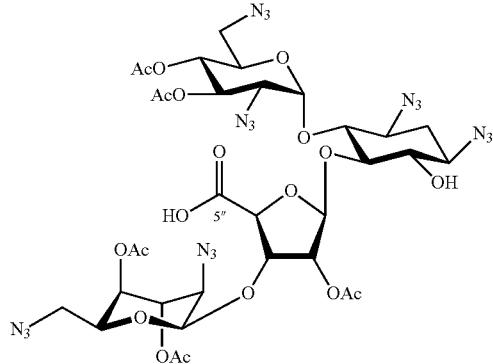

Compound 8

Compound 7 (0.43 gram, 0.42 mmol, prepared according to Fridman, 2003 #301) was dissolved in CH$_2$Cl$_2$ (30 ml) and cooled to 5° C. Thereafter, water (2.5 ml), TEMPO (0.013 grams, 0.08 mmol) and BAIB (0.34 grams, 1.06 mmol) were added. The reaction mixture was stirred at 5° C. for 40 minutes and then allowed slowly to warm to room temperature. The reaction progress was monitored by TLC with two solvent systems (EtOAc/Hexane, 1:1, and MeOH/CHCl$_3$, 1:9), which indicated completion after 4.5 hours. The mixture was cooled to 0° C., diluted with EtOAc, quenched with Na$_2$S$_2$O$_3$, and washed with brine. The combined organic layer was dried over MgSO$_4$, evaporated and purified by flash chromatography (silica gel, MeOH/CHCl$_3$) to yield Compound 8 (320 mg, 76% yield).

$^1$H NMR (500 MHz, CDCl$_3$): δ=2.04 (s, 3H, OAc), 2.06 (s, 3H, OAc), 2.12 (s, 3H, OAc), 2.13 (s, 3H, OAc), 2.15 (s, 3H, OAc), 2.16 (s, 3H, OAc); ring I: δ=3.27-3.44 (m, 1H, H-2), 3.50-3.57 (m, 2H, H-6, H-6'), 4.41-4.43 (m, 1H, H-5), 5.00 (t, J=9.5 Hz, 1H, H-4), 5.43 (t, J=10.5 Hz, 1H, H-3), 6.12 (s, 1H, H-1); ring II: δ=1.63 (ddd, J$_1$=J$_2$=J$_3$=12.5 Hz, 1H, H-2ax), 2.37 (dt, J=3.5, 12.5 Hz, 1H, H-2eq), 3.27-3.44 (m, 2H, H-1, H-3), 3.73 (t, J=9.0 Hz, 1H, H-5), 3.96 (t, J=9.0 Hz, 1H, H-4), 4.93-4.97 (m, 1H, H-6); ring III δ$_H$ 4.71 (m, 1H, H-3), 4.81 (t, J=5.0 Hz, 1H, H-2), 4.87 (d, J=3.0 Hz, 1H, H-4), 5.54 (d, J=5.0 Hz, 1H, H-1); ring IV: δ=3.27-3.44 (m, 3H, H-2, H-6, H-6'), 4.05-4.07 (m, 1H, H-5), 4.71 (m, 1H, H-4), 4.95 (s, 1H, H-1), 5.05 (t, J=2.5 Hz, 1H, H-3) ppm.

$^{13}$C NMR (125 MHz, CDCl$_3$): δ=20.4, 20.7, 20.8, 21.0, 31.2 (C-2), 50.5 (C-6''), 50.9 (C-6'), 57.2, 58.0, 59.0, 60.7, 65.7, 68.6, 69.1, 69.3, 69.8, 73.0, 74.6, 75.2, 76.0, 79.3, 81.8, 96.5 (C-1'), 100.3 (C-1''), 106.3 (C-1''), 168.6, 169.7, 169.8, 170.1, 170.2 ppm.

MALDI TOFMS calcd for C$_{35}$H$_{44}$N$_{18}$O$_{20}$K ([M+K]$^+$): m/e=1075.3; measured m/e=1075.4.

Preparation of 1,3,2',6',2''',6''''-Hexaazido-6,3',4',2'',3''',4'''-hexaacetoxy-4''-(prop-2-ynylcarbamoyl)-neomycin (Compound 9a)

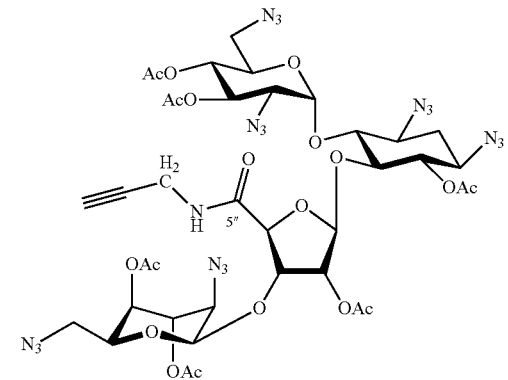

Compound 9a

Compound 8 (2.68 grams, 2.59 mmol) was dissolved in CH$_2$Cl$_2$ (35 ml), then DCC (0.53 grams, 2.57 mmol) and HOBT (0.25 grams, 1.85 mmol) were added at 0° C. The reaction mixture was stirred at 0° C. for 1 hour, allowed slowly to warm to room temperature, and then added with propargyl amine (0.43 grams, 7.81 mmol). Progress of the reaction was monitored by TLC with two solvent systems (EtOAc/Hexane, 1:1 and MeOH/CHCl$_3$, 1:9), which indicated completion after 4 hours. The mixture was diluted with EtOAc and washed with brine. The combined organic layer was dried over MgSO$_4$, evaporated and purified by flash chromatography (silica gel, EtOAc/Hexane) to afford Compound 9a (2.0 grams, 72% yield).

$^1$H NMR (500 MHz, CDCl$_3$): δ=2.07 (s, 3H, OAc), 2.10 (s, 3H, OAc), 2.13 (s, 6H, OAc), 2.17 (s, 3H, OAc), 2.19 (s, 3H, OAc), 2.25-2.26 (t, J=2.5 Hz, 1H, CH of triple bond), 3.91-3.95 (m, 1H, CH$_2$ of linker), 4.14-4.17 (m, 1H, CH$_2$ of linker), 7.41-7.44 (t, J=6.0 Hz, 1H, NH); ring I: δ=3.23-3.26 (dd, J=3.0, 10.0 Hz, 1H, H-2), 3.31-3.44 (m, 2H, H-6, H-6'), 4.46-4.49 (m, 1H, H-5), 4.99-5.09 (m, 1H, H-4), 5.50-5.54 (dd, J=9.0, 11.0 Hz, 1H, H-3), 5.97-5.98 (d, J=4.0 Hz, 1H, H-1); ring II δ$_H$ 1.62-1.70 (ddd, J$_1$=J$_2$=J$_3$=12.5 Hz, 1H, H-2ax), 2.39-2.43 (dt, J=4.0, 12.5 Hz, 1H, H-2eq), 3.31-3.44 (m, 1H, H-3), 3.54-3.58 (m, 1H, H-1), 3.74-3.78 (t, J=9.0 Hz, 1H, H-4), 3.99-4.02 (t, J=9.0 Hz, 1H, H-5), 4.99-5.09 (m, 1H, H-6); ring III: δ=4.57-4.60 (t, J=6.0 Hz, 1H, H-2), 4.65-4.66 (dd, J=3.5, 6.0 Hz, 1H, H-3), 4.82 (d, J=4.0 Hz, 1H, H-4), 5.59-5.61 (d, J=6.0 Hz, 1H, H-1); ring IV: δ=3.31-3.44 (m, 2H, H-2, H-6), 3.54-3.58 (m, 1H, H-6'), 4.09-4.13 (m, 1H, H-5), 4.71-4.72 (t, J=2.0 Hz, 1H, H-4), 4.99-5.09 (m, 2H, H-1, H-3) ppm.

$^{13}$C NMR (125 MHz, CDCl$_3$): δ=22.1, 22.5, 22.7, 22.8, 30.6 (CH$_2$ of linker), 33.2 (C-2), 52.4 (C-6'), 52.7 (C-6'), 59.2, 59.9, 60.9, 62.0, 67.4, 70.6, 71.0, 71.1, 71.2, 73.5, 74.8, 75.8, 76.9, 77.7, 80.4 (CH of triple bond), 80.9, 83.1, 83.3, 99.0 (C-1'''), 102.3 (C-1'), 106.7 (C-1''), 170.1, 170.4, 171.4, 171.8, 171.9 ppm.

MALDI TOFMS calcd for C$_{38}$H$_{47}$N$_{19}$O$_{19}$Na ([M+Na]$^+$): m/e=1096.3; measured m/e=1096.3.

Preparation of 4"-(Prop-2-ynylcarbamoyl)-neomycin (Compound 3b)

Compound 3b

Compound 9a (2.4 grams, 2.27 mmol) was dissolved in 33% solution of MeNH$_2$ in EtOH (40 ml) and the mixture was stirred at room temperature for 30 hours. The reagent and the solvent were removed by evaporation and the residue was dissolved in THF (50 ml), NaOH 0.1M (3 ml) and stirred at 60° C. for 10 minutes after which PMe$_3$ (1M solution in THF, 21.9 mL, 21.9 mmol) was added. Propagation of the reaction was monitored by TLC [CH$_2$Cl$_2$/MeOH/H$_2$O/MeNH$_2$ (33% solution in EtOH), 10:15:6:15], which indicated completion after 3.5 hours. The reaction mixture was purified by flash chromatography on a short column of silica gel and the column was washed as follows: THF, EtOH, MeOH, and finally with MeNH$_2$ (33% solution in EtOH). The fractions containing the product were evaporated under vacuum, re-dissolved in water and evaporated again to afford Compound 3b as a free amine (1.39 grams, 92% yield). This product was then dissolved in water, the pH was adjusted to 7.5 with 0.01 M H$_2$SO$_4$ and lyophilized to give the sulfate salt of Compound 3b (1.88 grams) as a white foamy solid.

$^1$H NMR (500 MHz, D$_2$O, pH=3.17): δ=2.59-2.60 (t, J=2.5 Hz, 1H, CH of triple bond), 3.86-4.02 (m, 2H, CH$_2$ of linker); ring I: δ=3.20-3.24 (dd, J=3.5, 13.5 Hz, 1H, H-6), 3.25-3.37 (m, 3H, H-2, H-4, H-6'), 3.86-4.02 (m, 2H, H-3, H-5), 6.03-6.04 (d, J=4.0 Hz, 1H, H-1); ring II: δ=1.92-1.98 (ddd, J$_1$=J$_2$=J$_3$=12.5 Hz, 1H, H-2ax), 2.37-2.41 (dt, J=4.0, 12.5 Hz, 1H, H-2eq), 3.25-3.37 (m, 1H, H-1), 3.45-3.50 (m, 1H, H-3), 3.67-3.71 (m, 1H, H-5), 3.86-4.05 (m, 1H, H-6), 4.15-4.19 (t, J=9.5 Hz, 1H, H-4); ring III: δ=4.42-4.43 (dd, J=2.0, 4.5 Hz, 1H, H-3), 4.47-4.48 (d, J=7.5 Hz, 1H, H-4), 4.60-4.62 (dd, J=4.5, 7.5 Hz, 1H, H-2), 5.44 (s, 1H, H-1); ring IV: δ=3.13-3.17 (dd, J=8.0, 13.5 Hz, 1H, H-6), 3.38-3.41 (dd, J=3.0, 13.5 Hz, 1H, H-6'), 3.53 (m, 1H, H-2), 3.67-3.71 (m, 1H, H-4), 4.15-4.19 (m, 1H, H-3), 4.20-4.23 (m, 1H, H-5), 5.20 (s, 1H, H-1) ppm.

$^{13}$C NMR (125 MHz, D$_2$O): δ=29.6 (C-2), 30.7, 42.1 (C-6'), 42.2 (C-6'), 50.2, 51.8, 52.5, 55.4, 68.7, 69.3, 69.5, 71.4, 72.5, 72.9, 74.0, 74.7, 76.4, 79.4, 80.9, 81.2 (CH of triple bond), 86.4, 96.5 (C-1'''), 97.0 (C-1'), 112.3 (C-1''), 173.0 (CO) ppm.

MALDI TOFMS calcd for C$_{26}$H$_{47}$N$_7$O$_{13}$K ([M+K]$^+$): m/e=704.2; measured m/e=704.3.

Preparation of 1,3,2',6',2''',6'''-Hexaazido-6,3',4',2'', 3'',4'''-hexaacetoxy-4''-(4-ethynylphenylcarbamoyl)-neomycin (Compound 9b)

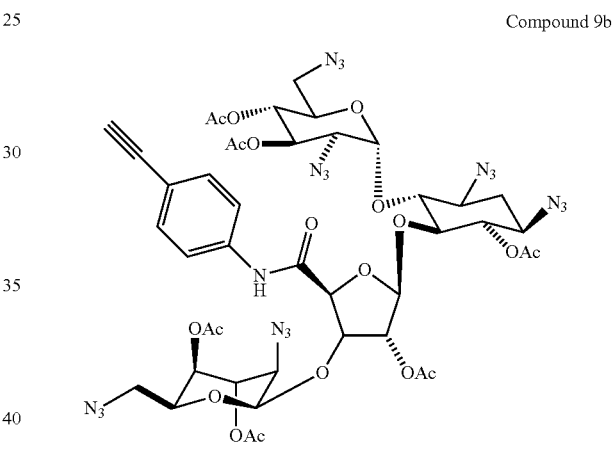

Compound 9b

Compound 9b was prepared as was described hereinabove in the preparation of Compound 9a with the following quantities: Compound 8 (1.67 grams, 1.61 mmol), DCC (0.33 grams, 1.61 mmol), HOBT (0.22 grams, 1.61 mmol), 4-ethynylaniline (0.57 grams, 4.8 mmol), DCM (20 ml), to afford 1.57 grams of Compound 9b (86% yield).

$^1$H NMR (300 MHz, CDCl$_3$): δ=2.00 (s, 3H, OAc), 2.02 (s, 3H, OAc), 2.09 (s, 3H, OAc), 2.10 (s, 3H, OAc), 2.11 (s, 3H, OAc), 2.15 (s, 3H, OAc), 3.00 (s, 1H, CH of triple bond), 7.37-7.40 (m, 2H, aromatic), 7.47-7.50 (m, 2H, aromatic), 8.60 (s, 1H, NH); ring I: δ=3.09-3.18 (m, 2H, H-2, H-6), 3.25-3.26 (m, 1H, H-6'), 4.38-4.44 (m, 1H, H-5), 5.03-5.04 (m, 1H, H-4), 5.39-5.45 (dd, J=9.0, 10.5 Hz, 1H, H-3), 5.92-5.93 (d, J=4.0 Hz, 1H, H-1); ring II: δ=1.91-1.94 (ddd, J$_1$=J$_2$=J$_3$=12.5 Hz, 1H, H-2ax), 2.34-2.38 (dt, J=4.0, 12.5 Hz, 1H, H-2eq), 3.31-3.53 (m, 2H, H-1, H-3), 3.66-3.72 (t, J=9.0 Hz, 1H, H-4), 3.94-4.00 (t, J=9.0 Hz, 1H, H-5), 4.91-4.97 (t, J=9.0 Hz, 1H, H-6); ring III: δ=4.64-4.75 (m, 2H, H-2, H-3), 4.78-4.80 (d, J=4.2 Hz, 1H, H-4), 5.53-5.55 (d, J=5.0 Hz, 1H, H-1); ring IV: δ=3.25-3.26 (m, 1H, H-2), 3.31-3.54 (m, 2H, H-6, H-6'), 4.04-4.08 (m, 1H, H-5), 4.64-4.75 (m, 2H, H-3, H-4), 5.04 (s, 1H, H-1) ppm.

$^{13}$C NMR (125 MHz, CDCl$_3$): δ=22.1, 22.5, 22.7, 22.8, 33.0 (C-2), 51.0, 52.2 (C-6'), 52.7 (C-6''), 59.1, 59.8, 60.7, 62.2, 67.4, 70.4, 71.0, 71.1, 71.3, 74.9, 75.9, 76.9, 78.2, 78.9, 79.9, 82.7, 83.8, 85.0 (CH of triple bond), 98.9 (C-1'), 101.8 (C-1'''), 107.3 (C-1''), 120.1, 121.7, 134.7, 139.6, 168.5, 170.4, 171.4, 171.5, 171.8, 171.9 ppm.

MALDI TOFMS calcd for $C_{43}H_{49}N_{19}O_{19}Na$ ([M+Na]$^+$): m/e=1158.3; measured m/e=1158.2.

Preparation of
4''-(4-Ethynylphenylcarbamoyl)-neomycin
(Compound 3c)

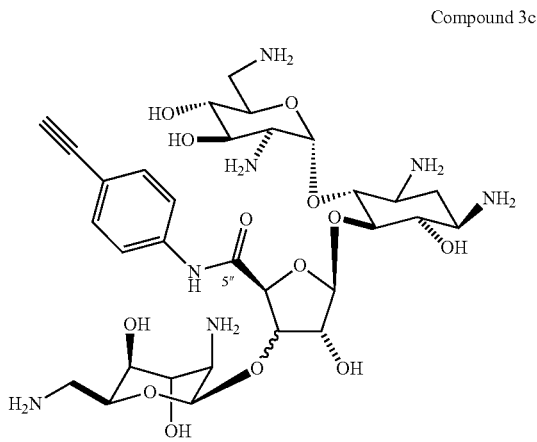

Compound 3c

Compound 3c was prepared as was described in the preparation of Compound 3b with the following quantities: Compound 9b (1.13 grams, 1.00 mmol), MeNH$_2$ (70 ml); Me$_3$P (1 M solution in THF, 8.86 ml, 8.86 mmol), NaOH (0.1 M, 2 ml), THF (20 ml), to afford 0.58 grams of Compound 3c (80% yield).

$^1$H NMR (500 MHz, D$_2$O, pH=3.39): δ=3.42 (s, 1H, CH of triple bond), 7.48-7.52 (m, 4H, aromatic); ring I: δ=3.02-3.07 (dd, J=8.5, 13.5 Hz, 1H, H-6), 3.18-3.22 (dd, $J_1$=$J_2$=9.0 Hz, 1H, H-4), 3.28-3.32 (m, 1H, H-2), 3.37-3.40 (dd, J=3.0, 13.5 Hz, 1H, H-6'), 3.85-3.88 (m, 1H, H-5), 3.96-3.99 (m, 1H, H-3), 6.04-6.05 (d, J=4.0 Hz, 1H, H-1); ring II: δ=1.94-1.98 (ddd, $J_1$=$J_2$=$J_3$=12.5 Hz, 1H, H-2ax), 2.37-2.41 (dt, J=4.0, 12.5 Hz, 1H, H-2eq), 3.28-3.32 (m, 1H, H-1), 3.47-3.50 (m, 1H, H-3), 3.67-3.71 (t, J=10.0 Hz, 1H, H-6), 3.96-3.99 (m, 1H, H-5), 4.16-4.20 (t, J=9.5 Hz, 1H, H-4); ring III: δ=4.48-4.49 (dd, J=2.0, 4.0 Hz, 1H, H-2), 4.64-4.68 (m, 2H, H-3, H-4), 5.47 (s, 1H, H-1); ring IV: δ=2.70-2.74 (dd, J=8.0, 13.5 Hz, 1H, H-6), 2.94-2.97 (dd, J=3.0, 13.5 Hz, 1H, H-6'), 3.55 (m, 1H, H-2), 3.65 (m, 1H, H-4), 4.11-4.15 (m, 2H, H-3, H-5), 5.21 (s, 1H, H-1) ppm.

$^{13}$C NMR (125 MHz, D$_2$O): δ=29.6 (C-2), 41.9 (C-6'), 42.3 (C-6'''), 50.2, 51.8, 52.5, 55.5, 68.6, 69.1, 69.5, 71.3, 72.4, 73.1, 74.1, 75.4, 76.4, 80.2, 80.3, 81.3 (CH of triple bond), 85.0, 86.3, 96.9 (C-1', C-1'''), 112.4 (C-1''), 120.4, 122.7, 135.0, 138.8, 172.0 (CO) ppm.

MALDI TOFMS calcd for $C_{31}H_{49}N_7O_{13}K$ ([M+K]$^+$): m/e=766.3; measured m/e=766.3.

These three NeoB-alkyne Compounds 3a-c were coupled with the Cipro-azide Compounds 2a-i to produce 17 conjugates Compound 1a-q; wherein all compounds were synthesized at a minimum of a 0.05 mmol scale to provide approximately 50 mg of each product (as a free base form).

The coupling reaction between NeoB-alkyne derivatives (Compounds 3a-c) and Cipro-azide derivatives (Compounds 2a-i) was performed under microwave irradiation (about 40 seconds) in the presence of organic base (7% Et$_3$N in water) and the Cu(I) catalyst to ensure the production of a single (anti) stereoisomer at the triazole moiety [30, 34], according to general procedure A described hereinabove. The reaction proceeded almost quantitatively in the presence of 1.2 equivalent of Cipro-azide Compounds 2 and 1 equivalent of NeoB-alkyne Compounds 3. The unreacted Cipro-azide could then be easily separated from the product by passing the reaction mixture through a short column of Amberlite CG-50 (H$^+$ form) resin. Test cases indicated that the protocols presented in General Procedures A-C provided excellent yields of highly pure product. Reaction yields are presented in Table 4 below.

The chemical structures of Compounds 1a-q (see, Table 4 below) were confirmed by a combination of various 1D and 2D NMR techniques, including 2D $^1$H-$^{13}$C HMQC and HMBC, 2D COSY, and 1D selective TOCSY experiments, along with mass spectral analysis.

Compound 1a was prepared according to General Procedure A presented hereinabove, using Compounds 2a and Compound 3c, each prepared and characterized as presented hereinabove.

$^1$H NMR (500 MHz, D$_2$O, pH=3.39): δ=1.05 (m, 2H, cyclopropane), 1.27-1.28 (d, J=7.0 Hz, 2H, cyclopropane), 3.29-3.64 (m, 8H, piperazine; 1H, cyclopropane), 3.80-3.92 (m, 2H, CH$_2$ of linker), 4.91 (m, 2H, CH$_2$ of linker), 7.36-7.38 (d, J=6.0 Hz, 1H, $C_8$—H), 7.51-7.56 (m, 2H, aromatic; 1H, $C_5$—H), 7.65-7.66 (d, J=9.0 Hz, 2H, aromatic), 8.28 (s, 1H, triazole hydrogen), 8.55 (s, 1H, $C_2$—H); aminoglycoside hydrogens: ring I: δ=3.11-3.15 (dd, J=7.0, 13.0 Hz, 1H, H-6), 3.23-3.28 (m, 1H, H-4), 3.29-3.64 (m, 2H, H-2, H-6'), 3.80-3.91 (m, 2H, H-3, H-5), 6.00 (d, J=3.0 Hz, 1H, H-1); ring II: δ=1.78-1.85 (ddd, $J_1$=$J_2$=$J_3$=12.0 Hz, 1H, H-2ax), 2.36-2.39 (dt, J=4.0, 12.0 Hz, 1H, H-2eq), 3.29-3.64 (m, 3H, H-1, H-3, H-6), 3.80-3.91 (m, 1H, H-5), 4.02-4.06 (t, J=10.0 Hz, 1H, H-4); ring III: δ=4.43-4.44 (d, J=4.0 Hz, 1H, H-2), 4.60-4.64 (m, 2H, H-3, H-4), 5.45 (s, 1H, H-1); ring IV: δ=2.70-2.74 (dd, J=7.0, 13.0 Hz, 1H, H-6), 2.91-2.95 (dd, J=3.0, 13.0 Hz, 1H, H-6'), 3.29-3.63 (m, 2H, H-2, H-4), 4.08-4.10 (m, 1H, H-5), 4.11-4.12 (t, J=3.0 Hz, 1H, H-3), 5.20 (s, 1H, H-1) ppm.

$^{13}$C (NMR 125 MHz, D$_2$O): δ=9.2 (cyclopropane), 29.7 (C-2), 37.8, 41.9, 42.0, 46.3, 48.3, 50.1, 51.7, 52.5, 53.4, 55.3, 56.8, 68.6, 69.0, 69.6, 71.3, 72.3, 72.6, 74.3, 75.5, 77.0, 80.4, 81.5, 86.4, 86.4, 97.0 (C-1'''), 97.5 (C-1'), 107.7 (C-1''), 116.9, 119.2, 120.9, 123.0 (CH of triazole), 124.4, 128.4, 138.5, 140.8, 148.9, 150.3, 171.0 (aromatic) ppm.

MALDI TOFMS calculated for $C_{50}H_{70}FN_{13}O_{16}K$ ([M+K]$^+$): m/e=1166.3; measured m/e=1166.5.

Compound 1b was prepared according to General Procedure A presented hereinabove, using Compounds 2b and Compound 3c, each prepared and characterized as presented hereinabove.

$^1$H NMR (500 MHz, D$_2$O, pH=3.2): δ=1.06 (m, 2H, cyclopropane), 1.28-1.29 (d, J=6.0 Hz, 2H, cyclopropane), 2.37-2.41 (m, 2H, CH$_2$ of linker), 3.21-3.65 (m, 8H, piperazine; 1H, cyclopropane; 2H, CH$_2$ of linker), 4.53 (m, 2H, CH$_2$ of linker), 7.36-7.38 (d, J=6.0 Hz, 1H, $C_8$—H), 7.46-7.53 (m, 2H, aromatic; 1H, $C_5$—H), 7.66-7.68 (d, J=9.0 Hz, 2H, aromatic), 8.24 (s, 1H, triazole hydrogen), 8.52 (s, 1H, $C_2$—H); aminoglycoside hydrogens: ring I: δ=3.10-3.15 (dd, J=8.0, 14.0 Hz, 1H, H-6), 3.21-3.65 (m, 3H, H-2, H-4, H-6'), 3.83-3.93 (m, 2H, H-3, H-5), 6.00-6.01 (d, J=4.0 Hz, 1H, H-1); ring II: δ=1.80-1.87 (ddd, $J_1$=$J_2$=$J_3$=13.0 Hz, 1H, H-2ax), 2.37-2.41 (dt, J=4.0, 13.0 Hz, 1H, H-2eq), 3.21-3.65 (m, 2H, H-1, H-3), 3.83-3.93 (m, H-5, H-6), 4.04-4.10 (m, 1H, H-4); ring III: δ=4.43-4.44 (d, J=4.0 Hz, 1H, H-2), 4.59-4.64 (m, 2H, H-3, H-4), 5.46 (s, 1H, H-1); ring IV: δ=2.67-2.72 (dd, J=8.0, 14.0 Hz, 1H, H-6), 2.90-2.94 (dd, J=3.0, 14.0 Hz, 1H, H-6'), 3.21-

3.65 (m, 2H, H-2, H-4), 4.04-4.10 (m, 1H, H-5), 4.11-4.13 (t, J=3.0 Hz, 1H, H-3), 5.20 (s, 1H, H-1) ppm.

$^{13}$C (NMR 125 MHz, D$_2$O): δ=9.2 (cyclopropane), 25.8, 29.7 (C-2), 37.9, 41.9, 42.0, 48.1, 49.14, 50.1, 51.7, 52.6, 53.3, 55.4, 55.5, 68.6, 69.0, 69.7, 71.3, 72.3, 72.6, 74.2, 75.5, 77.0, 80.5, 81.4, 86.4, 97.0 (C-1'''), 97.4 (C-1'), 107.6, 112.6 (C-1''), 116.9, 119.2, 123.1, 124.1 (CH of triazole), 128.3, 128.7, 138.3, 140.8, 148.6, 150.2, 170.9, 171.7 ppm.

MALDI TOFMS calculated for C$_{51}$H$_{72}$FN$_{13}$O$_{16}$K ([M+K]$^+$): m/e=1180.3; measured m/e=1180.4.

Compound 1c was prepared according to General Procedure A presented hereinabove, using Compounds 2c and Compound 3c, each prepared and characterized as presented hereinabove.

$^1$H NMR (500 MHz, D$_2$O, pH=3.1): δ=1.04 (m, 2H, cyclopropane), 1.25-1.30 (d, J=6.0 Hz, 2H, cyclopropane), 1.72-1.80 (m, 2H, CH$_2$ of linker), 1.97-1.99 (m, 2H, CH$_2$ of linker), 3.14-3.66 (m, 8H, piperazine; 1H, cyclopropane; 2H, CH$_2$ of linker), 4.45 (m, 2H, CH$_2$ of linker), 7.32-7.34 (d, J=6.0 Hz, 1H, C$_8$—H), 7.44-7.50 (m, 2H, aromatic; 1H, C$_5$—H), 7.62-7.64 (d, J=8.0 Hz, 2H, aromatic), 8.21 (s, 1H, triazole hydrogen), 8.51 (s, 1H, C$_2$—H), aminoglycoside hydrogens: ring I: δ=3.14-3.66 (m, 4H, H-2, H-4, H-6, H-6'), 3.85-3.95 (m, 2H, H-3, H-5), 6.01-6.02 (d, J=4.0 Hz, 1H, H-1); ring II: δ=1.80-1.87 (ddd, J$_1$=J$_2$=J$_3$=12.0 Hz, 1H, H-2ax), 2.40-2.43 (dt, J=4.0, 12.0 Hz, 1H, H-2eq), 3.14-3.66 (m, 3H, H-1, H-3, H-6), 3.85-3.95 (m, 1H, H-5), 4.04-4.07 (t, J=9.0 Hz, 1H, H-4); ring III: δ=4.44-4.45 (d, J=4.0 Hz, 1H, H-2), 4.59-4.64 (m, 2H, H-3, H-4), 5.48 (s, 1H, H-1); ring IV: δ=2.68-2.72 (dd, J=7.0, 13.0 Hz, 1H, H-6), 2.90-2.94 (dd, J=3.0, 13.0 Hz, 1H, H-6'), 3.14-3.66 (m, 2H, H-2, H-4), 4.09-4.11 (m, 1H, H-5), 4.13-4.14 (t, J=3.0 Hz, 1H, H-3), 5.22 (s, 1H, H-1) ppm.

$^{13}$C (NMR 125 MHz, D$_2$O): g=9.2 (cyclopropane), 22.2 (C-2), 28.2, 29.8, 37.9, 41.9, 42.0, 50.1, 51.5, 51.7, 52.6, 52.9, 55.4, 57.4, 68.6, 69.0, 69.7, 71.3, 72.3, 72.6, 74.2, 75.5, 77.0, 80.5, 81.4, 86.4, 97.0 (C-1'''), 97.5 (C-1'), 107.7, 112.6 (C-1''), 116.9, 119.3, 122.9, 123.9 (CH of triazole), 128.2, 128.6, 138.3, 140.7, 148.5, 170.8, 171.7 ppm.

MALDI TOFMS calculated for C$_{52}$H$_{74}$FN$_{13}$O$_{16}$K ([M+K]$^+$): m/e=1194.3; measured m/e=1194.5.

Compound 1d was prepared according to General Procedure A presented hereinabove, using Compounds 2d and Compound 3c, each prepared and characterized as presented hereinabove.

$^1$H NMR (500 MHz, D$_2$O, pH=3.2): δ=1.04 (m, 2H, cyclopropane), 1.29-1.30 (d, J=6.0 Hz, 2H, cyclopropane), 1.30-1.36 (m, 2H, CH$_2$ of linker), 1.72-1.76 (m, 2H, CH$_2$ of linker), 1.83-1.94 (m, 2H, CH$_2$ of linker), 3.09-3.68 (m, 8H, piperazine; 2H, CH$_2$ of linker), 3.76 (m, 1H, cyclopropane), 4.37-4.40 (t, 2H, CH$_2$ of linker), 7.31-7.33 (d, J=6.0 Hz, 1H, C$_8$—H), 7.38-7.40 (d, J=13.0 Hz, 1H, C$_5$—H), 7.45-7.46 (d, J=8.0 Hz, 2H, aromatic), 7.56-7.57 (d, J=8.0 Hz, 2H, aromatic), 8.17 (s, 1H, triazole hydrogen), 8.49 (s, 1H, C$_2$—H); aminoglycoside hydrogens: ring I: δ=3.09-3.68 (m, 4H, H-2, H-4, H-6, H-6'), 3.85-3.89 (m, 1H, H-5), 3.91-3.95 (m, 1H, H-3), 6.02-6.03 (d, J=4.0 Hz, 1H, H-1); ring II: δ=1.83-1.94 (ddd, J$_1$=J$_2$=J$_3$=12.0 Hz, 1H, H-2ax), 2.39-2.42 (dt, J=4.0, 12.0 Hz, 1H, H-2eq), 3.09-3.68 (m, 3H, H-1, H-3, H-6), 3.91-3.95 (m, 1H, H-5), 4.08-4.12 (m, 1H, H-4); ring III: δ=4.45-4.46 (d, J=4.0 Hz, 1H, H-2), 4.59-4.64 (m, 2H, H-3, H-4), 5.48 (s, 1H, H-1); ring IV: δ=2.68-2.73 (dd, J=8.0, 13.0 Hz, 1H, H-6), 2.92-2.95 (dd, J=3.0, 13.0 Hz, 1H, H-6'), 3.09-3.68 (m, 2H, H-2, H-4), 4.08-4.12 (m, 1H, H-5), 4.13-4.14 (t, J=3.0 Hz, 1H, H-3), 5.22 (s, 1H, H-1) ppm.

$^{13}$C (NMR 125 MHz, D$_2$O): δ=9.2 (cyclopropane), 24.4, 24.5, 29.7 (C-2), 30.5, 37.9, 41.9, 42.1, 50.1, 51.7, 51.9, 52.6, 53.0, 55.4, 58.2, 68.6, 69.0, 69.7, 71.3, 72.4, 72.7, 74.2, 76.9, 80.4, 81.4, 86.3, 96.9 (C-1'''), 97.4 (C-1'), 107.7, 108.4, 112.5 (C-1''), 116.9, 119.3, 122.8, 123.7 (CH of triazole), 128.0, 128.5, 138.3, 140.7, 150.1, 170.8, 171.7, 177.9 ppm.

MALDI TOFMS calculated for C$_{53}$H$_{76}$FN$_{13}$O$_{16}$K ([M+K]$^+$): m/e=1208.3; measured m/e=1208.5.

Compound 1e was prepared according to General Procedure A presented hereinabove, using Compounds 2e and Compound 3c, each prepared and characterized as presented hereinabove.

$^1$H NMR (500 MHz, D$_2$O, pH=3.1): δ=1.02 (m, 2H, cyclopropane), 1.30-1.36 (m, 2H, cyclopropane; 4H, CH$_2$ of linker), 1.71-1.75 (m, 2H, CH$_2$ of linker), 1.85 (m, 2H, CH$_2$ of linker), 3.10-3.71 (m, 8H, piperazine; 4H, CH$_2$ of linker; 1H, cyclopropane), 4.33-4.36 (m, 2H, CH$_2$ of linker), 7.27-7.31 (m, 2H, C$_8$—H, C$_5$—H), 7.41-7.42 (d, J=8.0 Hz, 2H, aromatic), 7.48-7.50 (d, J=8.0 Hz, 2H, aromatic), 8.11 (s, 1H, triazole hydrogen), 8.43 (s, 1H, C$_2$—H); aminoglycoside hydrogens: ring I: δ=3.10-3.71 (m, 4H, H-2, H-4, H-6, H-6'), 3.86-3.90 (m, 1H, H-5), 3.94-3.98 (m, 1H, H-3), 6.04-6.05 (d, J=4.0 Hz, 1H, H-1); ring II: δ=1.91-1.96 (ddd, J$_1$=J$_2$=J$_3$=12.0 Hz, 1H, H-2ax), 2.39-2.42 (dt, J=4.0, 12.0 Hz, 1H, H-2eq), 3.10-3.71 (m, 3H, H-1, H-3, H-6), 3.94-3.98 (m, 1H, H-5), 4.12-4.18 (m, 1H, H-4); ring III: δ=4.47-4.48 (d, J=4.0 Hz, 1H, H-2), 4.57-4.66 (m, 2H, H-3, H-4), 5.50 (s, 1H, H-1); ring IV: δ=2.69-2.74 (dd, J=8.0, 14.0 Hz, 1H, H-6), 2.94-2.97 (dd, J=3.0, 14.0 Hz, 1H, H-6'), 3.10-3.71 (m, 2H, H-2, H-4), 4.12-4.18 (m, 2H, H-3, H-5), 5.22 (s, 1H, H-1) ppm.

$^{13}$C (NMR 125 MHz, D$_2$O): δ=9.2 (cyclopropane), 24.6, 26.8, 29.7 (C-2), 30.8, 37.8, 41.8, 42.2, 48.1, 50.2, 51.8, 52.1, 52.6, 53.0, 55.5, 58.3, 68.6, 69.1, 69.6, 71.3, 72.4, 72.8, 74.1, 75.4, 76.7, 80.2, 81.3, 86.3, 96.8 (C-1'''), 97.2 (C-1'), 107.6, 112.3 (C-1''), 116.9, 119.3, 122.6, 123.5 (CH of triazole), 127.9, 128.4, 138.4, 140.6, 145.7, 148.1, 150.0, 154.0, 170.6, 171.7, 177.7 ppm.

MALDI TOFMS calculated for C$_{54}$H$_{78}$FN$_{13}$O$_{16}$K ([M+K]$^+$): m/e=1222.4; measured m/e=1222.5.

Compound 1f was prepared according to General Procedure A presented hereinabove, using Compounds 2f and Compound 3c, each prepared and characterized as presented hereinabove.

$^1$H NMR (500 MHz, D$_2$O, pH=3.0): δ=1.07 (m, 2H, cyclopropane), 1.31 (m, 2H, cyclopropane), 3.24-3.75 (m, 3H, CH$_2$ of linker; 8H, piperazine; 1H, cyclopropane), 4.49-4.50 (m, 1H, CH$_2$ of linker), 4.63-4.72 (m, 1H, CH$_2$ of linker), 7.34-7.39 (m, 2H, C$_8$—H, C$_5$—H), 7.53-7.54 (d, J=8.0 Hz, 2H, aromatic), 7.67-7.68 (d, J=8.0 Hz, 2H, aromatic), 8.27 (s, 1H, triazole hydrogen), 8.48 (s, 1H, C$_2$—H); aminoglycoside hydrogens: ring I: δ=3.12-3.16 (dd, J=8.0, 14.0 Hz, 1H, H-6), 3.24-3.75 (m, 3H, H-2, H-4, H-6'), 3.87-3.91 (m, 1H, H-5), 3.94-3.98 (m, 1H, H-3), 6.06-6.07 (d, J=4.0 Hz, 1H, H-1); ring II: δ=1.91-1.96 (ddd, J$_1$=J$_2$=J$_3$=12.0 Hz, 1H, H-2ax), 2.41-2.43 (dt, J=4.0, 12.0 Hz, 1H, H-2eq), 3.24-3.75 (m, 3H, H-1, H-3, H-6), 3.94-3.98 (m, 1H, H-5), 4.14-4.19 (m, 1H, H-4); ring III: δ=4.48-4.50 (d, J=4.0 Hz, 1H, H-2), 4.63-4.72 (m, 2H, H-3, H-4), 5.51 (s, 1H, H-1); ring IV: δ=2.74-2.78 (dd, J=8.0, 13.0 Hz, 1H, H-6), 2.96-2.99 (dd, J=3.0, 13.0 Hz, 1H, H-6'), 3.24-3.75 (m, 2H, H-2, H-4), 4.14-4.19 (m, 2H, H-3, H-5), 5.24 (s, 1H, H-1) ppm.

$^{13}$C (NMR 125 MHz, D$_2$O): δ=9.3 (cyclopropane), 29.7 (C-2), 37.9, 41.9, 42.2, 47.9, 50.3, 51.8, 52.6, 55.4, 55.5, 60.3, 65.8, 68.6, 69.1, 69.6, 71.4, 72.4, 72.8, 74.2, 75.4, 76.8, 80.4, 81.4, 97.0 (C-1'''), 97.2 (C-1'), 107.5, 112.5 (C-1''), 117.0, 119.3, 123.0, 125.0 (CH of triazole), 128.2, 138.4, 140.7, 148.5, 150.1, 170.7, 171.8, 177.8 ppm.

MALDI TOFMS calculated for C$_{51}$H$_{72}$FN$_{13}$O$_{17}$K ([M+K]$^+$): m/e=1196.3; measured m/e=1196.3.

Compound 1g was prepared according to General Procedure A presented hereinabove, using Compounds 2g and Compound 3c, each prepared and characterized as presented hereinabove.

$^1$H NMR (500 MHz, D$_2$O, pH=3.1): δ=1.00-1.07 (m, 2H, cyclopropane), 1.29-1.31 (d, J=6.0 Hz, 2H, cyclopropane), 2.96 (m, 2H, CH$_2$ of linker), 3.23-3.59 (m, 8H, piperazine; 1H, cyclopropane), 3.85 (m, 2H, CH$_2$ of linker), 3.97-4.01 (m, 2H, CH$_2$ of linker), 4.59-4.61 (m, 2H, CH$_2$ of linker), 7.08-7.09 (m, 3H, C$_8$—H, aromatic), 7.41-7.43 (d, J=9.0 Hz, 2H, aromatic), 7.55-7.57 (d, J=13.0 Hz, 2H, C$_5$—H), 8.30 (s, 1H, triazole hydrogen), 8.71 (s, 1H, C$_2$—H); aminoglycoside hydrogens: ring I: δ=3.07-3.11 (dd, J=8.0, 14.0 Hz, 1H, H-6), 3.23-3.59 (m, 3H, H-2, H-4, H-6'), 3.87-3.91 (m, 1H, H-5), 3.97-4.01 (m, 1H, H-3), 5.97-5.98 (d, J=4.0 Hz, 1H, H-1); ring II: δ=1.93-2.00 (ddd, J$_1$=J$_2$=J$_3$=13.0 Hz, 1H, H-2ax), 2.41-2.44 (dt, J=4.0, 13.0 Hz, 1H, H-2eq), 3.23-3.59 (m, 2H, H-1, H-3), 3.71-3.75 (t, J=10.0 Hz, 1H, H-6), 3.97-4.01 (m, 1H, H-5), 4.18-4.22 (t, J=10.0 Hz, 1H, H-4); ring III: δ=4.43-4.44 (d, J=5.0 Hz, 1H, H-2), 4.59-4.61 (m, 2H, H-3, H-4), 5.50 (s, 1H, H-1); ring IV: δ=2.54-2.58 (dd, J=9.0, 14.0 Hz, 1H, H-6), 2.87-2.90 (dd, J=3.0, 14.0 Hz, 1H, H-6'), 3.23-3.59 (m, 2H, H-2, H-4), 4.07-4.09 (m, 1H, H-5), 4.12-4.13 (t, J=3.0 Hz, 1H, H-3), 5.18 (s, 1H, H-1) ppm.

$^{13}$C (NMR 125 MHz, D$_2$O): δ=9.3 (cyclopropane), 9.4 (cyclopropane), 29.6 (C-2), 38.0, 41.7, 42.2, 50.3, 51.8, 52.2, 52.6, 52.8, 55.6, 56.1, 65.7, 68.4, 68.9, 69.7, 70.0, 71.3, 72.5, 72.9, 73.9, 75.3, 76.1, 79.9, 81.0, 85.8, 96.6 (C-1''), 96.8 (C-1'), 107.9, 111.5 (C-1'''), 113.1, 116.9, 121.1, 122.2, 124.2 (CH of triazole), 127.7, 138.5, 140.6, 145.7, 148.4, 150.4, 154.1, 156.1, 171.0, 171.3, 178.2 ppm.

MALDI TOFMS calculated for C$_{52}$H$_{74}$FN$_{13}$O$_{17}$K ([M+K]$^+$): m/e=1210.3; measured m/e=1210.2.

Compound 1h was prepared according to General Procedure A presented hereinabove, using Compounds 2h and Compound 3c, each prepared and characterized as presented hereinabove.

$^1$H NMR (500 MHz, D$_2$O, pH=3.2): δ=0.91-0.92 (m, 2H, cyclopropane), 1.18-1.22 (m, 2H, cyclopropane), 3.23-3.47 (m, 8H, piperazine; 1H, cyclopropane), 4.37-4.43 (m, 2H, CH$_2$ of linker), 5.42-5.52 (m, 2H, CH$_2$ of linker), 6.33-6.35 (d, J=9.0 Hz, 1H, C$_8$—H), 6.92-6.93 (d, J=6.0 Hz, 1H, C$_5$—H), 7.02-7.08 (dd, J$_1$=8.0, J$_2$=12.0 Hz, 4H, aromatic), 7.53-7.54 (d, J=7.0 Hz, 1H, aromatic), 7.58 (s, 1H, triazole hydrogen), 7.62-7.65 (t, J=8.0 Hz, 1H, aromatic), 7.71-7.72 (d, J=7.0 Hz, 1H, aromatic), 8.21-8.22 (m, 2H, C$_2$—H, aromatic); aminoglycoside hydrogens: ring I: δ=3.07-3.11 (dd, J=8.0, 14.0 Hz, 1H, H-6), 3.23-3.47 (m, 3H, H-2, H-4, H-6'), 3.84-3.88 (m, 1H, H-5), 3.90-3.95 (m, 1H, H-3), 5.95-5.96 (d, J=4.0 Hz, 1H, H-1); ring II: δ=1.79-1.87 (ddd, J$_1$=J$_2$=J$_3$=13.0 Hz, 1H, H-2ax), 2.35-2.38 (dt, J=4.0, 13.0 Hz, 1H, H-2eq), 3.23-3.47 (m, 2H, H-1, H-3), 3.61-3.65 (t, J=10.0 Hz, 1H, H-6), 3.90-3.95 (m, 1H, H-5), 4.01-4.07 (t, J=10.0 Hz, 1H, H-4); ring III: δ=4.37-4.43 (m, 2H, H-2, H-4), 4.50-4.53 (dd, J=4.0, 8.0 Hz, 1H, H-3), 5.42 (d, J=1.0 Hz, 1H, H-1); ring IV: δ=2.47-2.51 (dd, J=8.0, 13.0 Hz, 1H, H-6), 2.80-2.83 (dd, J=3.0, 13.0 Hz, 1H, H-6'), 3.23-3.47 (m, 1H, H-4), 3.53-3.54 (m, 1H, H-2), 4.01-4.07 (m, 2H, H-3, H-5), 5.14 (s, 1H, H-1) ppm.

$^{13}$C (NMR 125 MHz, D$_2$O): δ=9.2 (cyclopropane), 24.5 (CH$_2$ of linker), 29.9 (C-2), 37.7, 41.7, 42.1, 47.9, 50.2, 50.9, 51.8, 52.5, 55.5, 55.6, 60.8, 68.4, 68.9, 69.7, 71.3, 72.3, 72.8, 74.1, 75.4, 76.9, 80.1, 81.1, 86.2, 96.6 (C-1'''), 97.3 (C-1'), 107.4, 112.0 (C-1''), 116.9, 119.2, 121.0, 123.3, 127.2, 127.6, 129.6, 131.6, 133.2, 134.4 (CH of triazole), 134.8, 137.7, 138.4, 140.1, 148.0, 149.2, 170.4, 171.4, 176.5 ppm.

MALDI TOFMS calculated for C$_{56}$H$_{74}$FN$_{13}$O$_{16}$K ([M+K]$^+$): m/e=1242.4; measured m/e=1242.5.

Compound 1i was prepared according to General Procedure A presented hereinabove, using Compounds 2i and Compound 3c, each prepared and characterized as presented hereinabove.

$^1$H NMR (500 MHz, D$_2$O, pH=3.2): δ=0.90-0.94 (m, 2H, cyclopropane), 1.22-1.24 (m, 2H, cyclopropane), 3.23-3.41 (m, 8H, piperazine; 1H, cyclopropane), 4.38 (m, 2H, CH$_2$ of linker), 5.26-5.37 (m, 2H, CH$_2$ of linker), 6.44-6.46 (d, J=10.5 Hz, 1H, C$_8$—H), 6.90-6.92 (d, J=7.0 Hz, 1H, C$_5$—H), 7.09 (m, 4H, aromatic), 7.50 (m, 4H, aromatic), 8.03 (s, 1H, triazole hydrogen), 8.22 (s, 1H, C$_2$—H); aminoglycoside hydrogens: ring I: δ=3.08-3.11 (dd, J=8.0, 14.0 Hz, 1H, H-6), 3.23-3.41 (m, 3H, H-2, H-4, H-6), 3.84-3.92 (m, 2H, H-3, H-5), 5.93-5.94 (d, J=4.0 Hz, 1H, H-1); ring II: δ=1.75-1.82 (ddd, J$_1$=J$_2$=J$_3$=13.0 Hz, 1H, H-2ax), 2.34-2.37 (dt, J=4.0, 13.0 Hz, 1H, H-2eq), 3.23-3.41 (m, 2H, H-1, H-3), 3.56-3.61 (t, J=10.0 Hz, 1H, H-6), 3.84-3.92 (m, 1H, H-5), 3.97-4.01 (t, J=10.0 Hz, 1H, H-4); ring III: δ=4.38 (m, 1H, H-2), 4.46-4.47 (d, J=8.0 Hz, 1H, H-4), 4.52-4.54 (dd, J=4.0, 8.0 Hz, 1H, H-3), 5.43 (s, 1H, H-1); ring IV: δ=2.47-2.52 (dd, J=8.0, 13.0 Hz, 1H, H-6), 2.80-2.83 (dd, J=3.0, 13.0 Hz, 1H, H-6'), 3.48 (m, 1H, H-4), 3.53-3.54 (m, 1H, H-2), 3.97-4.01 (m, 1H, H-5), 4.07-4.08 (dd, J=2.0, 1H, H-3), 5.14 (s, 1H, H-1) ppm.

$^{13}$C (NMR 125 MHz, D$_2$O): δ=9.2 (cyclopropane), 30.0 (C-2), 37.7, 41.7, 42.1, 48.0, 50.1, 50.8, 51.7, 52.5, 55.5, 60.7, 68.4, 68.9, 69.7, 71.2, 72.7, 74.2, 75.4, 77.2, 80.2, 81.2, 86.3, 96.6 (C-1'''), 97.4 (C-1'), 106.3, 112.3 (C-1''), 116.9, 119.2, 121.0, 122.7 (CH of triazole), 127.1, 127.4, 129.5, 131.3, 134.9, 134.4, 138.7, 140.3, 148.3, 149.3, 170.4, 171.4, 176.7 ppm.

MALDI TOFMS calculated for C$_{56}$H$_{74}$FN$_{13}$O$_{16}$K ([M+K]$^+$): m/e=1242.4; measured m/e=1242.7.

Compound 1j was prepared according to General Procedure A presented hereinabove, using Compounds 2a and Compound 3b, each prepared and characterized as presented hereinabove.

$^1$H NMR (500 MHz, D$_2$O, pH=3.0): δ=1.09 (m, 2H, cyclopropane), 1.32-1.33 (d, J=6.0 Hz, 2H, cyclopropane), 3.25-3.62 (m, 8H, piperazine; 1H, cyclopropane), 3.73-3.74 (m, 2H, CH$_2$ of linker), 4.44-4.56 (m, 2H, CONH—CH$_2$), 4.87-4.89 (t, J=6.0 Hz, 2H, CH$_2$ of linker), 7.33-7.36 (m, 2H, C$_5$—H, C$_8$—H), 8.02 (s, 1H, triazole hydrogen), 8.51 (s, 1H, C$_2$—H); aminoglycoside hydrogens: ring I: δ=3.25-3.62 (m, 5H, H-2, H-3, H-4, H-6, H-6'), 3.86-3.96 (m, 1H, H-5), 6.01-6.02 (d, J=4.0 Hz, 1H, H-1); ring II: δ=1.86-1.93 (ddd, J$_1$=J$_2$=J$_3$=13.0 Hz, 1H, H-2ax), 2.38-2.42 (dt, J=4.0, 13.0 Hz, 1H, H-2eq), 3.25-3.62 (m, 2H, H-1, H-3), 3.66-3.70 (t, J=10.0 Hz, 1H, H-6), 3.86-3.96 (m, 1H, H-5), 4.09-4.13 (t, J=10.0 Hz, 1H, H-4); ring III: δ=4.41-4.42 (dd, J=1.0, 4.0 Hz, 1H, H-2), 4.44-4.56 (m, 1H, H-4), 4.60-4.62 (dd, J=4.0, 7.0 Hz, 1H, H-3), 5.46 (d, J=1.0 Hz, 1H, H-1); ring IV: δ=3.19-3.23 (dd, J=7.0, 14.0 Hz, 1H, H-6), 3.25-3.62 (m, 2H, H-2, H-6'), 3.73-3.74 (m, 1H, H-4), 4.15-4.17 (t, J=3.0 Hz, 1H, H-3), 4.21-4.23 (m, 1H, H-5), 5.22 (d, J=1.0 Hz, 1H, H-1) ppm.

$^{13}$C (NMR 125 MHz, D$_2$O): δ=9.3 (cyclopropane), 29.7 (C-2), 36.1 (CONH—CH$_2$), 37.9, 42.0, 42.1, 46.4, 48.3, 50.2, 51.7, 52.6, 53.7, 55.3, 57.0, 68.9, 69.3, 69.7, 71.4, 72.4, 72.6, 74.1, 74.9, 76.9, 79.6, 81.2, 86.4, 96.9 (C-1'''), 97.4 (C-1'), 107.5, 108.4, 112.4 (C-1''), 116.9, 119.3, 126.5 (CH of triazole), 140.7, 145.9, 150.1, 154.1, 170.8, 172.9, 177.7 ppm.

MALDI TOFMS calculated for C$_{45}$H$_{68}$FN$_{13}$O$_{16}$K ([M+K]$^+$): m/e=1104.2; measured m/e=1104.4.

Compound 1k was prepared according to General Procedure A presented hereinabove, using Compounds 2b and Compound 3b, each prepared and characterized as presented hereinabove.

$^1$H NMR (500 MHz, D$_2$O, pH=3.0): δ=1.07-1.09 (m, 2H, cyclopropane), 1.29-1.31 (d, J=6.0 Hz, 2H, cyclopropane), 2.38-2.41 (m, 2H, CH$_2$ of linker), 3.22-3.61 (m, 8H, piperazine; 1H, cyclopropane), 3.71-3.72 (m, 2H, CH$_2$ of linker), 4.43-4.53 (m, 2H, CH$_2$ of linker; 2H, CONH—CH$_2$), 7.32-7.35 (m, 2H, C$_8$—H, C$_5$—H), 7.94 (s, 1H, triazole hydrogen), 8.50 (s, 1H, C$_2$—H); aminoglycoside hydrogens: ring I: δ=3.23-3.61 (m, 5H, H-2, H-3, H-4, H-6, H-6'), 3.85-3.95 (m, 1H, H-5), 6.00-6.01 (d, J=5.0 Hz, 1H, H-1); ring II: δ=1.86-1.93 (ddd, J$_1$=J$_2$=J$_3$=13.0 Hz, 1H, H-2ax), 2.37-2.42 (dt, J=4.0, 13.0 Hz, 1H, H-2eq), 3.23-3.61 (m, 2H, H-1, H-3), 3.65-3.69 (t, J=10.0 Hz, 1H, H-6), 3.85-3.95 (m, 1H, H-5), 4.10-4.14 (t, J=10.0 Hz, 1H, H-4); ring III: δ=4.40-4.41 (dd, J=2.0, 4.0 Hz, 1H, H-2), 4.43-4.53 (m, 1H, H-4), 4.59-4.61 (dd, J=4.0, 7.0 Hz, 1H, H-3), 5.44 (d, J=2.0 Hz, 1H, H-1); ring IV: δ=3.17-3.21 (dd, J=7.0, 14.0 Hz, 1H, H-6), 3.23-3.61 (m, 2H, H-2, H-6'), 3.71-3.72 (m, 1H, H-4), 4.14-4.15 (t, J=3.0 Hz, 1H, H-3), 4.20-4.22 (m, 1H, H-5), 5.20-5.21 (d, J=1.0 Hz, 1H, H-1) ppm.

$^{13}$C (NMR 125 MHz, D$_2$O): δ=9.2 (cyclopropane), 25.9, 29.7 (C-2), 36.1 (CONH—CH$_2$), 37.9, 42.0, 42.1, 48.2, 49.0, 50.2, 51.7, 52.5, 53.4, 55.3, 55.7, 68.8, 69.3, 69.6, 71.4, 72.4, 72.6, 74.1, 74.8, 76.8, 79.5, 81.1, 86.4, 96.5 (C-1'''), 97.4 (C-1'), 107.4, 108.4, 112.4 (C-1''), 116.9, 119.3, 126.1 (CH of triazole), 140.7, 145.9, 150.1, 154.1, 170.7, 172.9, 177.7 ppm.

MALDI TOFMS calculated for C$_{46}$H$_{70}$FN$_{13}$O$_{16}$K ([M+K]$^+$): m/e=1118.2; measured m/e=1118.4.

Compound 1l was prepared according to General Procedure A presented hereinabove, using Compounds 2d and Compound 3b, each prepared and characterized as presented hereinabove.

$^1$H NMR (500 MHz, D$_2$O, pH=3.1): δ=1.07 (m, 2H, cyclopropane), 1.23-1.30 (m, 2H, cyclopropane; 2H, CH$_2$ of linker), 1.74-1.77 (m, 2H, CH$_2$ of linker), 1.83-1.87 (m, 2H, CH$_2$ of linker), 3.13-3.67 (m, 8H, piperazine; 1H, cyclopropane), 3.69-3.70 (m, 2H, CH$_2$ of linker), 4.32-4.35 (t, J=7.0 Hz, 2H, CH$_2$ of linker), 4.41-4.49 (m, 2H, CONH—CH$_2$), 7.27-7.29 (d, J=6.0 Hz, 1H, C$_8$—H), 7.34 (m, 1H, C$_5$—H), 7.87 (s, 1H, triazole hydrogen), 8.46 (s, 1H, C$_2$—H); aminoglycoside hydrogens: ring I: δ=3.13-3.67 (m, 5H, H-2, H-3, H-4, H-6, H-6'), 3.81-3.95 (m, 1H, H-5), 5.99-6.00 (d, J=4.0 Hz, 1H, H-1); ring II: δ=1.88-1.95 (ddd, J$_1$=J$_2$=J$_3$=13.0 Hz, 1H, H-2ax), 2.36-2.40 (dt, J=4.0, 13.0 Hz, 1H, H-2eq), 3.13-3.67 (m, 3H, H-1, H-3, H-6), 3.81-3.95 (m, 1H, H-5), 4.11-4.14 (t, J=10.0 Hz, 1H, H-4); ring III: δ=4.40-4.41 (dd, J=2.0, 4.0 Hz, 1H, H-2), 4.41-4.49 (m, 1H, H-4), 4.58-4.61 (dd, J=4.0, 7.0 Hz, 1H, H-3), 5.43 (d, J=1.0 Hz, 1H, H-1); ring IV: δ=3.13-3.67 (m, 3H, H-2, H-6, H-6'), 3.69-3.70 (m, 1H, H-4), 4.14-4.15 (t, J=3.0 Hz, 1H, H-3), 4.18-4.21 (m, 1H, H-5), 5.19 (d, J=1.0 Hz, 1H, H-1) ppm.

$^{13}$C (NMR 125 MHz, D$_2$O): δ=9.2 (cyclopropane), 24.5 (CH$_2$ of linker), 29.6 (C-2), 30.6 (CH$_2$ of linker), 36.1 (CONH—CH$_2$), 37.9, 42.1, 48.2, 50.2, 51.7, 51.8, 52.5, 53.1, 55.3, 58.3, 68.8, 69.3, 69.6, 71.4, 72.4, 72.7, 74.0, 74.7, 76.7, 79.4, 81.1, 86.3, 96.5 (C-1'''), 97.3 (C-1'), 107.4, 108.4, 112.3 (C-1''), 116.9, 119.2, 125.8 (CH of triazole), 140.7, 145.4, 145.8, 150.0, 154.0, 156.0, 170.6, 172.9, 177.6 ppm.

MALDI TOFMS calculated for C$_{48}$H$_{74}$FN$_{13}$O$_{16}$K ([M+K]$^+$): m/e=1146.3; measured m/e=1146.6.

Compound 1m was prepared according to General Procedure A presented hereinabove, using Compounds 2f and Compound 3b, each prepared and characterized as presented hereinabove.

$^1$H NMR (500 MHz, D$_2$O, pH=3.1): δ=1.06 (m, 2H, cyclopropane), 1.28-1.29 (d, J=5.0 Hz, 2H, cyclopropane), 3.21-3.54 (m, 3H, CH$_2$ of linker; 8H, piperazine; 1H, cyclopropane), 4.37-4.55 (m, 2H, CH$_2$ of linker; 2H, CONH—CH$_2$), 7.29-7.33 (m, 2H, C$_5$—H, C$_8$—H), 7.92 (s, 1H, triazole hydrogen), 8.47 (s, 1H, C$_2$—H); aminoglycoside hydrogens: ring I: δ=3.21-3.54 (m, 5H, H-2, H-3, H-4, H-6, H-6'), 3.84-3.90 (m, 1H, H-5), 5.97-5.98 (d, J=4.0 Hz, 1H, H-1); ring II: δ=1.82-1.89 (ddd, J$_1$=J$_2$=J$_3$=13.0 Hz, 1H, H-2ax), 2.34-2.37 (dt, J=4.0, 13.0 Hz, 1H, H-2eq), 3.21-3.54 (m, 2H, H-1, H-3), 3.61-3.65 (t, J=10.0 Hz, 1H, H-6), 3.84-3.90 (m, 1H, H-5), 4.06-4.09 (t, J=10.0 Hz, 1H, H-4); ring III: δ=4.37-4.55 (m, 2H, H-2, H-4), 4.57-4.59 (dd, J=4.0, 7.0 Hz, 1H, H-3), 5.41 (d, J=1.0 Hz, 1H, H-1); ring IV: δ=3.13-3.18 (dd, J=8.0, 14.0 Hz, 1H, H-6), 3.21-3.54 (m, 2H, H-2, H-6'), 3.68-3.69 (m, 1H, H-4), 4.11-4.13 (t, J=3.0 Hz, 1H, H-3), 4.17-4.19 (m, 1H, H-5), 5.18 (d, J=1.0 Hz, 1H, H-1) ppm.

$^{13}$C (NMR 125 MHz, D$_2$O): δ=9.2 (cyclopropane), 29.7 (C-2), 36.1 (CONH—CH$_2$), 37.9, 42.0, 42.1, 47.9, 50.2, 51.7, 52.5, 55.2, 55.3, 60.2, 65.8, 68.8, 69.3, 69.6, 71.3, 72.3, 72.6, 74.1, 74.8, 76.8, 79.5, 81.1, 86.4, 96.5 (C-1'''), 97.4 (C-1'), 107.5, 108.3, 112.4 (C-1''), 116.9, 119.2, 126.9 (CH of triazole), 140.7, 145.6, 150.0, 154.0, 170.8, 172.9, 177.7 ppm.

MALDI TOFMS calculated for C$_{46}$H$_{70}$FN$_{13}$O$_{17}$K ([M+K]$^+$): m/e=1134.2; measured m/e=1134.3.

Compound 1n was prepared according to General Procedure A presented hereinabove, using Compounds 2g and Compound 3b, each prepared and characterized as presented hereinabove.

$^1$H NMR (500 MHz, D$_2$O, pH=3.1): δ=1.09 (m, 2H, cyclopropane), 1.32-1.33 (d, J=5.0 Hz, 2H, cyclopropane), 3.21-3.92 (m, 6H, CH$_2$ of linker; 8H, piperazine; 1H, cyclopropane), 4.41-4.56 (m, 2H, CH$_2$ of linker; 2H, CONH—CH$_2$), 7.42-7.44 (m, 2H, C$_5$—H, C$_8$—H), 7.96 (s, 1H, triazole hydrogen), 8.54 (s, 1H, C$_2$—H); aminoglycoside hydrogens: ring I: δ=3.21-3.92 (m, 6H, H-2, H-3, H-4, H-5, H-6, H-6'), 5.96-5.97 (d, J=4.0 Hz, 1H, H-1); ring II: δ=1.87-1.94 (ddd, J$_1$=J$_2$=J$_3$=13.0 Hz, 1H, H-2ax), 2.37-2.41 (dt, J=4.0, 13.0 Hz, 1H, H-2eq), 3.21-3.96 (m, 4H, H-1, H-3, H-5, H-6), 4.11-4.14 (t, J=9.0 Hz, 1H, H-4); ring III: δ=4.36-4.38 (dd, J=2.0, 4.0 Hz, 1H, H-2), 4.41-4.55 (m, 2H, H-3, H-4), 5.33 (d, J=2.0 Hz, 1H, H-1); ring IV: δ=3.13-3.17 (dd, J=7.0, 14.0 Hz, 1H, H-6), 3.21-3.92 (m, 3H, H-2, H-4, H-6'), 4.11-4.14 (t, J=3.0 Hz, 1H, H-3), 4.17-4.19 (m, 1H, H-5), 5.17 (d, J=1.0 Hz, 1H, H-1) ppm.

$^{13}$C (NMR 125 MHz, D$_2$O): δ=9.3 (cyclopropane), 29.6 (C-2), 36.0 (CONH—CH$_2$), 37.9, 42.1, 48.0, 50.2, 51.7, 52.5, 53.4, 55.3, 57.5, 65.7, 68.7, 69.3, 69.6, 70.6, 71.4, 72.4, 72.8, 74.0, 74.7, 76.7, 79.4, 81.0, 86.3, 96.4 (C-1'''), 97.4 (C-1'), 107.6, 108.5, 112.3 (C-1''), 116.9, 119.2, 126.2 (CH of triazole), 140.8, 145.6, 150.2, 154.2, 170.8, 172.9, 177.8 ppm.

MALDI TOFMS calculated for C$_{47}$H$_{72}$FN$_{13}$O$_{17}$K ([M+K]$^+$): m/e=1148.2; measured m/e=1148.4.

Compound 1o was prepared according to General Procedure A presented hereinabove, using Compounds 2h and Compound 3b, each prepared and characterized as presented hereinabove.

$^1$H NMR (500 MHz, D$_2$O, pH=3.2): δ=1.03 (m, 2H, cyclopropane), 1.26-1.27 (d, J=7.0 Hz, 2H, cyclopropane), 3.13-3.47 (m, 8H, piperazine; 1H, cyclopropane), 4.31-4.46 (m, 2H, CH$_2$ of linker; 2H, CONH—CH$_2$), 5.55 (s, 2H, CH$_2$ of linker), 7.31-7.43 (m, 6H, C$_8$—H, C$_5$—H, aromatic), 7.43-7.45 (d, J=8.0 Hz, 2H, aromatic), 7.91 (s, 1H, triazole hydrogen), 8.48 (s, 1H, C$_2$—H); aminoglycoside hydrogens: ring I: δ=3.13-3.47 (m, 4H, H-2, H-4, H-6, H-6'), 3.82-3.87 (m, 2H, H-3, H-5), 5.93-5.94 (d, J=4.0 Hz, 1H, H-1); ring II: δ=1.74-1.82 (ddd, J$_1$=J$_2$=J$_3$=13.0 Hz, 1H, H-2ax), 2.32-2.35 (dt, J=4.0, 13.0 Hz, 1H, H-2eq), 3.13-3.47 (m, 2H, H-1, H-3), 3.58-3.61 (t, J=10.0 Hz, 1H, H-6), 3.82-3.87 (m, 1H, H-5), 3.98-4.01 (t, J=10.0 Hz, 1H, H-4); ring III: δ=4.31-4.46 (m, 2H, H-2, H-4), 4.54-4.56 (dd, J=4.0, 8.0 Hz, 1H, H-3), 5.39 (d, J=1.0 Hz, 1H, H-1); ring IV: δ=3.13-3.47 (m, 3H, H-4, H-6, H-6'), 3.67-3.68 (m, 1H, H-2), 4.10-4.11 (dd, J=3.0 Hz, 1H, H-3), 4.14-4.16 (m, 1H, H-5), 5.16 (d, J=1.0 Hz, 1H, H-1) ppm.

$^{13}$C (NMR 125 MHz, D$_2$O): δ=9.2 (cyclopropane), 30.1 (C-2), 36.0, 37.8, 41.9, 42.1, 48.2, 50.2, 51.7, 52.5, 52.7, 55.2, 55.3, 61.9, 68.8, 69.2, 69.7, 71.2, 72.3, 72.5, 74.2, 74.8, 77.3, 79.5, 81.1, 86.5, 96.6 (C-1'''), 97.4 (C-1'), 108.4, 112.4 (C-1''), 116.9, 119.2, 121.0, 126.1 (CH of triazole), 130.9, 131.5, 131.8, 132.6, 133.3, 137.7, 140.7, 145.7, 150.1, 154.1, 156.1, 171.0, 172.8, 177.7 ppm.

MALDI TOFMS calculated for C$_{51}$H$_{72}$FN$_{13}$O$_{16}$Na ([M+Na]$^+$): m/e=1164.5; measured m/e=1164.6.

Compound 1p was prepared according to General Procedure A presented hereinabove, using Compounds 2i and Compound 3b, each prepared and characterized as presented hereinabove.

$^1$H NMR (500 MHz, D$_2$O, pH=3.1): δ=1.02 (m, 2H, cyclopropane), 1.25-1.26 (d, J=7.0 Hz, 2H, cyclopropane), 3.30-3.53 (m, 8H, piperazine; 1H, cyclopropane), 4.32 (m, 2H, CH$_2$ of linker), 4.40-4.42 (m, 2H, CONH—CH$_2$), 5.54 (s, 2H, CH$_2$ of linker), 7.30-7.35 (m, 4H, C$_8$—H, C$_5$—H, aromatic), 7.43-7.45 (d, J=8.0 Hz, 2H, aromatic), 7.90 (s, 1H, triazole hydrogen), 8.47 (s, 1H, C$_2$—H); aminoglycoside hydrogens: ring I: δ=3.14-3.24 (m, 1H, H-6), 3.30-3.53 (m, 3H, H-2, H-4, H-6), 3.83-3.89 (m, 2H, H-3, H-5), 5.93-5.94 (d, J=4.0 Hz, 1H, H-1); ring II: δ=1.74-1.81 (ddd, J$_1$=J$_2$=J$_3$=13.0 Hz, 1H, H-2ax), 2.32-2.35 (dt, J=4.0, 13.0 Hz, 1H, H-2eq), 3.14-3.24 (m, 1H, H-3), 3.30-3.53 (m, 1H, H-1), 3.58-3.61 (t, J=10.0 Hz, 1H, H-6), 3.83-3.85 (m, 1H, H-5), 3.97-4.01 (t, J=10.0 Hz, 1H, H-4); ring III: δ=4.35-4.36 (dd, J=1.0, 4.0 Hz, 1H, H-2), 4.45 (d, J=8.0 Hz, 1H, H-4), 4.54-4.56 (dd, J=4.0, 8.0 Hz, 1H, H-3), 5.40 (d, J=1.0 Hz, 1H, H-1); ring IV: δ=3.14-3.24 (m, 2H, H-6, H-6'), 3.30-3.53 (m, 1H, H-2), 3.67-3.68 (m, 1H, H-4), 4.10-4.11 (dd, J=3.0 Hz, 1H, H-3), 4.14-4.16 (m, 1H, H-5), 5.16 (d, J=1.0 Hz, 1H, H-1) ppm.

$^{13}$C (NMR 125 MHz, D$_2$O): δ=9.2 (cyclopropane), 30.1 (C-2), 36.0, 37.7, 41.9, 42.1, 48.1, 50.1, 51.7, 52.5, 52.7, 55.1, 55.3, 61.7, 68.8, 69.2, 69.7, 71.2, 72.2, 72.5, 74.2, 74.8, 77.3, 79.5, 81.1, 86.5, 96.6 (C-1'''), 97.5 (C-1'), 108.4, 112.4 (C-1''), 116.9, 119.2, 121.0, 126.1 (CH of triazole), 130.3, 130.5, 133.7, 138.7, 140.6, 145.7, 150.0, 154.0, 170.9, 172.8, 177.7 ppm.

MALDI TOFMS calculated for C$_{51}$H$_{72}$FN$_{13}$O$_{16}$K ([M+K]$^+$): m/e=1180.6; measured m/e=1180.4.

Compound 1q was prepared according to General Procedure A presented hereinabove, using Compounds 2a and Compound 3a, each prepared and characterized as presented hereinabove.

$^1$H NMR (500 MHz, D$_2$O, pH=3.2): δ=1.07 (m, 2H, cyclopropane), 1.30 (m, 2H, cyclopropane), 3.25-3.65 (m, 8H, piperazine), 3.78-3.85 (m, 1H, cyclopropane; 2H, piperazine), 4.68 (m, 2H, CH$_2$ of linker), 4.91 (t, J=7.0 Hz, 2H, CH$_2$ of linker), 7.29-7.31 (m, 2H, C$_8$—H, C$_5$—H), 8.11 (s, 1H, triazole hydrogen), 8.47 (s, 1H, C$_2$—H); aminoglycoside hydrogens: ring I: δ=3.14-3.18 (m, 1H, H-2), 3.25-3.65 (m, 3H, H-4, H-6, H-6'), 3.78-3.85 (m, 2H, H-3, H-5), 5.96 (d, J=4.0 Hz, 1H, H-1); ring II: δ=1.83-1.90 (ddd, J$_1$=J$_2$=J$_3$=13.0 Hz, 1H, H-2ax), 2.36-2.40 (dt, J=4.0, 13.0 Hz, 1H, H-2eq), 3.25-3.65 (m, 2H, H-1, H-3), 3.78-3.85 (m, 1H, H-5), 3.88-3.92 (t, J=10.0 Hz, 1H, H-6), 4.03-4.07 (t, J=10.0 Hz, 1H, H-4); ring III: δ=3.25-3.65 (m, 2H, H-5, H-6), 4.27-4.29 (m, 2H, H-2, H-4), 4.36-4.38 (t, J=5.0 Hz, 1H, H-3), 5.33-5.34 (d, J=1.0 Hz, 1H, H-1); ring IV: δ=3.14-3.18 (m, 1H, H-6), 3.25-3.65 (m, 2H, H-2, H-6'), 3.73 (m, 1H, H-4), 4.11-4.13 (t, J=3.0 Hz, 1H, H-3), 4.18-4.20 (m, 1H, H-5), 5.17 (s, 1H, H-1) ppm.

$^{13}$C (NMR 125 MHz, D$_2$O): δ=9.2 (cyclopropane), 29.7 (C-2), 37.9, 42.1, 42.2, 46.4, 48.2, 50.2, 51.4, 52.6, 53.7, 55.2, 56.9, 65.1, 69.1, 69.3, 69.6, 71.2, 71.5, 71.9, 72.7, 74.1, 75.2, 76.6, 77.9, 81.9, 86.9, 96.7 (C-1'''), 97.3 (C-1'), 107.4, 108.4, 112.3 (C-1''), 116.9, 119.2, 127.5 (CH of triazole), 140.7, 145.8, 150.0, 154.0, 156.0, 170.7, 177.6 ppm.

MALDI TOFMS calculated for C$_{45}$H$_{69}$FN$_{12}$O$_{16}$K ([M+K]$^+$): m/e=1091.2; measured m/e=1091.5. Following the design rational presented hereinabove, the synthesis of a series of kanamycin A-ciprofloxacin conjugates has been carried out as follows. The general approach for the assembly of such structures is similar to that of Cipro-NeoB conjugates, namely a series of alkyne-derivative of kanamycin A, generally referred to herein as Compound 11, has been synthesized, and reacted by "click chemistry" with a series of exemplary azido-derivatives of ciprofloxacin to afford a series of conjugates, according to some embodiments of the present invention, also referred to herein as Cipro-KanA.

Preparation of Compound 11—General Procedure D:

The general synthesis of the Cipro-KanA conjugates (Compound 11), according to some embodiments of the present invention, from Compound 2 (the "Cipro" moiety) and Compound 21 (the "KanA" moiety), is illustrated in Scheme 8 below.

Scheme 8

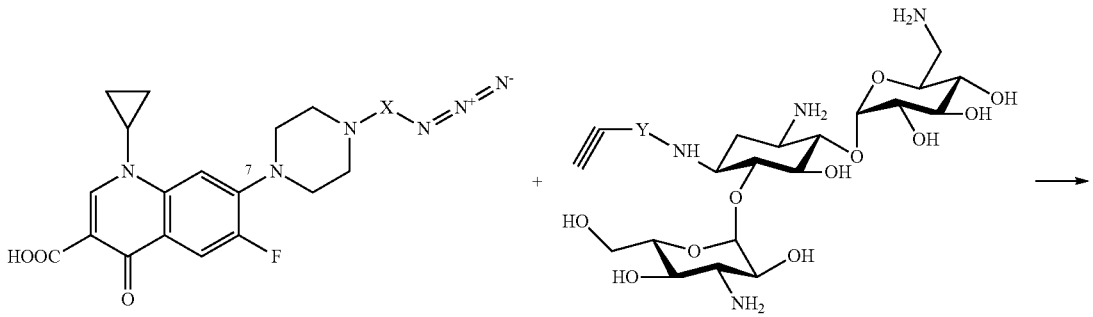

-continued

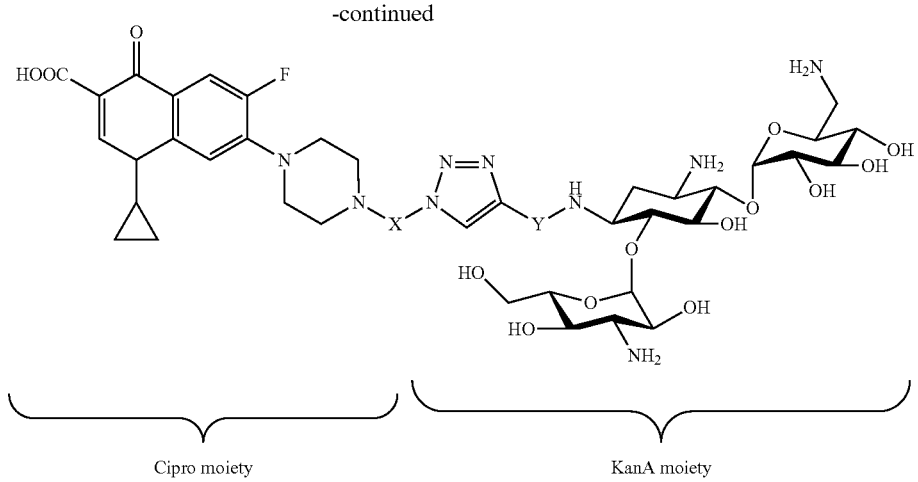

Wherein X and Y represent various first and second spacer moieties respectively, which form the connecting moiety together with the resultant 4-yl-1-yl-1H-1,2,3-triazole linking moiety.

Preparation of Compound 21a:

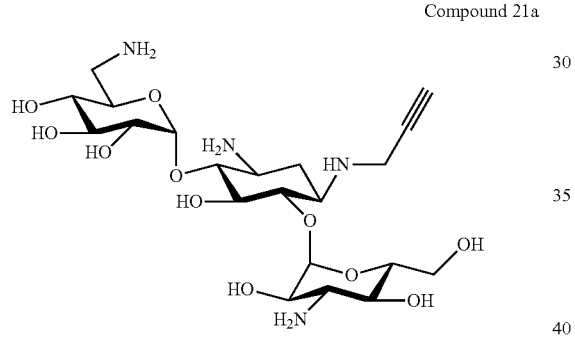

Compound 21a, wherein Y is a methylene (—CH₂—) group, was prepared from commercially available Kanamycin A (Shanghai FWD Chemicals Limited), according to previously published procedure [Yamasaki, T., et al., *J. Antibiot* (Tokyo), 1991, 44, 646].

Briefly, the Kanamycin A derivative, Compound 41, which has only one amine group non-protected at C1-NH— position, was prepared according to Scheme 9 presented below.

Scheme 9

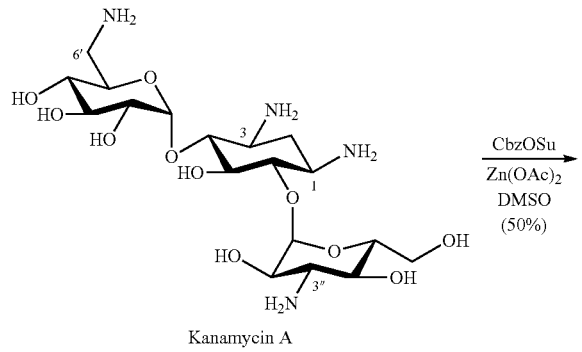

-continued

Selective Cbz protection of two amino groups at C6' and C3 positions of KanA was carried out in the presence of zinc acetate. The use of Zn salt allowed suitable temporary protection of vicinal amino alcohol functions as zinc(II) chelates. Thereafter, unbound amino group reacted with benzyloxycarbonyloxy succinimide to afford the desired protected KanA derivative. Treatment of this compound with ethyl trifluoroacetate in DMSO afforded KanA derivative, Compound 41, selectively unprotected at the C1-NH— position in high yield.

Compound 41 was reacted with propargyl bromide in the presence of $K_2CO_3$ to give protected alkyne derivative of KanA, Compound 31a (Scheme 10). Cleavage of trifluoroacetate group in Compound 31a with methyl amine followed by Cbz deprotection in the presence of HBr in acetic acid afforded desired Compound 21a.

Scheme 10

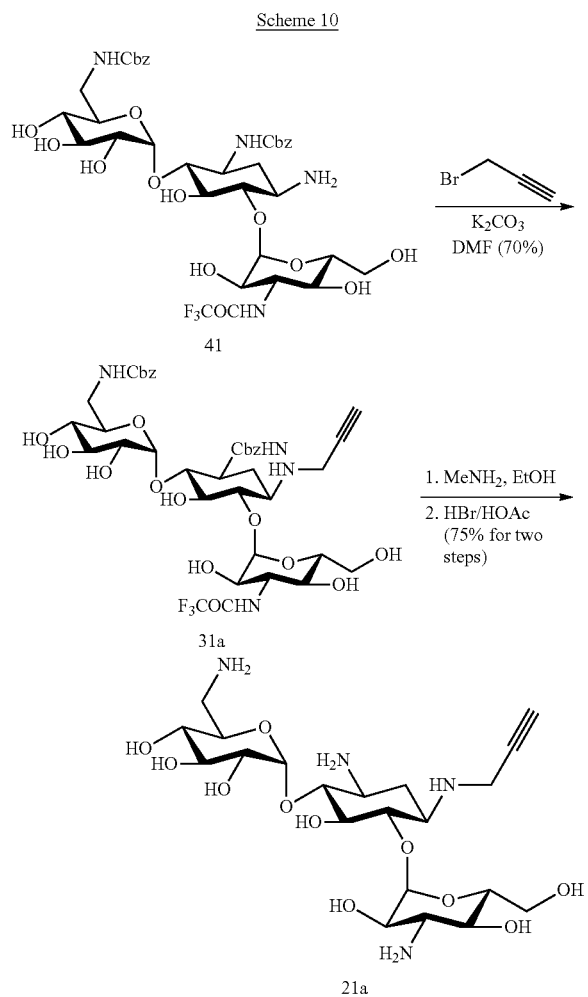

Compound 41 (100 mg, 0.115 mmol) was dissolved in dry DMF (5 ml). Potassium carbonate (19 mg, 0.140 mmol) and propargyl bromide (11.3 μl, 0.126 mmol) were added to the resulted solution at ambient temperature. The reaction propagation was monitored by TLC (MeOH/DCM 1:5), which indicated completion after overnight stiffing. The mixture was transferred on silica column and purified by flash chromatography (silica, MeOH/DCM) to yield the corresponding 1-N-alkilated product: 3,6'-diCbz-3"-trifluoroacetyl-1-prop-2-yn-1-kanamycin A (72 mg, 70% yield).

$^1$H NMR (500 MHz, CD$_3$OD/CDCl$_3$): δ=2.44-2.45 (t, J=2.5 Hz, 1H, CH of triple bond), 3.63-4.08 (m, 2H, —CH$_2$— triple bond), 4.96-5.10 (m, 4H, CH$_2$ of Cbz), 7.23-7.35 (m, 10H, aromatic); ring I: δ=3.37-3.54 (m, 5H, H-2, H-3, H-4, H-6, H-6'), 3.63-4.08 (m, 1H, H-5), 4.96-5.10 (m, 1H, H-1); ring II: δ=1.29-1.36 (ddd, J$_1$=J$_2$=J$_3$=12.5 Hz, 1H, H-2ax), 2.23-2.27 (dt, J=4.0, 12.5 Hz, 1H, H-2eq), 2.96-2.98 (m, 1H, H-1), 3.37-3.54 (m, 1H, H-5), 3.63-4.08 (m, 3H, H-3, H-4, H-6); ring III: δ=3.22-3.26 (dd, J=4.0, 13.0 Hz, 1H, H-6), 3.31-3.34 (m, 1H, H-6'), 3.37-3.54 (m, 2H, H-2, H-4), 3.63-4.08 (m, 2H, H-3, H-5), 4.96-5.10 (m, 1H, H-1) ppm.

$^{13}$C NMR (125 MHz, CD$_3$OD/CDCl$_3$): δ=31.2 (C-2), 35.0 (C-6"), 40.9 (C-6'), 50.1, 55.7, 61.2 (triple bond), 66.7, 66.8, 67.7, 69.7, 70.4, 71.4, 72.5, 72.8, 73.4, 73.9, 75.2, 84.0, 85.5, 100.41 (C-1'), 101.3 (C-1"), 114.87, 117.2, 127.8, 127.9, 128.0, 128.1, 128.4, 136.1, 136.2, 156.5, 157.9, 158.9, 159.2 ppm.

MALDI TOFMS calcd for C$_{39}$H$_{49}$F$_3$N$_4$O$_{19}$Na ([M+Na]$^+$): m/e=909.3; measured m/e=909.3.

The purified product from the above step (100 mg, 0.113 mmol) was dissolved in 33% solution of MeNH$_2$ in EtOH (10 ml) and the mixture was stirred at room temperature for 12 hours. The reagent and the solvent were removed by evaporation and the residue was dissolved in AcOH (2 ml) and stirred at 15° C. for 10 minutes after which 30% solution of HBr in AcOH (0.5 ml) was added. Propagation of the reaction was monitored by TLC (CH$_2$Cl$_2$/MeOH/H$_2$O/MeNH$_2$ (33% solution in EtOH) 10:15:6:15), which indicated completion after 1 hour. 1N NaOH solution was added to the reaction mixture until pH became neutral, then the mixture was purified on a short column of Amberlite CG-50 (H$^+$form). The column was sequentially washed by MeOH, MeOH/MeNH$_2$ (33% solution in EtOH) 95:5, MeOH/MeNH$_2$ (33% solution in EtOH) 9:1 and MeOH/MeNH$_2$ (33% solution in EtOH) 4:1. Fractions containing the product were combined, evaporated, re-dissolved in water and evaporated again to afford the free amine form of the product, Compound 21a (50 mg, 75%). This product was then dissolved in water, the pH was adjusted to 7.5 with 0.01 M H$_2$SO$_4$ and lyophilized to give the sulfate salt of Compound 21a as a white foamy solid.

$^1$H NMR (500 MHz, D$_2$O, pH=3.17): δ=3.00 (t, 1H, CH of triple bond), 3.94-3.98 (dd, J=2.5, 15.5 Hz, 1H, —CH$_2$— triple bond), 4.07-4.11 (dd, J=2.5, 15.5 Hz, 1H, —CH$_2$— triple bond); ring I: δ=3.03-3.08 (dd, J=9.0, 13.5 Hz, 1H, H-6), 3.24-3.28 (t, J=9.5 Hz, 1H, H-4), 3.35-3.38 (dd, J=3.5, 9.0 Hz, 1H, H-6'), 3.60-3.76 (m, 1H, H-2), 3.81-3.93 (m, 2H, H-3, H-5), 5.55-5.56 (d, J=4.0 Hz, 1H, H-1); ring II: δ=1.94-2.01 (ddd, J$_1$=J$_2$=J$_3$=12.5 Hz, 1H, H-2ax), 2.56-2.58 (dt, J=4.0, 12.5 Hz, 1H, H-2eq), 3.40-3.45 (m, 1H, H-3), 3.60-3.76 (m, 1H, H-5), 3.81-3.93 (m, 3H, H-1, H-4, H-6); ring III: δ=3.40-3.45 (m, 1H, H-3), 3.55-3.58 (dd, J=4.0, 10.5 Hz, 1H, H-4), 3.60-3.76 (m, 2H, H-6, H-6'), 3.81-3.93 (m, 2H, H-2, H-5), 5.10-5.11 (d, J=3.0 Hz, 1H, H-1) ppm.

$^{13}$C NMR (125 MHz, D$_2$O): δ=25.4 (C-2), 35.9 (—CH$_2$— triple bond), 40.4 (C-6'), 47.7, 50.0, 54.9, 55.6, 59.8 (C-6"), 65.2, 68.1, 68.6, 70.7, 71.8, 72.4, 73.0, 73.7, 76.9, 78.8, 83.0, 96.0 (C-1'), 100.4 (C-1") ppm.

MALDI TOFMS calcd for C$_{21}$H$_{39}$N$_4$O$_{11}$ ([M+H]$^+$): m/e=523.2; measured m/e=523.3.

Preparation of Compound 11a:

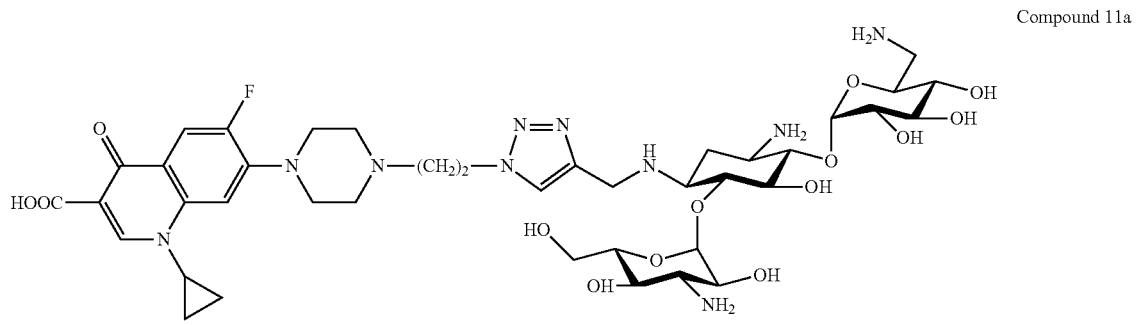

Compound 11a

Compound 11a was prepared according to General Procedure D, presented hereinabove, using Compounds 2a (a ciprofloxacin azido derivatives, see details hereinabove) and Compound 21a.

$^1$H NMR (500 MHz, D$_2$O, pH=3.0): δ=1.17 (m, 2H, cyclopropane), 1.38 (d, J=7.0 Hz, 2H, cyclopropane), 3.62-3.85 (m, 8H, piperazine; 1H, cyclopropane; 2H, CH$_2$ of linker), 4.44-4.47 (d, J=15.0 Hz, 1H, CH$_2$ of linker), 4.61-4.63 (d, J=15.0 Hz, 1H, CH$_2$ of linker), 5.00 (t, J=2.0 Hz, 2H, CH$_2$ of linker), 7.50 (m, 1H, C$_8$—H), 7.56-7.59 (d, J=10.0 Hz, 1H, C$_5$—H), 7.51-7.56, 8.30 (s, 1H, triazole hydrogen), 8.66 (s, 1H, C$_2$—H); aminoglycoside hydrogens: ring I: δ=3.11-3.15 (dd, J=7.0, 13.0 Hz, 1H, H-6), 3.29-3.35 (t, J=9.5 Hz, 1H, H-4), 3.37-3.40 (dd, J=3.5, 9.0 Hz, 1H, H-6'), 3.62-3.85 (m, 3H, H-2, H-3, H-5), 5.50-5.51 (d, J=3.0 Hz, 1H, H-1); ring II: δ=1.92-1.99 (ddd, J$_1$=J$_2$=J$_3$=12.0 Hz, 1H, H-2ax), 2.71-2.75 (dt, J=4.0, 12.0 Hz, 1H, H-2eq), 3.44-3.48 (t, J=10.0 Hz, 1H, H-4), 3.62-3.85 (m, 3H, H-3, H-5, H-6), 3.87-3.90 (td, J=2.0, 10.0 Hz, 1H, H-1); ring III: δ=3.62-3.85 (m, 6H, H-2, H-3, H-4, H-5, H-6, H-6'), 5.07 (s, 1H, H-1) ppm.

$^{13}$C (NMR 151 MHz, D$_2$O): δ=7.6 (cyclopropane), 25.7 (C-2), 36.7, 39.8, 40.4, 44.7, 46.5, 47.7, 52.2, 55.0, 56.4, 60.0, 65.4, 68.3, 68.8, 70.8, 72.3, 72.4, 73.0, 78.2, 83.7, 95.2 (C-1'), 100.9 (C-1'), 106.1, 107.0, 111.2, 115.5, 117.4, 119.4, 127.1 (CH of triazole), 138.5, 139.2, 144.2, 148.7, 152.8, 154.2, 169.3 ppm.

MALDI TOFMS calculated for C$_{40}$H$_{59}$FN$_{10}$O$_{14}$Na ([M+Na]$^+$): m/e=945.8; measured m/e=945.4.

Preparation of Compound 11f:

Compound 11f was prepared according to General Procedure D, presented hereinabove, using Compounds 2f and Compound 21a.

$^1$H NMR (500 MHz, D$_2$O, pH=3.1): δ=1.16 (m, 2H, cyclopropane), 1.38-1.39 (d, J=5.0 Hz, 2H, cyclopropane), 3.28-3.90 (m, 2H, CH$_2$ of linker; 8H, piperazine; 1H, cyclopropane), 4.47-4.49 (d, J=15.0 Hz, 1H, CH$_2$ of linker), 4.50-4.54 (m, 1H, CH of linker), 4.60-4.63 (d, J=15.0 Hz, 1H, CH$_2$ of linker), 4.63-4.65 (m, 2H, CH$_2$ of linker) 7.46-7.49 (m, 2H, C$_5$—H, C$_8$—H), 8.20 (s, 1H, triazole hydrogen), 8.61 (s, 1H, C$_2$—H); aminoglycoside hydrogens: ring I: δ=3.11-3.15 (dd, J=7.0, 13.0 Hz, 1H, H-6), 3.28-3.90 (m, 5H, H-2, H-3, H-4, H-5, H-6'), 5.48-5.49 (d, J=3.0 Hz, 1H, H-1); ring II: δ=1.90-1.97 (ddd, J$_1$=J$_2$=J$_3$=12.0 Hz, 1H, H-2ax), 2.73-2.77 (dt, J=4.0, 12.0 Hz, 1H, H-2eq), 3.28-3.90 (m, 4H, H-3, H-4, H-5, H-6), 3.93-4.00 (td, J=2.0, 10.0 Hz, 1H, H-1); ring III: δ=3.28-3.90 (m, 6H, H-2, H-3, H-4, H-5, H-6, H-6'), 5.05 (s, 1H, H-1) ppm.

$^{13}$C (NMR 151 MHz, D$_2$O): δ=7.4 (cyclopropane), 25.5 (C-2), 36.1, 39.6, 40.2, 46.1, 47.5, 53.5, 54.9, 56.2, 58.4, 59.8, 63.9, 65.2, 68.1, 68.7, 70.6, 72.1, 72.2, 72.8, 78.0, 83.6, 95.7 (C-1'), 100.8 (C-1'), 105.7, 106.6, 112.7, 115.1, 117.4, 127.4 (CH of triazole), 137.8, 138.9, 144.0, 162.7, 169.0 ppm.

MALDI TOFMS calculated for C$_{41}$H$_{61}$FN$_{10}$O$_{15}$Na ([M+Na]$^+$): m/e=975.6; measured m/e=975.4.

Preparation of Compound 11i:

Compound 11i was prepared according to General Procedure D, presented hereinabove, using Compounds 2i and Compound 21a.

$^1$H NMR (500 MHz, D$_2$O, pH=3.2): δ=1.12 (m, 2H, cyclopropane), 1.35-1.36 (m, 2H, cyclopropane), 3.21-3.88 (m, 8H, piperazine; 1H, cyclopropane), 4.42-4.44 (m, 3H, CH$_2$ of linker), 4.58-4.61 (d, J=15.0 Hz, 1H, CH$_2$ of linker), 5.68 (m, 2H, CH$_2$ of linker), 7.42-7.47 (m, 4H, aromatic, C$_5$—H, C$_8$—H), 7.53-7.55 (d, J=10.0 Hz, 2H, aromatic), 8.21 (s, 1H, triazole hydrogen), 8.58 (s, 1H, C$_2$—H); aminoglycoside hydrogens: ring I: δ=3.11-3.15 (dd, J=7.0, 13.0 Hz, 1H, H-6), 3.21-3.88 (m, 5H, H-2, H-3, H-4, H-5, H-6'), 5.48-5.49 (d, J=3.0 Hz, 1H, H-1); ring II: δ=1.85-1.93 (ddd, J$_1$=J$_2$=J$_3$=12.0 Hz, 1H, H-2ax), 2.71-2.75 (dt, J=4.0, 12.0 Hz, 1H, H-2eq), 3.21-3.88 (m, 4H, H-3, H-4, H-5, H-6), 3.94-3.98 (td, J=2.0, 10.0 Hz, 1H, H-1); ring III: δ=3.21-3.88 (m, 6H, H-2, H-3, H-4, H-5, H-6, H-6'), 5.42 (s, 1H, H-1) ppm.

$^{13}$C (NMR 151 MHz, D$_2$O): δ=7.4 (cyclopropane), 25.4 (C-2), 39.7, 40.2, 46.3, 50.9, 53.5, 54.9, 56.2, 59.8, 65.2, 68.1, 68.6, 70.6, 72.1, 72.2, 72.8, 77.9, 83.5, 95.7 (C-1'), 100.8 (C-1'), 105.7, 115.1, 117.4, 119.7, 126.6 (CH of triazole), 128.4, 131.9, 136.7, 137.7, 138.9, 169.0 ppm.

MALDI TOFMS calculated for C$_{41}$H$_{61}$FN$_{10}$O$_{15}$Na ([M+Na]$^+$): m/e=1021.6; measured m/e=1021.4.

Example 2

Antibacterial Activity

Exemplary conjugates, according to some embodiments of the present invention, namely the Cipro-NeoB conjugate Compounds 1a-q, were tested for in vitro antibacterial activity against a panel of susceptible and resistant bacterial strains using non-conjugated Cipro and NeoB as controls (see, Table 4 below). Data for selected Gram-negative and Gram-positive strains are reported as minimal inhibitory concentration (MIC) values. Resistant strains included *Escherichia coli* AG100A and AG100B (Gram-negative), and methicillin-resistant *S. aureus* (MRSA) (ATCC 43300, Gram-positive). *E. coli* AG100A and AG100B are aminoglycosides-resistant laboratory strains that harbor Kan$^r$ transposon Tn903 [35]. MRSA (ATCC 43300) is one of the leading causes of bacterial infections and exerts high level of resistance to aminoglycosides [36].

The MIC values for a set of exemplary conjugates according to some embodiments of the present invention, Compounds 1a-q, were determined using the double-microdilution method according to the National Committee for Clinical Laboratory Standards (NC═CLS) with starting concentration of 384 µg/ml and 1.5 µg/ml of the tested compounds. All the experiments were performed in duplicates and analogous results were obtained in two to four different experiments.

Resistance studies were performed in parallel with *E. coli* ATCC 35218 and *B. subtilis* ATCC 6633 strains in the presence of Cipro, NeoB, Cipro:NeoB mixture (1:1 molar ratio), and Compound 1i. After the initial MIC experiments, MICs were determined once in two days, for 15 passages as follows: for each compound tested, bacteria from the one half MIC well were diluted 100-fold (50 µl of the bacterial growth in the total of 5 ml LB medium) and were grown overnight at 37° C. The OD600 of the bacteria was diluted to yield 5×10$^5$ cells/ml in LB (according to a calibration curve) and used again for MIC determination in the subsequent generation. In parallel, MIC evolution during these subcultures was compared concomitantly with each new generation, using bacteria harvested from control wells (wells cultured without antimicrobial agent from the previous generation). The relative MIC was calculated for each experiment from the ratio of MIC obtained for a given subculture to that obtained for first-time exposure.

MIC levels obtained for exemplary conjugates according to some embodiments of the present invention, Compounds 1a-q, against selected bacterial strains, are presented in Table 4 below. The MIC values represent the results obtained in parallel experiments with two different starting concentrations of the tested compound (384 and 1.5 µg/ml). AG100B and AG100A are two kanamycin resistant *Escherichia coli* strains expressing APH(3')-I aminoglycoside resistance enzyme [35].

TABLE 4

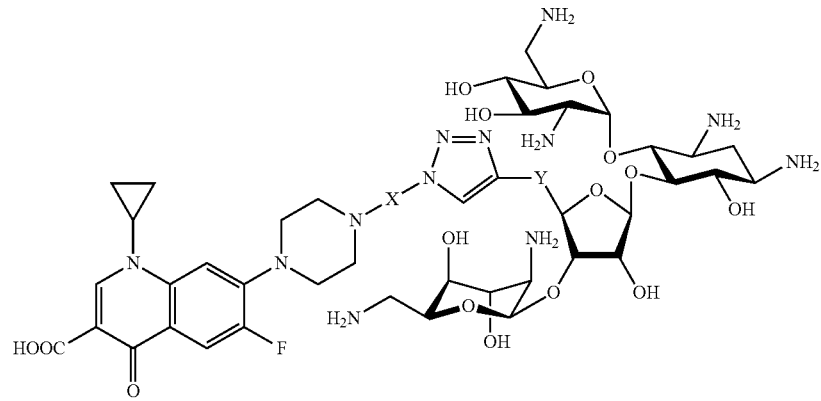

| Compound | X | Y | Yield (%) | E. coli R477-100 | E. coli ATCC 25922 | E. coli AG100B | E. coli AG100A | B. subtilis ATCC 6633 | MRSA ATCC 43300 |
|---|---|---|---|---|---|---|---|---|---|
| "Cipro" | — | — | — | 0.02 | 0.02 | 0.05 | <0.005 | 0.02 | 0.20 |
| "NeoB" | — | — | — | 24 | 48 | 384 | 96 | 1.5 | 384 |
| 1a | —$(CH_2)_2$— | —$C_6H_4$—NHCO— | 63 | 12 | 6 | 24 | 0.75 | 6 | 48 |
| 1b | —$(CH_2)_3$— | —$C_6H_4$—NHCO— | 90 | 6 | 3 | 12 | 1.5 | 6 | 48 |
| 1c | —$(CH_2)_4$— | —$C_6H_4$—NHCO— | 92 | 12 | 6 | 24 | 1.5 | 6 | 24 |
| 1d | —$(CH_2)_5$— | —$C_6H_4$—NHCO— | 94 | 12 | 6 | 24 | 1.5 | 12 | 48 |
| 1e | —$(CH_2)_6$— | —$C_6H_4$—NHCO— | 96 | 6 | 6 | 12 | 1.5 | 12 | 48 |
| 1f | —$CH_2CH(OH)CH_2$— | —$C_6H_4$—NHCO— | 92 | 6 | 3 | 6 | 0.75 | 6 | 24 |
| 1g | —$(CH_2)_2$—O—$(CH_2)_2$— | —$C_6H_4$—NHCO— | 95 | 24 | 12 | 12 | 1.5 | 12 | 24 |
| 1h | —$CH_2$—$mC_6H_4$—$CH_2$— | —$C_6H_4$—NHCO— | 95 | 6 | 12 | 12 | 1.5 | 6 | 12 |
| 1i | —$CH_2$—$pC_6H_4$—$CH_2$— | —$C_6H_4$—NHCO— | 91 | 1.5 | 3 | 3 | 0.75 | 1.5 | 3 |
| 1j | —$(CH_2)_2$— | —$CH_2$—NHCO— | 97 | 12 | 6 | 12 | 1.5 | 3 | 24 |
| 1k | —$(CH_2)_3$— | —$CH_2$—NHCO— | 93 | 12 | 6 | 12 | 1.5 | 6 | 48 |
| 1l | —$(CH_2)_5$— | —$CH_2$—NHCO— | 96 | 24 | 6 | 24 | 1.5 | 12 | 48 |
| 1m | —$CH_2CH(OH)CH_2$— | —$CH_2$—NHCO— | 85 | 6 | 3 | 12 | 0.75 | 3 | 12 |
| 1n | —$(CH_2)_2$—O—$(CH_2)_2$— | —$CH_2$—NHCO— | 90 | 12 | 6 | 12 | 1.5 | 12 | 24 |
| 1o | —$CH_2$—$mC_6H_4$—$CH_2$— | —$CH_2$—NHCO— | 93 | 6 | 6 | 12 | 0.75 | 3 | 6 |
| 1p | —$CH_2$—$pC_6H_4$—$CH_2$— | —$CH_2$—NHCO— | 96 | 6 | 6 | 12 | 1.5 | 3 | 3 |
| 1q | —$(CH_2)_2$— | —$CH_2$—O— | 97 | 3 | 3 | 12 | 0.38 | 0.75 | 6 |

As can be seen in Table 4, all of the exemplary conjugates exhibited significant antibacterial activity. This activity was especially improved in comparison to that of NeoB alone. The most prominent improvement was observed against all E. coli strains including aminoglycosides-resistant strains E. coli AG100A and E. coli AG100B. On average, the conjugates showed 2-8 and 2-16 times better activity than NeoB against E. coli R477-100 and E. coli 25922, respectively, and this was much higher against the resistant E. coli AG100A and E. coli AG100B strains with Compound 1i and Compound 1q as the most active derivatives. Compound 1i was 128-folds more potent than NeoB against E. coli AG100B and E. coli AG100A; Compound 1q was 32-fold better than NeoB against E. coli AG100B and 253-folds better against E. coli AG100A. All the conjugates displayed significantly better potency against the aminoglycosides-resistant Gram-positive MRSA with the activities of 8- to 128-fold better than that of NeoB. The exemplary conjugate Compounds 1i and Compound 1q retained similar activity to that of NeoB in B. subtilis and displayed the most prominent activity against the MRSA.

SAR analysis among the 17 exemplary conjugates presented in Table 4 hereinabove revealed that the length of the linear aliphatic chain at position X (Compounds 1a-e and Compounds 1j-l) has less influence on antibacterial activity, as the variation in antibacterial potency against individual strains is very little. This is valid when comparing between Compounds 1a-e or between Compounds 1j-l of the same sets with respect to the Y spacer, or between Compounds 1a-e and Compounds 1j-l of different sets. Conjugates consisting of the linear aliphatic chain incorporating with alcohol functionality (Compounds 1f and 1m), show better activity than those incorporating with ether functionality (Compounds 1g and 1n) at position X. Among the conjugates containing an aromatic linker at position X (Compounds 1h-i and Compounds 1o-p), Compound 1i that contains para-substituted benzene ring at both X and Y positions displayed the most prominent activity against all bacterial strains tested. The conjugate that displayed similar spectrum of activity to that of Compound 1i was Compound 1q that contains the shortest spacers at both X and Y positions, suggesting that a limited number of degrees of freedom in the spacer have a positive effect on activity. The observation that the majority of conjugates are more active than NeoB against Gram-negative bacteria (E. coli) while retaining moderate activities against the susceptible Gram-positive bacteria (B. subtilis) prompted the investigation of the activity of conjugates against E. coli strains harboring particular aminoglycosides resistant plasmids.

For this purpose, exemplary conjugates, according to some embodiments of the present invention, were tested against five isogenic E. coli strains. E. coli (pSF815) and E. coli (pET9d) are laboratory resistant strains derived by transformation of E. coli XL1 blue (background strain) with the pSF815 and pET9d plasmids, respectively. The pSF815 encodes for the bifunctional AAC(6')/APH(2") resistance enzyme, which catalyses acetylation of the amino group at 6'-$NH_2$ and phosphorylation at the 2"-OH. The pET9d encodes for the APH(3')-Ia resistance enzyme, which catalyses phosphorylation at the 3'-OH of both neomycin and kanamycin families of aminoglycosides. The last two isogenic strains used were E. coli BL21 (background strain) and E. coli (pETSACG1). The latter was derived by transformation of E. coli BL21 with the pETSACG1 plasmid that encodes for the APH(3')-IIIa resistance enzyme. These three enzymes are among the most prevalent modes of resistance found in aminoglycosides resistance strains [36-39].

Since the aminoglycoside resistance of the engineered strains, E. coli (pSF815), E. coli (pET9d) and E. coli (pETSACG1) is mediated only due to the presence of the respective cloned resistance enzyme, comparison of the MIC values against each pair of the resistant and background strains eliminates other effects that could affect the activity of the tested compound, like penetration or solubility. Without being bound by any particular theory, it is suggested that a poorer substrate for the resistance enzyme should have a low ratio between the MIC values of the resistant and non-resistant strains, as demonstrated in several earlier studies [13, 14, 40].

Table 5 presents antibacterial activities of exemplary conjugate according to some embodiments of the present invention, against E. coli XL1 blue and E. coli BL21 (Background Strains) and their Engineered Variants. The MIC ratios were calculated by dividing the MIC value against resistant strain to that against the respective background strain.

Compounds 1i, 1p and 1o against E. coli (pET9d), and for Compound 1p against E. coli (pSF815).

The observed identical MICs of the conjugates against different isogenic pairs of bacteria suggest that the reason for the observed sensitivity of the E. coli harboring either AAC (6')/APH(2") (in case of Compound 1p), APH(3')-Ia (in cases of Compounds 1i, 1p and 1o) or APH(3')-IIIa (in all the tested conjugates) is the inferior activity of these enzymes toward particular conjugates, rather than reduced permeability of the conjugates.

To further substantiate this observation, the detailed kinetic analysis of the purified APH(3')-IIIa enzyme with NeoB along with the exemplary conjugate Compound 1m (that displayed the MIC ratio of 1 against pETSACG1) was carried out according to the previously reported procedure [13].

The measured $K_m$ (μM), $k_{cat}$ ($s^{-1}$) and $k_{cat}/K_m$ ($M^{-1} \times s^{-1}$) values were: 5.7±0.7, 2.4±0.1 and $42 \times 10^{-4}$ for NeoB and 86.8±8.9, 2.5±0.1 and $2.9 \times 10^{-4}$ for Compound 1m, respectively. The kinetic constants measured for NeoB are similar to previously reported values [13, 41]. The observed data indicate that Compound 1m is a poorer substrate of APH(3')-IIIa than NeoB. The observed decrease in specificity for Compound 1m is caused primarily by its poor ability to saturate the enzyme, as judged from its elevated $K_m$ (87 μM) compared to that of the NeoB ($K_m$=6 μM).

The observed kinetic data with Compound 1m is consistent with the antibacterial data presented in Table 5. In fact, comparison of its $K_m$ value (87 μM) with the MIC of 5.5 μM (0.2 μg/ml) against E. coli (pETSACG1), suggests that the bacteria are killed at far lower concentration before the enzyme's full activity is reached.

TABLE 5

| | MIC (μg/ml) | | | | | | | |
|---|---|---|---|---|---|---|---|---|
| | XL1 blue | XL1 blue/ pSF815 | MIC ratio | XL1 blue/ pET9d | MIC ratio | BL21 | BL21/ pETSACG1 | MIC ratio |
| | | Expressed enzyme | | | | | | |
| Compound | — | AAC(6')-APH(2") | | APH(3')-Ia | | — | APH(3')-IIIa | |
| Cipro | 0.10 | 0.38 | 3.8 | 0.10 | 1 | <0.005 | <0.005 | 1 |
| NeoB | 6 | >384 | >64 | 96 | 16 | 6 | 48 | 8 |
| 1i | 3 | 24 | 8 | 3 | 1 | 0.4 | 0.4 | 1 |
| 1m | 6 | 48 | 8 | 12 | 2 | 0.2 | 0.2 | 1 |
| 1o | 6 | 24 | 4 | 6 | 1 | 0.4 | 0.4 | 1 |
| 1p | 6 | 6 | 1 | 6 | 1 | 0.4 | 0.4 | 1 |
| 1q | 3 | 12 | 4 | 12 | 4 | 0.2 | 0.2 | 1 |

As can be seen in Table 5, the MIC values for NeoB are by more than 64-, 16- and 8-fold higher for the resistant strains than the respective non-resistant strains. As expected, the activity of NeoB against the resistant strain harboring bifunctional AAC(6')/APH(2") resistance is significantly lower than those harboring monofunctional APH(3')-Ia or APH(3')-IIIa resistance. All the tested conjugates were less effective than Cipro but displayed significant to excellent activities against resistant strains with the potencies far greater than that of the parent NeoB. The conjugates also displayed similar (E. coli XL1 blue) or better (E. coli BL21) antibacterial efficiency to that of NeoB against susceptible strains.

As can further be seen in Table 5, the MIC ratio for each tested conjugate (calculated by dividing the MIC value against resistant strain to the MIC value against susceptible strain) was significantly lower to that calculated for the NeoB. It is noted herein that this MIC ratio was 1 for the majority of cases: for all the conjugates against E. coli (pETSACG1); for As can further be seen in Table 5, the MIC ratio for Cipro in case of the isogenic E. coli XL1 blue (pSF815)/E. coli XL1 blue strains was 3.8, indicating a modification of this important clinical antibiotic by the aminoglycoside resistant AAC (6')/APH(2") enzyme. Since two other strains harboring APH (3') activity displayed the MIC ratios of 1, it is suggested that Cipro may undergo N-acetylation at the terminal nitrogen of its piperazine moiety by AAC(6')/APH(2"). This suggestion is supported by recent reports demonstrating that some common aminoglycoside acetyltransferases (AACs), including AAC(6')s, are capable of performing N-acetylation of fluoroquinolones having a free amino group at 7-position [42, 43].

In addition, a close inspection of the data in Table 4 reveals that Cipro displayed particularly reduced activity against S. aureus (MRSA); MIC of 0.2 in comparison to MIC values of 0.05 to less than 0.005 against other tested strains. Since the bifunctional AAC(6')/APH(2") enzyme is the most frequently encountered aminoglycoside-modifying enzyme in staphylococci, including MRSA [44], the observed reduced activity of Cipro against *S. aureus* (MRSA) may be explained due to the modification of Cipro by AAC(6')-APH(2").

To further investigate these observations, purification of the bifunctional AAC(6')/APH(2") and the detailed kinetic analysis of Cipro with the homogeneous enzyme, along with the structural characterization of the enzymatic product are performed.

Results of the antibacterial activity assays obtained for the exemplary Cipro-KanA conjugates, Compounds 11a, 11f and 11i, against variety of bacterial strains, including resistant strains, are presented in Table 6 below.

TABLE 6

| | | | MIC (µg/ml) | | | | | | |
|---|---|---|---|---|---|---|---|---|---|
| Compound | X | Y | E. Coli R477-100 | E. coli 25922 | E. coli AG100B | E. coli AG100A | Bacillus subtilis | E. coli XL1 blue | E. coli XL1 blue/pET9d-aph(3')-Ia |
| Cipro | — | | 0.023 | 0.023 | 0.06 | <0.003 | 0.023 | | |
| KanA | — | | 24 | 12 | >384 | 384 | 1.5 | 3 | >384 |
| 11a | —(CH$_2$)$_2$— | CH$_2$ | 6 | 3 | 12 | 0.75 | 1.5 | 6 | 6 |
| 11f | —CH$_2$CH(OH)CH$_2$— | CH$_2$ | 3 | 1.5 | 6 | 0.75 | 1.5 | 3 | 3 |
| 11i | —CH$_2$—pC$_6$H$_4$—CH$_2$— | CH$_2$ | 6 | 6 | 12 | 0.75 | 3 | 3 | 3 |

As can be seen in Table 6, the Cipro-KanA conjugates, according to some embodiments of the present invention, exhibit notable improved antimicrobial activity over that of kanamycin A.

Example 3

Biochemical Studies

To investigate the possibility of a dual mode of action of the conjugates according to some embodiments of the present invention, the exemplary conjugates Compounds 1f, 1i, and 1q were tested for both the inhibition of protein synthesis in an in vitro transcription/translation assay, and the inhibition of the enzymes that are targeted by the quinolones, DNA gyrase and TopoIV (see, Table 7 and FIG. 1).

Purification and kinetic analysis of the APH(3')-IIIa enzyme were performed according to previously described procedure [13].

Protein translation inhibition by the different compounds was quantified in a coupled transcription/translation assay by using *E. coli* S30 extracts for circular DNA with the pBEST/uc plasmid (Promega), according to the manufacturer's protocol.

Translation reactions (25 µl) that contained variable concentrations of the tested compound were incubated at 37° C. for 60 minutes, cooled on ice for 5 minutes, and diluted with a dilution reagent (tris-phosphate buffer (25 mM, pH 7.8), DTT (2 mM), 1,2-diaminocyclohexanetetraacetate (2 mM), glycerol (10%), Triton X-100 (1%) and BSA (1 mg/ml)) into 96-well plates. The luminescence was measured immediately after the addition of the Luciferase Assay Reagent (50 µl; Promega), and the light emission was recorded with a Victor3™ Plate Reader (Perkin-Elmer). The concentration of half-maximal inhibition (IC$_{50}$) was obtained from fitting concentration-response curves to the data of at least two independent experiments by using Grafit 5 software (Leatherbarrow, R. J. Erithacus Software Ltd: Horley, U.K., 2001).

DNA supercoiling activity was assayed with relaxed pBR322 DNA as a substrate (TopoGEN, Inc) according to the manufacturer's protocol. The standard reaction mixture (20 µl) contained 35 mM Tris-Cl pH 7.5, 24 mM KCl, 4 mM MgCl$_2$, 2 mM dithiothreitol, 1.8 mM spermidine, 1 mM ATP, 6.5% glycerol, 0.1 mg/ml BSA, 12.5 µg/µl relaxed pBR322, and DNA gyrase protein. The reaction mixture was incubated at 37° C. for 1 hour, and then was terminated by addition of a loading dye and chloroform/isoamyl alcohol (24:1) mixture. After brief agitation the blue aqua phase was analyzed by electrophoresis in 1% agarose. One unit of supercoiling activity was defined as the amount of DNA gyrase required to supercoil 0.5 µg of plasmid in 1 hour. The IC$_{50}$ was defined as the drug concentration that reduced the enzymatic activity observed with drug-free controls by 50%.

DNA relaxation activity was assayed with supercoiled pBR322 DNA as a substrate (Inspiralis Ltd) according to the manufacturer's protocol. The standard reaction mixture (20 µl) contained 40 mM HEPES-KOH pH 7.6, 100 mM potassium glutamate, 10 mM Mg(OAc)$_2$, 10 mM dithiothreitol, 1 mM ATP, 50 µg/ml albumin, 5 ng/µl relaxed pBR322, and TopoIV protein. The reaction mixture was incubated at 37° C. for 30 minutes, and then was terminated by addition of 2 µl 0.5 M EDTA, 3.5 µl loading dye and 20 µl chloroform/isoamyl alcohol (24:1) mixture. After brief agitation the blue aqua phase was analyzed by electrophoresis in 1% agarose. One unit of relaxation activity was defined as the amount of TopoIV required to relax 0.1 µg of plasmid in 30 minutes. The IC$_{50}$ was defined as the drug concentration that reduced the enzymatic activity observed with drug-free controls by 50%.

FIGS. 1A-D present comparative data for the inhibition of DNA gyrase (FIGS. 1A-B) and TopoIV (FIGS. 1C-D) with Cipro and exemplary Compound 1f, wherein FIG. 1A is a photograph of a 1% agarose gel showing the inhibitory activity of Compound 1f against DNA gyrase (lane 1, relaxed DNA; lane 2, supercoiling reaction by DNA gyrase without presence of inhibitor; lanes 3-8 are the same as lane 1 but in the presence of 30, 60, 100, 150, 200, and 300 nM of Compound 1f); FIG. 1B is a semilogarithmic plot of in vitro DNA gyrase supercoiling reaction inhibition, measured for Cipro and Compound 1f; FIG. 1C is a photograph of a 1% agarose gel showing the inhibitory activity of Compound 1f against TopoIV (lane 1, supercoiled DNA; lane 2, relaxation reaction by TopoIV without the presence of inhibitor; lanes 3-8 are the same as lane 1 but in the presence of 0.2, 0.3, 0.5, 0.8, 1.2, and 10 μM of Compound 1f; FIG. 1D is a semilogarithmic plot of TopoIV inhibition, measured for Cipro and Compound 1f; while the percentages of the supercoiled DNA were calculated from the electrophoresis images by using ImageJ Launcher program (Rasband, W. Bethesda, Md., USA), and plotted as functions of drug concentration (each data point represents the average of 2-3 independent experimental results).

Table 7 present that activity assay data measured for exemplary conjugates according to some embodiments of the present invention, used as inhibitors for DNA expression of gyrase, TopoIV, and bacterial protein synthesis. Super-coiling assay were conducted with $E.$ $coli$ DNA gyrase. Relaxation assays were conducted with $E.$ $coli$ TopoIV. In vitro transcription/translation assay with $E.$ $coli$ S30 extract system. The $IC_{50}$ was defined as the drug concentration that reduced the enzymatic activity observed with drug-free controls by 50%.

TABLE 7

| Compound | DNA gyrase $IC_{50}$ (μM) | TopoIV $IC_{50}$ (μM) | Protein synthesis $IC_{50}$ (μM) |
|---|---|---|---|
| Cipro | 1.3 ± 0.1 | 10.8 ± 0.3 | inactive |
| NeoB | inactive | inactive | 10.5 ± 0.1 |
| 1f | 0.073 ± 0.005 | 0.58 ± 0.04 | 2.2 ± 0.6 |
| 1i | 0.085 ± 0.003 | 0.55 ± 0.06 | 16.7 ± 4.4 |
| 1q | 0.041 ± 0.009 | 7.90 ± 0.25 | 18.1 ± 4.9 |

As can be seen in FIG. 1 and Table 7, the conjugates inhibited bacterial protein synthesis with the potencies similar to or better than that of NeoB, confirming their strong aminoglycoside character and the observed antibacterial activity.

Based on the observed reduced antibacterial activity of all the conjugates in comparison to that of Cipro (Tables 2 and 3), it is expected that the conjugates, according to some embodiments of the present invention, should be weaker DNA gyrase and TopoIV inhibitors than Cipro. However, the exemplary conjugates Compound 1f, 1i, and 1q displayed far greater activities than Cipro in both the DNA gyrase and TopoIV assays, indicating the dual mode of action of these molecules. The measured $IC_{50}$ values for Compound 1f, 1i, and 1q were 18-, 15- and 32-fold superior than that of Cipro in DNA gyrase assay, and 19-, 20- and 1.4-fold superior than Cipro in TopoIV assay. It is of note herein that the $IC_{50}$ values determined for Cipro for the inhibition of DNA gyrase and TopoIV are very similar to those previously reported [11, 45].

These data clearly confirm the design concept of the Cipro-NeoB conjugates, and of the conjugates presented herein in general, and their desired dual mode of action. The observed difference between antibacterial performance and targets inhibition can be explained by the reduced cell penetration of the conjugates in comparison to Cipro. Both the higher molecular weight and the higher overall charge of the conjugates than those of Cipro might contribute to their reduced cell penetration. The observed superior activity of the selected conjugates (like, for example, that of Compounds 1i and 1q) to that of the parent NeoB against a variety of Gram-negative and Gram-positive bacteria including resistant strains along with their established dual mode of action suggest a role for these conjugates in treating infections by resistant bacterial strains and in cases where bacterial resistance may develop.

Example 4

Emergence of Resistance

One advantage of the conjugates, according to some embodiments of the present invention, is their potential to slow the emergence of resistance, as defined in earlier studies [6, 10]. The underline hypothesis is that treatments that inhibit multiple targets might delay and decrease the pathogen's ability to accumulate simultaneous mutations that affect the multiple targets [46].

To assess the potential of emergence of antibacterial resistance to Cipro-NeoB conjugates, the present inventors have used a procedure of selective pressure in which both $E.$ $coli$ ATCC 35218 and $B.$ $subtilis$ ATCC 6633 were exposed to subinhibitory (½ MIC) concentrations of Cipro, NeoB, Cipro:NeoB mixture (1:1 molar ratio), and exemplary conjugate Compound 1i during 15 successive subcultures (see, FIG. 2).

It is noted herein that the MIC values of the Cipro:NeoB mixture (1:1 molar ratio) against the bacterial strains (see, Table 4 hereinabove) were very similar to that of Cipro (on the weight basis of the composition of Cipro into the mixture, data not shown). Therefore, these experiments were designed to include, in addition to Cipro and NeoB, also the mixture Cipro+NeoB.

FIGS. 2A-B and Table 8 hereinafter present comparative data on the emergence of resistance in $E.$ $coli$ (FIG. 2A) and $B.$ $subtilis$ (FIG. 2B) after 15 serial passages in the presence of Cipro, NeoB, Cipro+NeoB mixture (1:1 molar ratio) and an exemplary conjugate, according to some embodiments of the present invention, Compound 1i, wherein relative MIC is the normalized ratio of MIC obtained for a given subculture to MIC obtained upon first exposure.

Table 8 presents a summary of the data examining the potential of emergence of resistance of Gram-negative ($E.$ $coli$ ATCC 35218) and Gram-positive ($B.$ $subtilis$ ATCC 6633) bacteria against Cipro, NeoB, a mixture of Cipro+NeoB (1:1 molar ratio) and the exemplary conjugate according to some embodiments of the present invention, Compound 1i.

TABLE 8

| | MIC (μg/mL) | | | | | |
|---|---|---|---|---|---|---|
| | $E.coli$ ATCC 35218 | | | $B.subtilis$ ATCC 6633 | | |
| Compound | 1st passage | 15th passage | Ratio | 1st passage | 15th passage | Ratio |
| Cipro | 0.01 | 0.75 | 75 | 0.02 | 0.75 | 37.5 |
| Cipro + NeoB | 0.01 | 0.2 | 20 | 0.05 | 0.38 | 7.6 |
| NeoB | 12 | 48 | 4 | 0.75 | 6 | 8 |
| 1i | 3 | 3 | 1 | 3 | 3 | 1 |

As can be seen in FIG. 2 and Table 8, the relative MIC values of Cipro, NeoB and Cipro+NeoB mixture increased by 75-, 4- and 20-fold against *E. coli* and by 37.5-, 8- and 7.6-fold against *B. subtilis*, while that of the exemplary conjugate, Compound 1i, remained unchanged against both *E. coli* and *B. subtilis*. Similar emergence of resistance under same experimental conditions, have been reported for Cipro [47] and aminoglycosides [48].

The ability of the conjugates presented herein to delay the emergence of resistance development was not demonstrated for the previously reported antimicrobial conjugates [6-11]. As such, the observed delay of resistance development towards the conjugate presented herein, compared to that of either Cipro, NeoB and the mixture Cipro+NeoB in both the Gram-negative (*E. coli*) and Gram-positive (*B. subtilis*) bacteria, demonstrate their effectiveness.

Example 5

Conclusions

A series of exemplary conjugates, according to some embodiments of the present invention, containing a covalently linked fluoroquinolone (Cipro) and aminoglycoside (NeoB) with potent antibacterial activity and dual mode of action, has been designed, prepared and tested. It has been shown that the nature of the spacers between the fluoroquinolone and the aminoglycoside moieties may influence the antibacterial activity.

The conjugates were significantly more potent than the parent NeoB, especially against Gram-negative bacteria and Gram-positive MRSA, and overcome most prevalent types of resistance associated with aminoglycosides.

At the isolated target level, the conjugates inhibited bacterial protein synthesis with the potencies similar to or better than that of NeoB, and were up to 32-fold more potent inhibitors than Cipro for the fluoroquinolone targets, DNA gyrase and TopoIV.

The conjugates presented herein demonstrated a significant delay of resistance formation in both Gram-negative (*E. coli*) and Gram-positive (*B. subtilis*) bacteria to the treatment with Cipro-NeoB conjugate in comparison to that of each drug (Cipro and NeoB) separately or their 1:1 mixture.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

REFERENCES CITED BY NUMERALS

Other References are Cited in the Text

1. Kondo, S. and K. Hotta, *Semisynthetic aminoglycoside antibiotics: Development and enzymatic modifications.* J. Infect. Chemother., 1999. 5(1): p. 1-9.
2. Ye, X.-S. and L.-H. Zhang, *Aminoglycoside mimetics as small-molecule drugs targeting RNA.* Curr. Med. Chem., 2002(9): p. 929-939.
3. Umezawa, H. and I. R. Hooper, eds. *Aminoglycoside Antibiotics.* 1982, Springer-Verlag New York, Heidelberg.
4. Magnet, S. and J. S. Blanchard, *Molecular insights into aminoglycoside action and resistance.* Chem Rev, 2005. 105(2): p. 477-98.
5. Vakulenko, S. B. and S. Mobashery, *Versatility of aminoglycosides and prospects for their future.* Clin. Microbiol. Rev., 2003. 16(3): p. 430-50.
6. Bremner, J. B., J. I. Ambrus, and S. Samosorn, *Dual action-based approaches to antibacterial agents.* Curr Med Chem, 2007. 14(13): p. 1459-77.
7. Hubschwerlen, C., et al., *Design, synthesis and biological evaluation of oxazolidinone-quinolone hybrids.* Bioorg Med Chem, 2003. 11(10): p. 2313-9.
8. Grapsas, I., S. A. Lerner, and S. Mobashery, *Conjoint molecules of cephalosporins and aminoglycosides.* Arch Pharm (Weinheim), 2001. 334(8-9): p. 295-301.
9. Johnson, D. M. and R. N. Jones, *CQ-397 and CQ-414: antimicrobial activity and spectrum of two fluoroquinolone—cephalosporin, dual-action compounds with carboxamido bonds.* Clin Microbiol Infect, 1997. 3(3): p. 335-344.
10. Zhi, C., et al., *Hybrid antibacterials. DNA polymerase-topoisomerase inhibitors.* J Med Chem, 2006. 49(4): p. 1455-65.
11. Hubschwerlen, C., et al., *Structure-activity relationship in the oxazolidinone-quinolone hybrid series: influence of the central spacer on the antibacterial activity and the mode of action.* Bioorg Med Chem Lett, 2003. 13(23): p. 4229-33.
12. Long, D. D., et al., *Exploring the positional attachment of glycopeptide/beta-lactam heterodimers.* J Antibiot (Tokyo), 2008. 61(10): p. 603-14.
13. Hainrichson, M., et al., *Branched aminoglycosides: biochemical studies and antibacterial activity of neomycin B derivatives.* Bioorg Med Chem, 2005. 13(20): p. 5797-807.
14. Zhang, J., et al., *Surprising Alteration of Antibacterial Activity of 5"-Modified Neomycin against Resistant Bacteria.* J Med Chem, 2008.
15. Long, D. D. and D. G. Marquess, *Novel heterodimer antibiotics: a review of recent patent literature.* Future Medicinal Chemistry, 2009. 1(6): p. 1037-1050
16. Shakil, S., et al., *Aminoglycosides versus bacteria—a description of the action, resistance mechanism, and nosocomial battleground.* J Biomed Sci, 2008. 15(1): p. 5-14.
17. Zimmer, C., H. Triebel, and H. Thrum, *Interaction of streptothricin and related antibiotics with nucleic acids.* Biochim Biophys Acta, 1967. 145(3): p. 742-51.
18. Ren, Y. G., et al., *Inhibition of Klenow DNA polymerase and poly(A)-specific ribonuclease by aminoglycosides.* Rna, 2002. 8(11): p. 1393-400.
19. Drlica, K. and X. Zhao, *DNA gyrase, topoisomerase IV, and the 4-quinolones.* Microbiol Mol Biol Rev, 1997. 61(3): p. 377-92.
20. Hawkey, P. M., *Mechanisms of quinolone action and microbial response.* J Antimicrob Chemother, 2003. 51 Suppl 1: p. 29-35.
21. Kerns, R. J., et al., *Structural features of piperazinyl-linked ciprofloxacin dimers required for activity against drug-resistant strains of Staphylococcus aureus.* Bioorg Med Chem Lett, 2003. 13(13): p. 2109-12.
22. Sriram, D., et al., *Synthesis and antimycobacterial evaluation of various 7-substituted ciprofloxacin derivatives.* Bioorg Med Chem, 2005. 13(20): p. 5774-8.

23. Hanessian, S., et al., *Structure-based design, synthesis, and A-site rRNA cocrystal complexes of functionally novel aminoglycoside antibiotics: C2" ether analogues of paromomycin.* J Med Chem, 2007. 50(10): p. 2352-69.
24. Francois, B., et al., *Antibacterial aminoglycosides with a modified mode of binding to the ribosomal-RNA decoding site.* Angew Chem Int Ed Engl, 2004. 43(48): p. 6735-8.
25. Kondo, J., et al., *Crystal structure of the bacterial ribosomal decoding site complexed with a synthetic doubly functionalized paromomycin derivative: a new specific binding mode to an a-minor motif enhances in vitro antibacterial activity.* ChemMedChem, 2007. 2(11): p. 1631-8.
26. Linsell, M. G., Adam Aaron; Aggen, James; Moser, Heinz; Hanessian, Stephen; Pachamuthu, Kandasamy; Klegraf, Ellen, *Preparation of 1,4,5-substituted aminoglycoside analogs as antibacterial agents,* P.W.A.C.A. 2008:1247020, Editor. 2008.
27. Haddad, J., et al., *Design of novel antibiotics that bind to the ribosomal acyltransfer site.* J Am Chem Soc, 2002. 124(13): p. 3229-37.
28. Hanessian, S., A. Kornienko, and E. E. Swayze, *Probing the functional requirements of the L-haba side-chain of amikacin-synthesis, 16SA-site rRNA binding, and antibacterial activity.* Tetrahedron, 2003. 59(7): p. 995-1007.
29. Fridman, M., et al., *A new class of branched aminoglycosides: pseudo-pentasaccharide derivatives of neomycin B.* Org Lett, 2003. 5(20): p. 3575-8.
30. Rostovtsev, V. V., et al., *A stepwise huisgen cycloaddition process: copper(I)-catalyzed regioselective "ligation" of azides and terminal alkynes.* Angew Chem Int Ed Engl, 2002. 41(14): p. 2596-9.
31. Yao, L., B. T. Smith, and J. Aube, *Base-promoted reactions of bridged ketones and 1,3-and 1,4-haloalkyl azides: competitive alkylation vs azidation reactions of ketone enolates.* J Org Chem, 2004. 69(5): p. 1720-2.
32. Alper, P. B. H., M.; Sears, P.; and Wong, C.-H., *Probing the Specificity of Aminoglycoside-Ribosomal RNA Interactions with Designed Synthetic Analogs.* JACS 1998. 120: p. 1965-1978.
33. van den Bos, L. J., et al., *Thioglycuronides: synthesis and application in the assembly of acidic oligosaccharides.* Org Lett, 2004. 6(13): p. 2165-8.
34. Thomas, J. R., X. Liu, and P. J. Hergenrother, *Size-specific ligands for RNA hairpin loops.* J Am Chem Soc, 2005. 127(36): p. 12434-5.
35. Okusu, H., D. Ma, and H. Nikaido, *AcrAB efflux pump plays a major role in the antibiotic resistance phenotype of Escherichia coli multiple-antibiotic-resistance (Mar) mutants.* J Bacteriol, 1996. 178(1): p. 306-8.
36. Ida, T., et al., *Identification of aminoglycoside-modifying enzymes by susceptibility testing: epidemiology of methicillin-resistant Staphylococcus aureus in Japan.* J Clin Microbiol, 2001. 39(9): p. 3115-21.
37. Wright, G. D., A. M. Berghuis, and S. Mobashery, *Aminoglycoside antibiotics, Structures, functions, and resistance.* Adv Exp Med Biol, 1998. 456: p. 27-69.
38. Chandrakanth, R. K., S. Raju, and S. A. Patil, *Aminoglycoside-resistance mechanisms in multidrug-resistant Staphylococcus aureus clinical isolates.* Curr Microbiol, 2008. 56(6): p. 558-62.
39. Schmitz, F. J., et al., *The prevalence of aminoglycoside resistance and corresponding resistance genes in clinical isolates of staphylococci from 19 European hospitals.* J Antimicrob Chemother, 1999. 43(2): p. 253-9.
40. Hainrichson, M., et al., *Overexpression and initial characterization of the chromosomal aminoglycoside 3'-O-phosphotransferase APH(3)-IIb from Pseudomonas aeruginosa.* Antimicrob Agents Chemother, 2007. 51(2): p. 774-6.
41. McKay, G. A., P. R. Thompson, and G. D. Wright, *Broad spectrum aminoglycoside phosphotransferase type III from Enterococcus: overexpression, purification, and substrate specificity.* Biochemistry, 1994. 33(22): p. 6936-44.
42. Robicsek, A., et al., *Fluoroquinolone-modifying enzyme: a new adaptation of a common aminoglycoside acetyltransferase.* Nat Med, 2006. 12(1): p. 83-8.
43. Vetting, M. W., et al., *Mechanistic and structural analysis of aminoglycoside N-acetyltransferase AAC(6')-Ib and its bifunctional, fluoroquinolone-active AAC(6')-Ib-cr variant.* Biochemistry, 2008. 47(37): p. 9825-35.
44. Ardic, N., et al., *Investigation of aminoglycoside modifying enzyme genes in methicillin-resistant staphylococci.* Microbiol Res, 2006. 161(1): p. 49-54.
45. Barnard, F. M. and A. Maxwell, *Interaction between DNA gyrase and quinolones: effects of alanine mutations at GyrA subunit residues Ser(83) and Asp(87).* Antimicrob Agents Chemother, 2001. 45(7): p. 1994-2000.
46. Walsh, C., *Where will new antibiotics come from?* Nat Rev Microbiol, 2003. 1(1): p. 65-70.
47. Radzishevsky, I. S., et al., *Improved antimicrobial peptides based on acyl-lysine oligomers.* Nat Biotechnol, 2007. 25(6): p. 657-9.
48. Mor, A., *Peptide-based antibiotics: A potential answer to raging antimicrobial resistance.* Drug Development Research, 2000. 50: p. 440-447.

What is claimed is:

1. A method of treating a bacterial infection in a subject, the method comprising administering to the subject an effective amount of a conjugate having the general formula I:

A-X-D-Y—B    Formula I wherein:
A is a quinolone antimicrobial agent;
B is an aminoglycoside antimicrobial agent;
X is a first spacer moiety, covalently bound to A, or absent;
Y is a second spacer moiety, covalently bound to B, or absent;
D is a linking moiety having the general formula II:

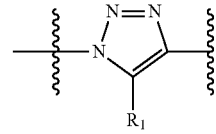

Formula II wherein each of the wiggled lines denote covalent bond to either A-X— or B—Y—, and $R_1$ is selected from the group consisting of hydrogen, alkyl, cycloalkyl and alkenyl, and
the infection is associated with at least one bacterial strain being treatable by at least one of said quinolone antimicrobial agent and said aminoglycoside antimicrobial agent, and has developed or being prone to develop or being capable of developing a resistance to at least one of said quinolone antimicrobial agent and said aminoglycoside antimicrobial agent.

2. The method of claim 1, wherein said bacterial strain is selected from the group consisting of:
(a) Gram-positive bacteria selected from the group consisting of *Strep. pyogenes* (Group A), *Strep. pneumoniae*, Strep. GpB, Strep. viridans, Strep. GpD—(Enterococcus), Strep. GpC and GpG, Staph. aureus, Staph. epidermidis, Bacillus subtilis, Bacillus anthraxis, Listeria monocytogenes, Anaerobic cocci, Clostridium spp., Clostridium difficile and Actinomyces spp;

(b) Gram-negative bacteria selected from the group consisting of Escherichia coli, Enterobacter aerogenes, Kiebsiella pneumoniae, Proteus mirabilis, Proteus vulgaris, Morganella morganii, Providencia stuartii, Serratia marcescens, Citrobacter freundii, Salmonella typhi, Salmonella paratyphi, Salmonella typhimurium, Salmonella virchow, Shigella spp., Yersinia enterocolitica, Acinetobacter calcoaceticus, Flavobacterium spp., Haemophilus influenzae, Pseudomonas aueroginosa, Campylobacter jejuni, Vibrio parahaemolyticus, Brucella spp., Neisseria meningitidis, Neisseria gonorrhoea, Bacteroides fragilis, and Fusobacterium spp., Acinetobacter baumanii, Pseudomonas aeruginosa; and (c) Mycobacterium tuberculosis.

3. The method of claim 1, wherein said bacterial strain is selected from the group consisting of S. aureus ATCC 43300 (MRSA), B. subtilis ATCC 6633, E. coli AG100B, E. coli AG100A, E. coli R477-100, E. coli ATCC 25922 and E. coli ATCC 35218.

4. The method of claim 1, wherein said quinolone antimicrobial agent is selected from the group consisting of a ciprofloxacin (Cipro, Ciprobay, Ciproxin), balofloxacin (Baloxin), cinoxacin (Cinobac), clinafloxacin, danofloxacin (Advocin, Advocid), delafloxacin, difloxacin (Dicural, Vetequinon), enoxacin (Enroxil, Penetrex), enrofloxacin (Baytril), fleroxacin (Megalone, Roquinol), flumequine (Flubactin), garenoxacin (Geninax), gatifloxacin (Tequin, Zymar), gemifloxacin (Factive), grepafloxacin (Raxar), ibafloxacin (Ibaflin), levofloxacin (Cravit, Levaquin), lomefloxacin (Maxaquin), marbofloxacin (Marbocyl, Zenequin), moxifloxacin (Avelox, Vigamox), nadifloxacin (Acuatim, Nadoxin, Nadixa), nalidixic acid (NegGam, Wintomylon), norfloxacin (Lexinor, Noroxin, Quinabic, Janacin), ofloxacin (Floxin, Oxaldin, Tarivid), orbifloxacin (Orbax, Victas), oxolinic acid (Uroxin), pazufloxacin (Pasil, Pazucross), pefloxacin (Peflacine), pipemidic acid (Dolcol), piromidic acid (Panacid), prulifloxacin (Quisnon), rosoxacin (Eradacil), rufloxacin (Uroflox), sarafloxacin (Floxasol, Saraflox, Sarafin), sitafloxacin (Gracevit), sparfloxacin (Zagam), temafloxacin (Omniflox), tosufloxacin (Ozex, Tosacin) and trovafloxacin (Trovan).

5. The method of claim 4, wherein said quinolone-based antimicrobial agent is ciprofloxacin.

6. The method of claim 1, wherein said aminoglycoside antimicrobial agent is selected from the group consisting of neomycin B, neomycin C, streptomycin, framycetin, paromomycin, ribostamycin, kanamycin, amikacin, arbekacin, bekanamycin, dibekacin, tobramycin, spectinomycin, hygromycin, gentamicin, netilmicin, sisomicin, isepamicin, verdamicin and astromicin.

7. The method of claim 6, wherein said aminoglycoside antimicrobial agent is selected from the group consisting of neomycin B and kanamycin A.

8. The method of claim 1, wherein each of X and Y, when present, is independently selected from the group consisting of alkyl, alkenyl, alkynyl, cycloalkyl, heteroalicyclic, aryl, heteroaryl and a hydrocarbon chain having 1-20 carbon atoms and ending or interrupted by at least one heteroatom selected from the group consisting of O, S and N and/or containing from 0 to 19 unsaturated carbon-carbon or carbon-heteroatom bonds.

9. The method of claim 1, wherein each of X and Y, when present, is independently selected from the group consisting of —CH$_2$—, —CH$_2$—O—, —(CH$_2$)$_2$—, —(CH$_2$)$_2$—O—, —(CH$_2$)$_3$—, —(CH$_2$)$_3$—O—, —(CH$_2$)$_4$—, —(CH$_2$)$_5$—, —(CH$_2$)$_6$—, —(CH(CH$_3$))—CH$_2$—, —CH=CH—CH=CH—, —CH$_2$CH(OH)CH$_2$—, —CH$_2$—O—CH$_2$—, —CH$_2$—O—CH$_2$—O—, —(CH$_2$)$_2$—O—(CH$_2$)$_2$—, —(CH$_2$)$_2$—O—(CH$_2$)$_2$—O—, —CH$_2$-mC$_6$H$_4$—CH$_2$—, —CH$_2$-pC$_6$H$_4$—CH$_2$—, —CH$_2$—NHCO—, —C$_6$H$_4$—NHCO—, —CH$_2$—O—CH$_2$— and —CH=CH—CH$_2$—NH—(CH$_2$)$_2$—.

10. A method of treating a bacterial infection in a subject, the method comprising, administering to said subject an effective amount of a conjugate having the general formula III:

$$A'\text{-}X\text{—}W\text{—}Y\text{—}B \qquad \text{Formula III}$$

wherein:
A' is a quinolone antimicrobial agent;
B is an aminoglycoside antimicrobial agent;
X is a first spacer moiety, covalently bound to A, or absent;
Y is a second spacer moiety, covalently bound to B, or absent;
W is a linking moiety, and
the infection is associated with at least one bacterial strain being, treatable by at least one of said quinolone antimicrobial agent and said aminoglycoside antimicrobial agent, and has developed or being prone to develop or being capable of developing a resistance to at least one of said quinolone antimicrobial agent and said aminoglycoside antimicrobial agent.

11. The method of claim 10, wherein said bacterial strain is selected from the group consisting of:

(a) Gram-positive bacteria selected from the group consisting of Strep. pyogenes (Group A), Strep. pneumoniae, Strep. GpB, Strep. viridans, Strep. GpD—(Enterococcus), Strep. GpC and GpG, Staph. aureus, Staph. epidermidis, Bacillus subtilis, Bacillus anthraxis, Listeria monocytogenes, Anaerobic cocci, Clostridium spp., Clostridium difficile and Actinomyces spp;

(b) Gram-negative bacteria selected from the group consisting of Escherichia coli, Enterobacter aerogenes, Kiebsiella pneumoniae, Proteus mirabilis, Proteus vulgaris, Morganella morganii, Providencia stuartii, Serratia marcescens, Citrobacter freundii, Salmonella typhi, Salmonella paratyphi, Salmonella typhi murium, Salmonella virchow, Shigella spp., Yersinia enterocolitica, Acinetobacter calcoaceticus, Flavobacterium spp., Haemophilus influenzae, Pseudomonas aueroginosa, Campylobacter jejuni, Vibrio parahaemolyticus, Brucella spp., Neisseria meningitidis, Neisseria gonorrhoea, Bacteroides fragilis, and Fusobacterium spp., Acinetobacter baumanii, Pseudomonas aeruginosa; and (c) Mycobacterium tuberculosis.

12. The method of claim 10, wherein said bacterial strain is selected from the group consisting of S. aureus ATCC 43300 (MRSA), B. subtilis ATCC 6633, E. coli AG100B, E. coli AG100A, E. coli R477-100, E. coli ATCC 25922 and E. coli ATCC 35218.

13. The method of claim 10, wherein said quinolone antimicrobial agent is selected from the group consisting of a ciprofloxacin (Cipro, Ciprobay, Ciproxin), balofloxacin (Baloxin), cinoxacin (Cinobac), clinafloxacin, danofloxacin (Advocin, Advocid), delafloxacin, difloxacin (Dicural, Vetequinon), enoxacin (Enroxil, Penetrex), enrofloxacin (Baytril), fleroxacin (Megalone, Roquinol), flumequine (Flubactin), garenoxacin (Geninax), gatifloxacin (Tequin, Zymar), gemifloxacin (Factive), grepafloxacin (Raxar), ibafloxacin (Ibaflin), levofloxacin (Cravit, Levaquin), lomefloxacin (Maxaquin), marbofloxacin (Marbocyl, Zenequin), moxifloxacin (Avelox, Vigamox), nadifloxacin (Acuatim, Nadoxin, Nadixa), nalidixic acid (NegGam, Wintomylon), norfloxacin (Lexinor, Noroxin, Quinabic, Janacin), ofloxacin (Floxin, Oxaldin, Tarivid), orbifloxacin (Orbax, Victas), oxolinic acid (Uroxin), pazufloxacin (Pasil, Pazucross), pefloxacin (Peflacine), pipemidic acid (Dolcol), piromidic acid (Panacid), prulifloxacin (Quisnon), rosoxacin (Eradacil), rufloxacin (Uroflox), sarafloxacin (Floxasol, Saraflox, Sarafin), sitafloxacin (Gracevit), sparfloxacin (Zagam), temafloxacin (Omniflox), tosufloxacin (Ozex, Tosacin) and trovafloxacin (Trovan).

14. The method of claim 13, wherein said quinolone antimicrobial agent is ciprofloxacin.

15. The method of claim 14, wherein said ciprofloxacin is covalently bound to X via the terminal nitrogen of the piperazine moiety thereof.

16. The method of claim 10, wherein said aminoglycoside antimicrobial agent is selected from the group consisting of neomycin B, neomycin C, streptomycin, framycetin, paromomycin, ribostamycin, kanamycin, amikacin, arbekacin, bekanamycin, dibekacin, tobramycin, spectinomycin, hygromycin, gentamicin, netilmicin, sisomicin, isepamicin, verdamicin and astromicin.

17. The method of claim 16, wherein said aminoglycoside antimicrobial agent is covalently bound to Y via the C5"-position thereof.

18. The method of claim 17, wherein said aminoglycoside antimicrobial agent is neomycin B.

19. The method of claim 16, wherein said aminoglycoside antimicrobial agent is covalently bound to Y via the C1-N-position thereof.

20. The method of claim 17, wherein said aminoglycoside antimicrobial agent is kanamycin A.

21. The method of claim 10, wherein each of X and Y, when present, is independently selected from the group consisting of alkyl, alkenyl, alkynyl, cycloalkyl, heteroalicyclic, aryl, heteroaryl and a hydrocarbon chain having 1-20 carbon atoms and ending or interrupted by at least one heteroatom selected from the group consisting of O, S and N and/or containing from 0 to 19 unsaturated carbon-carbon or carbon-heteroatom bonds.

22. The method of claim 21, wherein each of X and Y, when present, is independently selected from the group consisting of —$CH_2$—, —$CH_2$—O—, —$(CH_2)_2$—, —$(CH_2)_2$—O—, —$(CH_2)_3$—, —$(CH_2)_3$—O—, —$(CH_2)_4$—, —$(CH_2)_5$—, —$(CH_2)_6$—, —$(CH(CH_3))$—$CH_2$—, —CH═CH—CH═CH—, —$CH_2CH(OH)CH_2$—, —$CH_2$—O—$CH_2$—, —$CH_2$—O—$CH_2$—O—, —$(CH_2)_2$—O—$(CH_2)_2$—, —$(CH_2)_2$—O—$(CH_2)_2$—O—, —$CH_2$-m$C_6H_4$—$CH_2$—, —$CH_2$-p$C_6H_4$—$CH_2$—, —$CH_2$—NHCO—, —$C_6H_4$—NHCO—, —$CH_2$—O—$CH_2$— and —CH═CH—$CH_2$—NH—$(CH_2)_2$—.

23. The method of claim 10, wherein W is selected from the group consisting of a covalent bond, amide, carboxylate, cycloalkene, heteroalicyclic, heteroaryl, triazine, triazole, disulfide, lactone, lactam, imine, hydrazone and semicarbazone.

24. The method of claim 10, wherein W comprises the general formula II:

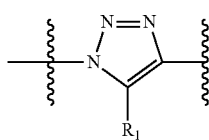

Formula II wherein each of the wiggled lines denote covalent bond to either A-X— or B—Y—, and $R_1$ is selected from the group consisting of hydrogen, alkyl, cycloalkyl and alkenyl.

25. The method of claim 24, wherein $R_1$ is hydrogen.

26. The method of claim 10, being selected from the group consisting of N-(4-(1-(2-(ciprofloxacin)ethyl)-1H-1,2,3-triazol-4-yl)-5"-phenyl) neomycin, N-(4-(1-(2-(ciprofloxacin)propyl)-1H-1,2,3-triazol-4-yl)-5"-phenyl)neomycin carboxamide, N-(4-(1-(2-(ciprofloxacin)butyl)-1H-1,2,3-triazol-4-yl)-5"-phenyl)neomycin carboxamide, N-(4-(1-(2-(ciprofloxacin)pentyl)-1H-1,2,3-triazol-4-yl)-5"-phenyl) neomycin carboxamide, N-(4-(1-(2-(ciprofloxacin)hexyl)-1H-1,2,3-triazol-4-yl)-5"-phenyl)neomycin carboxamide, N-(4-(1-(2-hydroxy-3-(ciprofloxacin)propyl)-1H-1,2,3-triazol-4-yl)-5"-phenyl)neomycin carboxamide, N-(4-(1-(2-(2-(ciprofloxacin)ethoxy)ethyl)-1H-1,2,3-triazol-4-yl)-5"-phenyl)neomycin carboxamide, N-(4-(1-(4-((ciprofloxacin)methyl)benzyl)-1H-1,2,3-triazol-4-yl)-5"-phenyl)neomycin carboxamide, N-(4-(1-(3-((ciprofloxacin)methyl)benzyl)-1H-1,2,3-triazol-4-yl)-5"-phenyl)neomycin carboxamide, N-((1-(4-(ciprofloxacin)ethyl)-1H-1,2,3-triazol-4-yl)-5"-methyl)neomycin carboxamide, N-((1-(4-(ciprofloxacin)propyl)-1H-1,2,3-triazol-4-yl)-5"-methyl)neomycin carboxamide, N-((1-(4-(ciprofloxacin)pentyl)-1H-1,2,3-triazol-4-yl)-5"-methyl)neomycin carboxamide, N-((1-(2-hydroxy-3-(ciprofloxacin)propyl)-1H-1,2,3-triazol-4-yl)-5"-methyl) neomycin carboxamide, N-((1-(2-(2-(ciprofloxacin)ethoxy)ethyl)-1H-1,2,3-triazol-4-yl)-5"-methyl)neomycin carboxamide, N-((1-(3-((ciprofloxacin)methyl)benzyl)-1H-1,2,3-triazol-4-yl)-5"-methyl)neomycin carboxamide, N-((1-(4-((ciprofloxacin)methyl)benzyl)-1H-1,2,3-triazol-4-yl)-5"-methyl)neomycin carboxamide, 4-((5"-neomycin methoxy)methyl)-1-(2-(ciprofloxacin)ethyl)-1H-1,2,3-triazole, 4-(1-N-kanamycin methyl)-1-(2-(ciprofloxacin)ethyl)-1H-1,2,3-triazole, 1-(4-(1-N-kanamycin methyl)-1H-1,2,3-triazol-1-yl)-3-(ciprofloxacin)propan-2-ol and 4-(1-N-kanamycin methyl)-1-(4-((ciprofloxacin)methyl)benzyl)-1H-1,2,3-triazole.

27. A method of inhibiting the growth of at least one bacterial strain while lowering the rate of emergence of antibiotic resistance therein, comprising contacting the bacteria with a conjugate having the general formula I:

A-X-D-Y—B          Formula I wherein:
A is a quinolone antimicrobial agent;
B is an aminoglycoside antimicrobial agent;
X is a first spacer moiety, covalently bound to A, or absent;
Y is a second spacer moiety, covalently bound to B, or absent; and
D is a linking moiety having the general formula II:

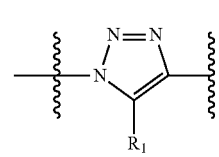

Formula II wherein each of the wiggled lines denote covalent bond to either A-X— or B—Y—, and $R_1$ is selected from the group consisting of hydrogen, alkyl, cycloalkyl and alkenyl, and
said bacterial strain being treatable by at least one of said quinolone antimicrobial agent and said aminoglycoside antimicrobial agent, and has developed or being prone to develop or being capable of developing a resistance to at least one of said quinolone antimicrobial agent and said aminoglvcoside antimicrobial agent.

28. The method of claim 27, wherein said bacterial strain is selected from the group consisting of:
(a) Gram-positive bacteria selected from the group consisting of *Strep. pyogenes* (Group A), *Strep. pneumoniae, Strep.* GpB, *Strep. viridans, Strep.* GpD—(*Enterococcus*), *Strep.* GpC and GpG, *Staph. aureus, Staph. epidermidis, Bacillus subtilis, Bacillus anthraxis, Listeria monocytogenes, Anaerobic cocci, Clostridium* spp., *Clostridium difficile* and *Actinomyces* spp;
(b) Gram-negative bacteria selected from the group consisting of *Escherichia coli, Enterobacter aerogenes, Kiebsiella pneumoniae, Proteus mirabilis, Proteus vulgaris, Morganella morganii, Providencia stuartii, Serratia marcescens, Citrobacter freundii, Salmonella typhi, Salmonella paratyphi, Salmonella typhi murium, Salmonella virchow, Shigella* spp., *Yersinia enterocolitica, Acinetobacter calcoaceticus, Flavobacterium* spp., *Haemophilus influenzae, Pseudomonas aueroginosa, Campylobacter jejuni, Vibrio parahaemolyticus, Brucella* spp., *Neisseria meningitidis, Neisseria gonorrhoea, Bacteroides fragilis,* and *Fusobacterium* spp., *Acinetobacter baumanii, Pseudomonas aeruginosa*; and
(c) *Mycobacterium tuberculosis*.

29. The method of claim 27, wherein said bacterial strain is selected from the group consisting of *S. aureus* ATCC 43300 (MRSA), *B. subtilis* ATCC 6633, *E. coli* AG100B, *E. coli* AG100A, *E. coli* R477-100, *E. coli* ATCC 25922 and *E. coli* ATCC 35218.

30. A method of inhibiting the growth of at least one bacterial strain while lowering the rate of emergence of antibiotic resistance therein, comprising contacting the bacterium with a conjugate having the general formula III:

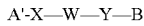    Formula III wherein:
A' is a quinolone antimicrobial agent;
B is an aminoglycoside antimicrobial agent;
X is a first spacer moiety, covalently bound to A, or absent;
Y is a second spacer moiety, covalently bound to B, or absent;
W is a linking moiety,
said bacterial strain being treatable by at least one of said quinolone antimicrobial agent and said aminoglycoside antimicrobial agent, and has developed or being prone to develop or being capable of developing a resistance to at least one of said quinolone antimicrobial agent and said aminoglycoside antimicrobial agent.

31. The method of claim 30, wherein said bacterial strain is selected from the group consisting of:
(a) Gram-positive bacteria selected from the group consisting of *Strep. pyogenes* (Group A), *Strep. pneumoniae, Strep.* GpB, *Strep. viridans, Strep.* GpD—(*Enterococcus*), *Strep.* GpC and GpG, *Staph. aureus, Staph. epidermidis, Bacillus subtilis, Bacillus anthraxis, Listeria monocytogenes, Anaerobic cocci, Clostridium* spp., *Clostridium difficile* and *Actinomyces* spp;
(b) Gram-negative bacteria selected from the group consisting of *Escherichia coli, Enterobacter aerogenes, Kiebsiella pneumoniae, Proteus mirabilis, Proteus vulgaris, Morganella morganii, Providencia stuartii, Serratia marcescens, Citrobacter freundii, Salmonella typhi, Salmonella paratyphi, Salmonella typhi murium, Salmonella virchow, Shigella* spp., *Yersinia enterocolitica, Acinetobacter calcoaceticus, Flavobacterium* spp., *Haemophilus influenzae, Pseudomonas aueroginosa, Campylobacter jejuni, Vibrio parahaemolyticus, Brucella* spp., *Neisseria meningitidis, Neisseria gonorrhoea, Bacteroides fragilis,* and *Fusobacterium* spp., *Acinetobacter baumanii, Pseudomonas aeruginosa*; and
(c) *Mycobacterium tuberculosis*.

32. The method of claim 30, wherein said bacterial strain is selected from the group consisting of *S. aureus* ATCC 43300 (MRSA), *B. subtilis* ATCC 6633, *E. coli* AG100B, *E. coli* AG100A, *E. coli* R477-100, *E. coli* ATCC 25922 and *E. coli* ATCC 35218.

* * * * *